United States Patent
Boyapati et al.

(10) Patent No.: US 11,319,375 B2
(45) Date of Patent: May 3, 2022

(54) METHODS AND COMPOSITIONS FOR TREATING SUBJECTS HAVING RHEUMATOID ARTHRITIS

(71) Applicants: Regeneran Pharmaceuticals, Inc., Tarrytown, NY (US); Sanofi Biotechnology, Paris (FR)

(72) Inventors: Anita Boyapati, Chappaqua, NY (US); Neil Graham, Croton-on-Hudson, NY (US); Toshio Kimura, Kinnelon, NJ (US); Jérôme Msihid, Antony (FR)

(73) Assignees: Regeneron Pharmaceuticals, Inc., Tarrytown, NY (US); Sanofi Biotechnology, Paris (FR)

( * ) Notice: Subject to any disclaimer, the term of this patent is extended or adjusted under 35 U.S.C. 154(b) by 0 days.

(21) Appl. No.: 16/553,338

(22) Filed: Aug. 28, 2019

(65) Prior Publication Data

US 2020/0102395 A1 Apr. 2, 2020

Related U.S. Application Data

(60) Provisional application No. 62/858,443, filed on Jun. 7, 2019, provisional application No. 62/856,431, filed on Jun. 3, 2019, provisional application No. 62/824,399, filed on Mar. 27, 2019, provisional application No. 62/798,697, filed on Jan. 30, 2019, provisional application No. 62/747,301, filed on Oct. 18, 2018, provisional application No. 62/724,212, filed on Aug. 29, 2018.

(30) Foreign Application Priority Data

Aug. 19, 2019 (EP) .................................. 19192387

(51) Int. Cl.
| | |
|---|---|
| *C07K 16/28* | (2006.01) |
| *G01N 33/564* | (2006.01) |
| *A61K 39/395* | (2006.01) |
| *A61P 19/02* | (2006.01) |
| *A61K 39/00* | (2006.01) |

(52) U.S. Cl.
CPC ...... *C07K 16/2866* (2013.01); *A61K 39/3955* (2013.01); *A61P 19/02* (2018.01); *G01N 33/564* (2013.01); *A61K 2039/505* (2013.01); *A61K 2039/545* (2013.01); *C07K 2317/76* (2013.01); *G01N 2333/5412* (2013.01); *G01N 2800/102* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,215,534 A | 6/1993 | De Harde et al. |
| 5,605,690 A | 2/1997 | Jacobs et al. |
| 6,046,223 A | 4/2000 | Sponsel et al. |
| 6,629,949 B1 | 10/2003 | Douglas |
| 6,659,982 B2 | 12/2003 | Douglas et al. |
| 7,582,298 B2 | 9/2009 | Stevens et al. |
| 8,043,617 B2 | 10/2011 | Stevens et al. |
| 8,080,248 B2 | 12/2011 | Radin et al. |
| 8,183,014 B2 | 5/2012 | Stevens et al. |
| 8,192,741 B2 | 6/2012 | Radin et al. |
| 8,562,991 B2 | 10/2013 | Igawa et al. |
| 8,568,721 B2 | 10/2013 | Radin et al. |
| 8,895,521 B2 | 11/2014 | Klinman et al. |
| 9,139,646 B2 | 9/2015 | Solinger et al. |
| 9,173,880 B2 | 11/2015 | Dix et al. |
| 9,248,242 B2 | 2/2016 | Verespej et al. |
| 9,308,256 B2 | 4/2016 | Radin et al. |
| 9,427,531 B2 | 8/2016 | Hourmand et al. |
| 9,884,916 B2 | 2/2018 | Stevens et al. |
| 9,943,594 B2 | 4/2018 | Jasson et al. |
| 10,072,086 B2 | 9/2018 | Dix et al. |
| 2004/0202658 A1 | 10/2004 | Benyunes |
| 2007/0280945 A1* | 12/2007 | Stevens .................. A61P 29/00 424/145.1 |
| 2008/0131374 A1 | 6/2008 | Medich et al. |
| 2008/0269467 A1 | 10/2008 | Allan et al. |
| 2009/0082288 A1 | 3/2009 | Klinman et al. |
| 2010/0031663 A1 | 2/2010 | Commaret et al. |
| 2010/0316627 A1 | 12/2010 | Stevens et al. |
| 2011/0098450 A1 | 4/2011 | Igawa et al. |
| 2011/0171241 A1 | 7/2011 | Dix et al. |
| 2012/0003697 A1 | 1/2012 | Stevens et al. |
| 2012/0171123 A1 | 7/2012 | Medich et al. |
| 2012/0258098 A1 | 10/2012 | Radin et al. |

(Continued)

FOREIGN PATENT DOCUMENTS

| | | |
|---|---|---|
| EH | 2013/037902 A2 | 3/2013 |
| EP | 0 628 639 B1 | 12/1994 |

(Continued)

OTHER PUBLICATIONS

Burmester et al, Annals of the Rheumatic Diseases; 2017 vol. 76, No. 5, pp. 840-847.*
"Sarilumab" heavy and light chain sequences from https://go.drugbank.com/drugs/DB11767; accessed Feb. 21, 2021.*
Tanaka et al., Annals of the Rheumatic Diseases; 2014 vol. 73, No. 9, pp. 1595-1597.*
Nishimoto et al., Blood, 2008, vol. 112, No. 10, pp. 3959-3964.*
Phase II Study to Analyze Sarilumab in Non-Infectious Uveitis, NCT01900431 on Apr. 13, 2015, ClinicalTrials.gov Archive, URL: https://clinicaltrials.gov/archive/NCT01900431. (Apr. 13, 2015).

(Continued)

*Primary Examiner* — Bridget E Bunner
*Assistant Examiner* — Fozia M Hamud
(74) *Attorney, Agent, or Firm* — McCarter & English, LLP; Marcie B. Clarke; Deborah L. Nagle

(57) ABSTRACT

Disclosed herein are methods for treating subjects having rheumatoid arthritis (RA) with a human anti-interleukin 6 (IL-6) antibody, or antigen-binding portion thereof.

13 Claims, 22 Drawing Sheets

Specification includes a Sequence Listing.

(56) References Cited

U.S. PATENT DOCUMENTS

| | | |
|---|---|---|
| 2013/0149310 A1 | 6/2013 | Jasson et al. |
| 2014/0255390 A1 | 9/2014 | Radin et al. |
| 2014/0302053 A1 | 10/2014 | Huang et al. |
| 2016/0002341 A1 | 1/2016 | Dix et al. |
| 2016/0229916 A1 | 8/2016 | Stevens et al. |
| 2016/0280782 A1 | 9/2016 | Huang et al. |
| 2017/0166646 A1 | 6/2017 | Sridhara Sundaram et al. |
| 2017/0252434 A1 | 9/2017 | Joseph et al. |
| 2018/0296670 A1 | 10/2018 | Jasson et al. |
| 2019/0002574 A1 | 1/2019 | Dix et al. |
| 2019/0100585 A1 | 4/2019 | Bauer et al. |

FOREIGN PATENT DOCUMENTS

| | | |
|---|---|---|
| EP | 0 783 893 B1 | 7/1997 |
| WO | WO-1992/016553 A1 | 10/1992 |
| WO | WO-1992/019759 A1 | 11/1992 |
| WO | WO-1994/006476 A1 | 3/1994 |
| WO | WO-1996/011020 A1 | 4/1996 |
| WO | WO-2002/100330 A2 | 12/2002 |
| WO | WO-2006/033702 A2 | 3/2006 |
| WO | WO-2007/070750 A1 | 6/2007 |
| WO | WO-2007/143168 A2 | 12/2007 |
| WO | WO-2010/106812 A1 | 9/2010 |
| WO | WO-2010/149771 A1 | 12/2010 |
| WO | WO-2011/085158 A2 | 7/2011 |
| WO | WO-2013/053751 A1 | 4/2013 |
| WO | WO-2015/077582 A1 | 5/2015 |
| WO | WO-2016/044343 A1 | 3/2016 |
| WO | WO-2017/079443 A1 | 5/2017 |
| WO | WO-2017/155990 A1 | 9/2017 |

OTHER PUBLICATIONS

Study of the Safety, Tolerability, and Bioactivity of Tocilizumab on Patients with Non-infectious UVEITIS: The STOP-UVEITIS Study (STOP-Uveitis), Available at: https://clinicaltrials.gov/ct2/show/NCT01717170. (Oct. 29, 2010).

Adan, et al. "Tocilizumab Treatment for Refractory Uveitis-Related Cystoid Macular Edema", Graefes Archive for Clinical and Experimental Ophthalmology, vol. 251, No. 11, pp. 2627-2632 (Jul. 27, 2013).

Aletaha, et al. "Rheumatoid Arthritis Classification Criteria: An American College of Rheumatology/European League Against Rheumatism Collaborative Initiative", Arthritis and Rheumatology, vol. 62, No. 9, pp. 2569-2581 (Sep. 2010).

An, et al. The Addition of Tocilizumab to DMARD Therapy for Rheumatoid Arthritis: A Meta-Analysis of Randomized Controlled Trials, European Journal of Clinical Pharmacology, vol. 66, No. 1, pp. 49-59 (Jan. 2010).

Barry, et al. "Pharmacotherapy for Uveitis: Current Management and Emerging Therapy", Clinical Ophthalmology, vol. 8, pp. 1891-1911 (Sep. 1, 2014).

Burmester, et al. "A Randomised, Double-Blind, Parallel-Group Study of the Safety and Efficacy of Subcutaneous Tocilizumab Versus Intravenous Tocilizumab in Combination with Traditional Disease-Modifying Antirheumatic Drugs in Patients with Moderate to Severe Rheumatoid Arth", Annals of the Rheumatic Diseases, vol. 73, No. 1, pp. 69-74 (Jan. 2014).

Burmester, et al. "Efficacy and Safety of Sarilumab Monotherapy Versus Adalimumab Monotherapy for The Treatment of Patients with Active Rheumatoid Arthritis (Monarch): A Randomised, Double-Blind, Parallel-Group Phase III Trial", Annals of the Rheumatic Diseases, vol. 76, No. 5, pp. 840-847 (May 2017).

Emery, et al. "IL-6 Receptor Inhibition with Tocilizumab Improves Treatment Outcomes in Patients with Rheumatoid Arthritis Refractory to Anti-Tumour Necrosis Factor Biologicals: Results From a 24-Week Multicentre Randomised Placebo-Controlled Trial", Annals of the Rheumatic Diseases, vol. 67, No. 11, pp. 1516-1523 (Nov. 2008).

Fleischmann, et al. "Comparable Efficacy with Sarilumab Plus Methotrexate in Biologic-Experienced and Biologic-Naïve Patients with Moderate-to-Severe Rheumatoid Arthritis from a Phase 3, Randomized, Double-Blind, Placebo-Controlled, International Study", Arthritis & Rheumatology, vol. 66, No. S10, pp. S1232 (Oct. 2014).

Gandek, et al. "Psychometric Evaluation of the SF-36® Health Survey in Medicare Managed Care", Health Care Financing Review, vol. 25, No. 4, pp. 5-25 (2004).

Genovese, et al. "Sarilumab Plus Methotrexate in Patients with Active Rheumatoid Arthritis and Inadequate Response to Methotrexate: Results of a Phase III Study", Arthritis & Rheumatology, vol. 67, No. 6, pp. 1424-1437 (Jun. 2015).

Hennigan, et al."Interleukin-6 Inhibitors in the Treatment of Rheumatoid Arthritis", Therapeutics and clinical risk management, vol. 4, No. 4, pp. 767-775 (Aug. 2008).

Huizinga, et al. "Sarilumab, A Fully Human Monoclonal Antibody Against IL-6Rα in Patients with Rheumatoid Arthritis and an Inadequate Response to Methotrexate: Efficacy and Safety Results from the randomised SARIL-RA-MOBILITY Part A Trial", Annals of the Rheumatic Diseases, vol. 73, No. 9, pp. 1626-1629 (Sep. 2014).

International Search Report and Written Opinion received for PCT Patent Application No. PCT/EP2012/070052, dated Jan. 10, 2013, 10 Pages.

International Search Report and Written Opinion received for PCT Patent Application No. PCT/US2012/070052, dated Mar. 18, 2013, 7 Pages.

International Search Report and Written Opinion received for PCT Patent Application No. PCT/US2014/066856, dated Apr. 2, 2015, 11 Pages.

International Search Report and Written Opinion received for PCT Patent Application No. PCT/US2015/050291, dated Dec. 1, 2015, 12 Pages.

International Search Report and Written Opinion received for PCT Patent Application No. PCT/US2016/060344, dated Mar. 13, 2017, 14 pages.

International Search Report and Written Opinion received for PCT Patent Application No. PCT/US2017/021149, dated Jul. 18, 2017, 15 Pages.

Kivitz, et al. "Subcutaneous Tocilizumab Versus Placebo in Combination with Disease-Modifying Antirheumatic Drugs in Patients with Rheumatoid Arthritis", Rheumatoid Arthritis, vol. 66, Issue 11, pp. 1653-1661 (Nov. 2014).

Lin "Targeting Interleukin-6 For Noninfectious Uveitis", Clinical Ophthalmology, vol. 9, pp. 1697-1702 (Sep. 1, 2015).

Lipsky, "Interleukin-6 and Rheumatic Diseases", Arthritis Research & Therapy, vol. 8, Suppl 2, S4, pp. 1-5 (2006).

Merida, et al. "New Immunosuppressive Therapies in Uveitis Treatment", International Journal of Molecular Sciences, vol. 16, No. 8, pp. 18778-18795 (Aug. 11, 2015).

Mesquida, et al. "Long-Term Effects of Tocilizumab Therapy for Refractory Uveitis-Related Macular Edema", Ophthalmology, vol. 121, No. 12, pp. 2380-2386 (Sep. 6, 2014).

Nguyen, et al. "The SATURN Study (SARIL-NIU): Sarilumab for the Treatment of Posterior Segment Non-Infectious Uveitis (NIU)", Investigative Ophthalmology & Visual Science, vol. 56, No. 7, 3116 pages (Jun. 2015).

Nicassio, et al."The Contribution of Pain and Depression to Self-Reported Sleep Disturbance in Patients with Rheumatoid Arthritis", Pain, vol. 153, No. 1, pp. 107-112 (Jan. 2012).

Nishimoto, et al. "Study of Active Controlled Tocilizumab Monotherapy for Rheumatoid Arthritis Patients with an Inadequate Response to Methotrexate (SATORI): Significant Reduction in Disease Activity and Serum Vascular Endothelial Growth Factor by IL-6 Receptor Inhibition Th", Modern Rheumatology, vol. 19, No. 1, pp. 12-19 (Nov. 1, 2008).

Radin, et al. "Safety and Effects on Markers of Inflammation of Subcutaneously Administered regn88/sar153191 (regn88), an Interleukin-6 Receptor Inhibitor, in Patients with Rheumatoid Arthritis: Findings from Phase 1 Studies", Annals of the Rheumatic Diseases, vol. 69, Supplement 3, p. 99 (Jan. 1, 2010).

Radin, et al. "REGN88/SAR153191, a fully-human interleukin-6 receptor monoclonal antibody, reduces acute phase reactants in

(56) References Cited

OTHER PUBLICATIONS patients with rheumatoid arthritis: preliminary observations from Phase 1 studies.", Arthritis & Rheumatology, vol. 62, Supplement 10, XP008158581, p. S1121 (Nov. 2010).
Rafique, et al. "Evaluation of The Binding Kinetics and Functional Bioassay Activity of Sarilumab and Tocilizumab to The Human IL-6 Receptor (IL-6r) alpha", Annals of the Rheumatic Diseases, vol. 72, Issue Suppl 3, pp. A797.1-A797 (Jun. 23, 2013).
Regeneron (Nov. 22, 2013) "Sanofi and Regeneron Report Positive Results with Sarilumab in First Phase 3 Rheumatoid Arthritis Registration Trial", Press Release, Acquire Media, Available at: https://investor.regeneron.com/news-releases/news-release-details/sanofi-and-regeneron-report-positive-results-sarilumab-first, 6 pages.
Regeneron Pharmaceuticals (Jul. 12, 2011) "Evaluation of Sarilumab (SAR153191/REGN88) on Top of Methotrexate in Rheumatoid Arthritis Patients (RA-MOBILITY)", Retrieved from the internet from URL «https://clinicaltrials.gov/ct2/results?term=SAR+153191=mobility».
Sanofi (Feb. 2, 2010) "Evaluation of Sarilumab (SAR153191/REGN88) on Top of Methotrexate in Rheumatoid Arthritis Patients (RA-MOBILITY)", Clinical Trials.gov, Retrieved from http://clinicaltrials.gov/show/NCT01061736.
Sanofi (Oct. 7, 2010) "Effect of SAR153191 (REGN88) With Methotrexate in Patients with Active Rheumatoid Arthritis Who Failed TNF-? Blockers", ClinicaiTrials.gov, Retrieved from http://clinicaltrials.gov/show/NCT01217814, 11 pages.
Sanofi and Regeneron (Nov. 8, 2015) "Regeneron and Sanofi Present Results from Pivotal Phase 3 Study of Sarilumab at American College of Rheumatology Annual Meeting", Press Release, Regeneron Pharmaceuticals, Inc. Retrieved from http://investor.regeneron.com/releasedetail.cfm?releaseid=941387.
Smolen, et al. "Effect of Interleukin-6 Receptor Inhibition with Tocilizumab in Patients with Rheumatoid Arthritis (Option Study): A Double-Blind, Placebo-Controlled, Randomised Trial", The Lancet, vol. 371, Issue 9617, pp. 987-997 (Mar. 22-28, 2008).
Strand, et al. "Health-related Quality of Life Outcomes of Adalimumab for Patients with Early Rheumatoid Arthritis: Results from a Randomized Multicenter Study", The Journal of Rheumatology, vol. 39, pp. 63-72 (2012).
Taylor "Pharmacology of TNF Blockade in Rheumatoid Arthritis and Other Chronic Inflammatory Diseases", Current Opinion in Pharmacology, vol. 10, Issue 3, pp. 308-315 (Jun. 2010).
The Chemical Abstracts Service CAS, 1189541-98-7, 2021.
Vasanthi, et al. "Role of Tumor Necrosis Factor-Alpha in Rheumatoid Arthritis: A Review", APLAR Journal of Rheumatology, vol. 10, No. 4, pp. 270-274 (Dec. 2007).
Ware, et al. "SF-36 Physical and Mental Health Summary Scales: A User's Manual", Health Assessment Lab, New England Medical Center, Boston: The Health Institute, 190 Pages (1994).
Whalley, et al. "Quality of Life in Rheumatoid Arthritis", British Journal of Rheumatology, vol. 36, pp. 884-888 (1997).
Wiens, et al. "A Systematic Review and Meta-Analysis of the Efficacy and Safety of Adalimumab for Treating Rheumatoid Arthritis", Rheumatology International, vol. 30, Issue 8, pp. 1063-1070 (Jun. 2010).
Non-Final Office Action received for U.S. Appl. No. 14/350,973, daated Feb. 5, 2016, 18 Pages.
Notice of Allowance received for U.S. Appl. No. 14/350,973, dated Jun. 14, 2016, 8 Pages.
Raimondo et al, "Profile of sarilumab and its potential in the treatment of rheumatoid arthritis", Drug Design, Development and Therapy, (May 1, 2017), vol. 11, pp. 1593-1603.
Yoshida et al, "Interleukin 6 and Rheumatoid Arthritis", Biomed Research International, (Jan. 1, 2014), vol. 2014, ISSN 2314-6133, pp. 1-12.
Chung et al, "The Correlation between Increased Serum Concentrations of Interleukin-6 Family Cytokines and Disease Activity in Rheumatoid Arthritis Patients", Yonsei Medical Journal, (Jan. 1, 2011), vol. 52, No. 1, ISSN 0513-5796, pp. 113-120.
Boyapati et al, "High baseline serum IL-6 identifies a subgroup of rheumatoid arthritis patients with rapid joint damage and clinical progression and predicts increased sarilumab treatment response", Rheumatology, vol. 58, Issue Supplement_3, Apr. 2019.
Boyapati et al, "High Baseline Serum IL-6 Identifies a Subgroup of Rheumatoid Arthritis Patients with Rapid Joint Damage and Clinical Progression and Predicts Increased Sarilumab Treatment Response", 2018 ACR/ARHP Annual Meeting, (Oct. 4, 2018).

* cited by examiner

| MOBILITY | | | |
|---|---|---|---|
| Baseline parameter, mean (SD) | Low IL-6 tertile (n=397) | Medium IL-6 tertile (n=396) | High IL-6 tertile (n=398) |
| Sarilumab 150 mg/200 mg+MTX/PBO+MTX, n | 126/128/143 | 129/147/122 | 146/121/131 |
| IL-6, pg/mL, median [range] | 4.97 [1.6–9.6] | 17.30 [9.8–30.7] | 61.01 [31.2–648.7] |
| CRP (mg/L) | 10.5 (11.6) | 18.3 (15.5) | 36.4 (30.1)* |
| mTSS | 40.8 (56.5) | 49.8 (62.1) | 56.7 (65.7)* |
| HAQ-DI | 1.58 (0.61) | 1.59 (0.64) | 1.76 (0.65)* |
| DAS28-CRP | 5.60 (0.81) | 5.91 (0.84) | 6.34 (0.83)* |
| CDAI | 38.31 (11.64) | 40.09 (12.27) | 43.01 (12.39)* |
| TJC | 25.93 (14.02) | 26.72 (14.15) | 27.79 (14.14) |
| SJC | 15.81 (9.07) | 16.52 (9.28) | 17.72 (9.52)* |
| MONARCH | | | |
| | Low IL-6 tertile (n=100) | Medium IL-6 tertile (n=100) | High IL-6 tertile (n=100) |
| Adalimumab/sarilumab, n | 45/55 | 53/47 | 54/46 |
| IL-6, pg/mL, median [range] (normal <12.5 pg/mL) | 2.96 [1.6–7.1] | 16.18 [7.2–39.5] | 64.69 [39.6–692.3] |
| CRP, mg/L (normal <2.87 mg/L) | 5.62 (9.18) | 15.24 (17.14) | 41.51 (34.14)* |
| HAQ-DI | 1.46 (0.57) | 1.63 (0.58) | 1.83 (0.57)* |
| DAS28-CRP | 5.50 (0.76) | 6.00 (0.74) | 6.54 (0.82)* |
| DAS28-ESR | 6.54 (0.70) | 6.78 (0.68) | 7.12 (0.85)* |
| CDAI | 40.60 (11.71) | 42.85 (11.41) | 45.98 (12.20)* |
| TJC | 26.32 (13.07) | 28.15 (13.97) | 27.76 (13.94) |
| SJC | 15.91 (10.14) | 18.58 (10.01) | 18.83 (10.74)* |

*$P<0.05$ (Kruskal-Wallis test)
DAS28, Disease Activity Score in 28 joints; ESR, erythrocyte sedimentation rate; LDA, low disease activity

FIG. 3

| Sarilumab 200 mg q2w/placebo (all +MTX), n | High IL-6 (N=388) 121/131 | Medium IL-6 (N=398) 147/122 | Low IL-6 (N=397) 128/143 | Interaction P-value (high vs low IL-6) |
|---|---|---|---|---|
| Odds ratio (95% CI)‡ sarilumab 200 mg q2w+MTX vs placebo q2w+MTX (Week 52) | | | | |
| mTSS progression | 0.3 (0.1, 0.4) | 0.6 (0.4, 1.0) | 0.7 (0.4, 1.1) | * |
| ACR20 | 4.9 (2.8, 8.3) | 3.3 (1.9, 5.7) | 2.0 (1.2, 3.2) | * |
| ACR50 | 6.4 (3.5, 11.8) | 3.4 (1.9, 6.2) | 2.0 (1.2, 3.4) | * |
| ACR70 | 7.3 (3.3, 16.3) | 3.5 (1.7, 7.4) | 1.9 (1.0, 3.8) | * |
| DAS28-CRP <2.6 | 39.3 (9.4, 163.9) | 4.4 (2.2, 8.9) | 2.5 (1.4, 4.7) | * |
| CDAI ≤2.8 | 42.4 (4.7, 383.3) | 3.9 (1.6, 9.5) | 1.8 (0.8, 4.0) | * |
| HAQ-DI improvement ≥0.3 (Week 16) | 3.1 (1.8, 5.2) | 2.2 (1.3, 3.7) | 1.1 (0.7, 1.8) | * |

FIG. 6

| Sarilumab/adalimumab, n | High IL-6 (N=100) 46/54 | Medium IL-6 (N=100) 47/53 | Low IL-6 (N=100) 55/45 | Interaction P-value (high vs low IL-6) |
|---|---|---|---|---|
| Odds ratio (95% CI)ᵃ sarilumab vs adalimumab (Week 24) | | | | |
| ACR20 | 6.6 (2.3, 18.6) | 1.2 (0.5, 3.0) | 1.4 (0.6, 3.1) | * |
| ACR50 | 5.5 (2.3, 13.2) | 1.5 (0.6, 3.5) | 1.6 (0.7, 3.7) | * |
| ACR70 | 10.5 (2.3, 48.4) | 1.7 (0.6, 4.6) | 1.1 (0.4, 3.2) | * |
| DAS28-ESR <2.6 | 33.9 (3.5, 328.7) | 5.6 (1.6, 19.4) | 1.5 (0.5, 4.4) | * |
| DAS28-ESR <3.2 | 10.5 (3.5, 31.4) | 5.1 (1.8, 14.1) | 2.6 (1.0, 6.7) | |
| DAS28-CRP <2.6 | 18.5 (3.8, 90.0) | 4.0 (1.5, 10.9) | 2.0 (0.8, 5.3) | * |
| DAS28-CRP <3.2 | 9.2 (3.4, 24.8) | 2.2 (1.0, 5.1) | 3.2 (1.3, 7.6) | |
| CDAI ≤10 | 3.6 (1.4, 9.0) | 1.6 (0.7, 3.7) | 3.1 (1.2, 7.7) | |
| HAQ-DI improvement ≥0.3 | 4.5 (1.8, 10.9) | 1.4 (0.6, 3.2) | 1.4 (0.6, 3.2) | |

FIG. 9

| MOBILITY: Endpoints at Week 52 | Odds ratio (95% CI) sarilumab 200 mg+MTX vs placebo+MTX[a] | | |
|---|---|---|---|
| | All (biomarker population) | High IL-6 (median 61 pg/mL) | High CRP (median 37 mg/L) |
| ACR20 | 3.1 (2.3, 4.1) | 4.9 (2.8, 8.3)* | 3.8 (2.3, 6.5) |
| ACR50 | 3.4 (2.4, 4.7) | 6.4 (3.5, 11.8)* | 4.6 (2.5, 8.3) |
| ACR70 | 3.7 (2.4, 5.5) | 7.3 (3.3, 16.3)* | 5.5 (2.6, 11.5)* |
| DAS28-CRP <2.6 | 5.5 (3.7, 8.3) | 39.3 (9.4, 163.9)* | 16.3 (6.0, 44.2)* |
| CDAI ≤2.8 | 4.4 (2.6, 7.5) | 42.4 (4.7, 383.3)* | 19.3 (4.3, 86.2)* |

| MONARCH: Endpoints at Week 24 | Odds ratio (95% CI) sarilumab vs adalimumab[b] | | |
|---|---|---|---|
| | All (biomarker population) | High IL-6 (median value 65 pg/mL) | High CRP (median value 38 mg/L) |
| ACR20 | 2.0 (1.2, 3.2) | 6.6 (2.3, 18.6)* | 3.7 (1.5, 8.9)* |
| ACR50 | 2.4 (1.5, 3.8) | 5.5 (2.3, 13.2)* | 3.5 (1.5, 8.0) |
| ACR70 | 2.4 (1.3, 4.5) | 10.5 (2.3, 48.4)* | 4.4 (1.3, 14.1) |
| DAS-CRP <2.6 | 3.5 (2.0, 6.3) | 18.5 (3.8, 90.0)* | 7.6 (2.0, 28.5) |
| CDAI ≤10 | 2.3 (1.4, 3.7) | 3.6 (1.4, 9.0) | 2.8 (1.1, 7.0) |
| HAQ-DI improvement ≥0.22 | 2.0 (1.2, 3.2) | 5.0 (1.9, 13.2)* | 2.8 (1.2, 6.5) |

*Nominal P<0.05 for high vs low tertile IL-6-by-treatment interaction (logistic regression with treatment, study randomization stratification factors region for MOBILITY and MONARCH, prior biologic use for MOBILITY], tertile IL-6 at baseline, and tertile IL-6 at baseline-by-treatment interaction as fixed effects)

[b]Mantel-Haenszel odds ratio stratified by study randomization stratification factors

FIG. 10A

| Endpoints at Week 52 | All (biomarker population) | High IL-6 (median 61 ng/L) | High CRP (median 37 mg/L) |
|---|---|---|---|
| | OR (95% CI) Sarilumab 200 mg + MTX vs. placebo + MTX** | | |
| ACR20 | 3.0 (2.2, 4.1) | 4.9 (2.8, 8.3)* | 3.8 (2.2, 6.5) |
| ACR50 | 3.4 (2.4, 4.6) | 6.4 (3.5, 11.8)* | 4.6 (2.5, 8.3) |
| ACR70 | 3.7 (2.4, 5.5) | 7.3 (3.3, 16.3)* | 5.4 (2.6, 11.5)* |
| DAS-CRP remission (<2.6) | 5.5 (3.7, 8.3) | 39.3 (9.4, 163.9)* | 16.3 (6.0, 44.2)* |
| CDAI remission | 4.4 (2.5, 7.4) | 42.4 (4.7, 383.4)* | 19.3 (4.3, 86.1)* |
| mTSS progression Low OR= less progression | 0.49 (0.4, 0.7) | 0.26 (0.1, 0.4)* | 0.39 (0.23, 0.67) |
| ES progression | 0.46 (0.3, 0.6) | 0.26 (0.1, 0.4)* | 0.42 (0.25, 0.7) |

*Endpoints with significant IL-6 tertile-by-treatment interaction p values for high vs. low comparison (Logistic regression with treatment, tertile biomarker, prior biological use and region as fixed effects, and the tertile biomarker-by-treatment interaction). OR in bold are significant (p<0.05) relative to placebo + MTX

**Mantel-Haenszel estimate stratified by number of previous anti-TNFs and region ACR20/50/70, proportion of patients achieving ≥20/50/70% improvement according to ACR criteria; CDAI, Clinical Disease Activity Index; CRP, C-reactive protein; DAS, Disease Activity Score; ES, erosion score; IL-6, interleukin-6; mTSS, modified total Sharp score; MTX, methotrexate; OR, odds ratio; q2w, every 2 weeks; TNF, tumor necrosis factor

FIG. 10B

| Endpoint at week 24, response rate difference vs comparator (%) | MONARCH | MOBILITY* |
|---|---|---|
| ACR20 | 37.2 | 38.3 |
| ACR50 | 41.1 | 31.8 |
| ACR70 | 26.7 | 25.2 |
| CDAI LDA | 24.5 | 31.6 |
| CDAI remission | 4.3 | 14.4 |
| DAS-CRP LDA | 45.7 | 44.5 |
| DAS-CRP remission | 33.3 | 28.6 |
| HAQ-DI ≥0.22 | 33.3 | 21.7 |

*Sarilumab 200 mg
LDA, low disease activity

FIG. 11A

| Endpoints at Week 24, responders % | MONARCH IL6>39 pg/ml | MOBILITY IL-6>31 pg/ml |
|---|---|---|
| ACR20 | 37 | 38.2 |
| ACR50 | 40.3 | 32 |
| ACR70 | 26 | 25 |
| CDAI LDA | 24 | 32 |
| CDAI remission | 4.3 | 14 |
| DAS-CRP LDA | 46 | 45 |
| DAS-CRP remission | 33 | 29 |
| HAQ-DI * 0.22 | 33 | 23 |

ACR20/50/70, proportion of patients achieving ≥20/50/70% improvement according to ACR criteria; CDAI, Clinical Disease Activity Index; CRP, C-reactive protein; DAS28, Disease Activity Score in 28 joints; ESR, erythrocyte sedimentation rate; HAQ-DI, Health Assessment Questionnaire Disability Index; IL-6, interleukin-6; LDA, low disease activity; MTX, methotrexate
*in MOBILITY HAQ-DI was measured at week 16

FIG. 11B

| MOBILITY n (%) | Low IL-6 tertile | | | Medium IL-6 tertile | | | High IL-6 tertile | | |
|---|---|---|---|---|---|---|---|---|---|
| | Placebo + MTX (n=143) | Sarilumab 150 mg q2w + MTX (n=128) | Sarilumab 200 mg q2w + MTX (n=128) | Placebo + MTX (n=122) | Sarilumab 150 mg q2w + MTX (n=129) | Sarilumab 200 mg q2w + MTX (n=147) | Placebo + MTX (n=133) | Sarilumab 150 mg q2w + MTX (n=146) | Sarilumab 200 mg q2w + MTX (n=121) |
| Any AE | 87 (60.8) | 92 (73.0) | 101 (78.9) | 74 (60.7) | 98 (76.0) | 117 (79.6) | 84 (64.1) | 110 (75.3) | 94 (77.7) |
| Any SAE | 10 (7.0) | 9 (7.1) | 14 (10.9) | 5 (4.1) | 19 (14.7) | 19 (12.9) | 6 (4.6) | 9 (6.2) | 12 (9.9) |
| Any AE leading to death | 0 | 1 (0.8) | 1 (0.8) | 0 | 1 (0.8) | 0 | 2 (1.5) | 0 | 0 |
| Any AE leading to permanent treatment discontinuation | 5 (3.5) | 13 (10.3) | 17 (13.3) | 6 (4.9) | 22 (17.1) | 21 (14.3) | 9 (6.9) | 16 (11.0) | 16 (13.2) |

| MONARCH n (%) | Low IL-6 tertile | | Medium IL-6 tertile | | High IL-6 tertile | |
|---|---|---|---|---|---|---|
| | Adalimumab 40 mg q2w (n=45) | Sarilumab 200 mg q2w (n=55) | Adalimumab 40 mg q2w (n=53) | Sarilumab 200 mg q2w (n=47) | Adalimumab 40 mg q2w (n=54) | Sarilumab 200 mg q2w (n=46) |
| Any AE | 31 (68.9) | 33 (60.0) | 30 (56.6) | 30 (63.8) | 35 (64.8) | 33 (71.7) |
| Any SAE | 3 (6.7) | 2 (3.6) | 1 (1.9) | 3 (6.4) | 5 (9.3) | 1 (2.2) |
| Any AE leading to death | 0 | 0 | 0 | 1 (2.1) | 0 | 0 |
| Any AE leading to permanent treatment discontinuation | 6 (13.3) | 2 (3.6) | 2 (3.8) | 4 (8.5) | 4 (7.4) | 2 (4.3) |

AE, adverse event; SAE, serious adverse event

IL-6, interleukin-6; MTX, methotrexate; q2w, every 2 weeks; SAE, serious adverse event; TEAE, treatment-emergent adverse event

FIG. 12

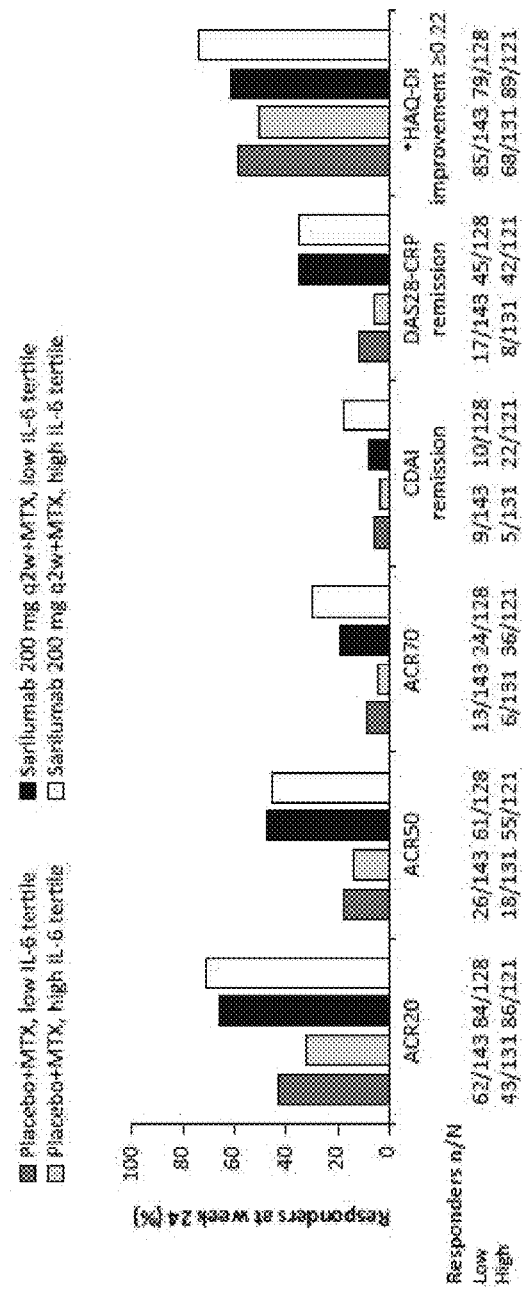
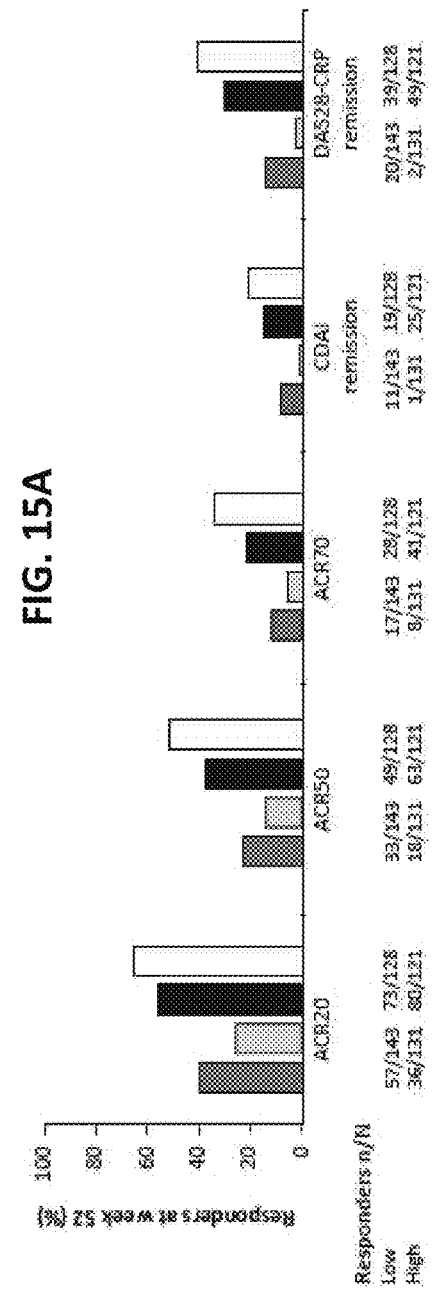
FIG. 15A
FIG. 15B

SEQUENCE LISTING

<160> NUMBER OF SEQ ID NOS: 251

<210> SEQ ID NO 1
<211> LENGTH: 358
<212> TYPE: PRT
<213> ORGANISM: Homo sapiens

<400> SEQUENCE: 1

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp
        355

<210> SEQ ID NO 2
<211> LENGTH: 379
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaagtgcagc tggtggagtc tgggggaaac ttggtacagc ctggcaggtc cctgagactc      60
tcctgtgcag cctctggatt catctttgat gattatgcca tgcactgggt ccggcaagct     120
ccagggaagg gcctggagtg gtctcaggt attagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaagatgga     300
ggcagcagct ggttaccgtt cgtctactac tacggtatgg acgtctgggg ccaagggacc     360
acggtcaccg tctcgtcag                                                  379

<210> SEQ ID NO 3
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Asn Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Gly Ser Ser Trp Leu Pro Phe Val Tyr Tyr Tyr Gly
            100                 105                 110

Met Asp Val Trp Gly Gln Gly Thr Thr Val Thr Val Ser Ser
        115                 120                 125

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggattcatct ttgatgatta tgcc                                             24

<210> SEQ ID NO 5
<211> LENGTH: 8
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 5

Gly Phe Ile Phe Asp Asp Tyr Ala
1               5

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
attagttgga atagtggtag cata                                          24

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Ile Ser Trp Asn Ser Gly Ser Ile
1               5

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
gcaaaagatg gaggcagcag ctggttaccg ttcgtctact actacggtat ggacgtc      57

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Ala Lys Asp Gly Gly Ser Ser Trp Leu Pro Phe Val Tyr Tyr Tyr Gly
1               5                   10                  15

Met Asp Val

<210> SEQ ID NO 10
<211> LENGTH: 325
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
gaaatagtga tgacgcagtc tccagccacc ctgtctgtgt ctcccgggga aagagccacc    60
ctctcctgca gggccagtca gagtattagc agcaactttg cctggtacca gcagaaacct   120

```
ggccaggctc ccaggctcct catctatggt gcatccacca gggccactgg tatcccagcc    180
aggttcagtg gcagtgggtc tgggacagac ttcactctca ccatcagcag cctgcagtct    240
gaagattttg cagtttatta ctgtcagcag tatagtagct ggcctccgta cacttttggc    300
caggggacca agctggagat caaac                                          325
```

```
<210> SEQ ID NO 11
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Phe Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Ser Ser Trp Pro Pro
                85                  90                  95

Tyr Thr Phe Gly Gln Gly Thr Lys Leu Glu Ile Lys
            100                 105
```

```
<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cagagtatta gcagcaac                                                   18
```

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Ile Ser Ser Asn
1               5
```

```
<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 ggtgcatcc                                                              9
```

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ala Ser
1

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cagcagtata gtagctggcc tccgtacact                                      30

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln Tyr Ser Ser Trp Pro Pro Tyr Thr
1               5                   10

<210> SEQ ID NO 18
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gaagtgcagc tggtggagtc tgggggaggc ttggttcagc ctggcaggtc cctgagactc      60
tcctgtgcag cctctagatt tacctttgat gattatgcca tgcactgggt ccggcaagct     120
ccagggaagg gcctggagtg ggtctcaggt attagttgga atagtggtag aataggttat     180
gcggactctg tgaagggccg attcaccatc tccagagaca acgccgagaa ctccctcttt     240
ctgcaaatga acgtctgag agcagaggac acggccttgt attactgtgc aaaaggccga     300
gattcttttg atatctgggg ccaagggaca atggtcaccg tctcttcag                 349

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Arg
1               5                   10                  15

```
Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
        115
```

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agatttacct tgatgatta tgcc                                         24

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Phe Thr Phe Asp Asp Tyr Ala
1               5

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
attagttgga atagtggtag aata                                        24

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Ser Trp Asn Ser Gly Arg Ile
1               5

<210> SEQ ID NO 24
<211> LENGTH: 27
<212> TYPE: DNA

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      oligonucleotide

<400> SEQUENCE: 24
gcaaaaggcc gagattctttt tgatatc                                          27

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Lys Gly Arg Asp Ser Phe Asp Ile
1               5

<210> SEQ ID NO 26
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gacatccaga tgacccagtc tccatcttcc gtgtctgcat ctgtaggaga cagagtcacc         60
atcacttgtc gggcgagtca gggtattagc agctggttag cctggtatca gcagaaacca       120
gggaaagccc ctaagctcct gatctatggt gcatccagtt tggaaagtgg ggtcccatca       180
aggttcagcg gcagtggatc tgggacagat ttcactctca ccatcagcag cctgcagcct       240
gaagattttg caagttatta ttgtcaacag gctaacagtt tcccgtacac ttttggccag       300
gggaccaagc tggagatcaa ac                                                322

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys
            100                 105

```
<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cagggtatta gcagctgg                                                   18

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gly Ile Ser Ser Trp
1               5

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 ggtgcatcc                                                              9

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ala Ser
1

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
caacaggcta acagtttccc gtacact                                         27

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Ala Asn Ser Phe Pro Tyr Thr
1               5
```

<210> SEQ ID NO 34
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caggttcagc tggtgcagtc tggagctgag ctgaagaagc ctggggcctc agtgaaggtc      60
tcctgcaagg cttctggtta cactttacc cattatggta tcagctgggt gcgacaggcc     120
cctggacaag ggcttgagtg gatgggatgg atcagcgctt acaatgatga cacaaactat     180
gcacagaagt tccaggggag agtcaccatg accacagaca catccacgag cacagcctac     240
atggagctga ggagcctgag atctgacgac acggccgttt attactgtgc gagagaagcg     300
cagctcgtcc tctactacta ctacggtatg gacgtctggg gccaagggac cacggtcacc     360
gtctcctcag                                                           370

<210> SEQ ID NO 35
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr His Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asp Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gln Leu Val Leu Tyr Tyr Tyr Gly Met Asp Val
            100                 105                 110

Trp Gly Gln Gly Thr Thr Val Thr Val Ser Ser
        115                 120

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggttacactt ttacccatta tggt                                            24

<210> SEQ ID NO 37
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 37

Gly Tyr Thr Phe Thr His Tyr Gly
1               5

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atcagcgctt acaatgatga caca                                           24

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Ser Ala Tyr Asn Asp Asp Thr
1               5

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcgagagaag cgcagctcgt cctctactac tactacggta tggacgtc                 48

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Arg Glu Ala Gln Leu Val Leu Tyr Tyr Tyr Tyr Gly Met Asp Val
1               5                   10                  15

<210> SEQ ID NO 42
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gaaattgtgt tgacacagtc tccagccacc ctgtctttgt ctccagggga aagagccacc    60
ctctcctgca gggccagtca gagtgttagc agcttcttag cctggaacca acagaaacct   120
ggccaggctc ccaggctcct catctatgat gcatccaaca gggccactgg catcccagcc   180
```

-continued

```
aggttcagtg gcagtgggtc tgggacagac ttcactctca ccatcagcag cctagagcct      240
gaagattttg cagtttatta ctgccagcag cgtaacaatt ggccgtacat ttttggccag      300
gggaccaagc tggagatcag ac                                               322
```

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Asn Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Tyr
                85                  90                  95

Ile Phe Gly Gln Gly Thr Lys Leu Glu Ile Arg
            100                 105

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 44

```
cagagtgtta gcagcttc                                                    18
```

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 45

Gln Ser Val Ser Ser Phe
1               5

<210> SEQ ID NO 46
<211> LENGTH: 9
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 46

```
gatgcatcc                                                               9
```

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Ala Ser
1

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cagcagcgta acaattggcc gtacatt                                         27

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Gln Arg Asn Asn Trp Pro Tyr Ile
1               5

<210> SEQ ID NO 50
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
caggttcagc tggtgcagtc tggagctgag gtgaagaagc ctggggcctc agtgaaggtc     60
tcctgcaagg cttctggtta cacctttacc agttatggta tcagctgggt gcgacaggcc    120
cctggacaag ggcttgagtg gatgggatgg atcagcgctt acaatgatga cacaaactat    180
gcacagaagt tccaggggag agtcaccatg accacagaca catccacgag cacagcctac    240
atggagctga ggagcctgag atctgacgac acggccgttt attactgtgc gagagaagcg    300
cagctcgtcc tctactacta ctacggtatg gacgtctggg gccaagggac cacggtcacc    360
gtctcctcag                                                           370

<210> SEQ ID NO 51
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asp Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gln Leu Val Leu Tyr Tyr Tyr Tyr Gly Met Asp Val
            100                 105                 110

Trp Gly Gln Gly Thr Thr Val Thr Val Ser Ser
        115                 120

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggttacacct ttaccagtta tggt                                              24

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Tyr Thr Phe Thr Ser Tyr Gly
1               5

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atcagcgctt acaatgatga caca                                              24

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Ser Ala Tyr Asn Asp Asp Thr
1               5

<210> SEQ ID NO 56
<211> LENGTH: 48

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gcgagagaag cgcagctcgt cctctactac tactacggta tggacgtc         48

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Arg Glu Ala Gln Leu Val Leu Tyr Tyr Tyr Tyr Gly Met Asp Val
1               5                   10                  15

<210> SEQ ID NO 58
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gaaattgtgt tgacacagtc tccagccacc ctgtctttgt ctccagggga aagagccacc    60
ctctcctgca gggccagtca gagtgttagc agcttcttag cctggaacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgccagcag cgtagcaatt ggccgtacat ttttggccag   300
gggaccaagc tggagatcaa ac                                            322

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
                20                  25                  30

Leu Ala Trp Asn Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Ile Phe Gly Gln Gly Thr Lys Leu Glu Ile Lys
            100                 105

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cagagtgtta gcagcttc                                                 18

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ser Val Ser Ser Phe
1               5

<210> SEQ ID NO 62
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62 gatgcatcc                                                            9

<210> SEQ ID NO 63
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Ala Ser
1

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cagcagcgta gcaattggcc gtacatt                                       27

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Arg Ser Asn Trp Pro Tyr Ile

<210> SEQ ID NO 66
<211> LENGTH: 349
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
gaagtgcagc tggtggagtc tgggggaggc ttggtacagc ctggcaggtc cctgagactc      60
tcctgtgcag cctctggatt cacctttgat gattatgccc tgcactgggt ccggcaagct     120
ccagggaagg gcctggagtg ggtctcaggt gttagttgga atggtggtag aataggctat     180
gcggactctg tgaaaggccg attcaccatc tccagagaca acgccaagaa ctccctcttt     240
ctgcaaatga acagtctgag agttgaggac acggccttgt attattgtgc aaaaggccgg     300
gatgcttttg atatctgggg ccaagggaca ttggtcaccg tctcttcag                 349
```

<210> SEQ ID NO 67
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Leu Tyr Tyr Cys
                85                  90                  95

Ala Lys Gly Arg Asp Ala Phe Asp Ile Trp Gly Gln Gly Thr Leu Val
            100                 105                 110

Thr Val Ser Ser
        115

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68

```
ggattcacct ttgatgatta tgcc                                              24
```

<210> SEQ ID NO 69
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 69

Gly Phe Thr Phe Asp Asp Tyr Ala
1               5

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gttagttgga atggtggtag aata                                          24

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Ser Trp Asn Gly Gly Arg Ile
1               5

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gcaaaaggcc gggatgcttt tgatatc                                       27

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Lys Gly Arg Asp Ala Phe Asp Ile
1               5

<210> SEQ ID NO 74
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
gaaattgtgt tgacacagtc tccagccacc ctgtctttgt ctccagggga aagagccacc    60
ctctcctgca gggccagtca gagtgttagc agttacttag cctggtacca acagaaacct   120
ggccaggctc ccaggctcct catctatgat gcatccaaca gggccactgg catcccagcc   180
```

```
aggttcagtg gcagtgggtc tgggacagac ttcactctca ccatcagcag cctagagcct    240
gaagattttg catttttatta ctgtcagcag cgtaacaacc ggcctccatt cactttcggc    300
cctgggacca aagtggatgt cagac                                          325
```

<210> SEQ ID NO 75
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105
```

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76

```
cagagtgtta gcagttac                                                   18
```

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Gln Ser Val Ser Ser Tyr
1               5
```

<210> SEQ ID NO 78
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78

```
gatgcatcc                                                              9
```

<210> SEQ ID NO 79
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Ala Ser
1

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cagcagcgta acaaccggcc tccattcact                                         30

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Gln Arg Asn Asn Arg Pro Pro Phe Thr
1               5                   10

<210> SEQ ID NO 82
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
caggttcagc tggtgcagtc tggagctgag gtgaagaagc ctggggcctc agtgaaggtc        60
tcctgtaagg cttctggttt caacttcttt cattatggta tcacctgggt gcgacaggcc       120
cctggacaag ggcttgagtg gatgggatgg atcagcactt acaatggtga cacaatctat       180
gcacagaagt tccagggcag agtcaccatg accacagaca cagccacgag cacggcctat       240
atggaactga ggagcctgag atctgacgac acggccgtgt attactgtgc gagatcggaa       300
cagcaggtgg actactactt ctacggtatg gacgtctggg gccaagggac cacggtcacc       360
gtttcctcag                                                             370

<210> SEQ ID NO 83
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Gln Ser Gly Ala Glu Val Lys Lys Pro Gly Ala
1               5                   10                  15

-continued

```
Ser Val Lys Val Ser Cys Lys Ala Ser Gly Phe Asn Phe Phe His Tyr
            20                  25                  30
Gly Ile Thr Trp Val Arg Gln Ala Pro Gly Gln Gly Leu Glu Trp Met
        35                  40                  45
Gly Trp Ile Ser Thr Tyr Asn Gly Asp Thr Ile Tyr Ala Gln Lys Val
 50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                85                  90                  95
Ala Arg Ser Glu Gln Gln Val Asp Tyr Tyr Pro Tyr Gly Met Asp Val
            100                 105                 110
Trp Gly Gln Gly Thr Thr Val Thr Val Ser Ser
        115                 120
```

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggtttcaact tctttcatta tggt                                          24

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Phe Asn Phe Phe His Tyr Gly
1               5

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
atcagcactt acaatggtga caca                                          24

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ile Ser Thr Tyr Asn Gly Asp Thr
1               5

<210> SEQ ID NO 88
<211> LENGTH: 48
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 88
gcgagatcgg aacagcaggt ggactactac ttctacggta tggacgtc              48

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Arg Ser Glu Gln Gln Val Asp Tyr Tyr Phe Tyr Gly Met Asp Val
1               5                   10                  15

<210> SEQ ID NO 90
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
gaaattgtgt tgacacagtc tccagccacc ctgtctttgt ctccagggga aagagccacc    60
ctctcctgca gggccagtca gagtgttagc agttacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg catttattac tgtcagcag cgtaacaacc ggcctccatt cactttcggc   300
cctgggacca agtggatgt cagac                                         325

<210> SEQ ID NO 91
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105
```

```
<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cagagtgtta gcagttac                                                   18

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Ser Val Ser Ser Tyr
1               5

<210> SEQ ID NO 94
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94 gatgcatcc                                                              9

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Ala Ser
1

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cagcagcgta acaaccggcc tccattcact                                      30

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Arg Asn Asn Arg Pro Pro Phe Thr
1               5                   10
```

<210> SEQ ID NO 98
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
caggttcagc tggtgcagtc tggagctgag gtgaagaagc ctggggcctc agtgaaggtc        60
tcctgtaagg cttctggttt caacttcttt cattatggta tcacctgggt gcgacaggcc       120
cctggacaag ggcttgagtg gatgggatgg atcagcactt acaatggtga cacaatctat       180
gcacagaagg tccagggcag agtcaccatg accacagaca cagccacgag cacggcctat       240
atggaactga ggagcctgag atctgacgac acggccgtgt attactgtgc gagatcggaa       300
cagcaggtgg actactactt ctacggtatg gacgtctggg gccaagggac cacggtcacc       360
gtttcctcag                                                              370

<210> SEQ ID NO 99
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Phe His Tyr
            20                  25                  30

Gly Ile Thr Trp Val Arg Gln Ala Pro Gly Gln Gly Leu Glu Trp Met
        35                  40                  45

Gly Trp Ile Ser Thr Tyr Asn Gly Asp Thr Ile Tyr Ala Gln Lys Val
    50                  55                  60

Gln Gly Arg Val Thr Met Thr Thr Asp Thr Ala Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Glu Gln Gln Val Asp Tyr Tyr Phe Tyr Gly Met Asp Val
            100                 105                 110

Trp Gly Gln Gly Thr Thr Val Thr Val Ser Ser
        115                 120

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggtttcaact tctttcatta tggt                                               24

<210> SEQ ID NO 101
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 101

Gly Phe Asn Phe Phe His Tyr Gly
1               5

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atcagcactt acaatggtga caca                                          24

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Ser Thr Tyr Asn Gly Asp Thr
1               5

<210> SEQ ID NO 104
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gcgagatcgg aacagcaggt ggactactac ttctacggta tggacgtc                48

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Arg Ser Glu Gln Gln Val Asp Tyr Tyr Phe Tyr Gly Met Asp Val
1               5                   10                  15

<210> SEQ ID NO 106
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gaaattgtgt tgacacagtc tccagccacc ctgtctttgt ctccagggga aagagccacc    60
ctctcctgca gggccagtca gagtgttagc agttacttag cctggtacca acagaaacct   120
ggccaggctc ccaggctcct catctatgat gcatccaaca gggccactgg catcccagcc   180
```

```
aggttcagtg gcagtgggtc tgggacagac ttcactctca ccatcagcag cctagagcct    240
gaagattttg catttatta ctgtcagcag cgtaacaacc ggcctccatt cactttcggc     300
cctgggacca aagtggatgt cagac                                          325
```

<210> SEQ ID NO 107
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 107

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Asn Asn Arg Pro Pro
                85                  90                  95

Phe Thr Phe Gly Pro Gly Thr Lys Val Asp Val Arg
            100                 105
```

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 108

```
cagagtgtta gcagttac                                                   18
```

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 109

```
Gln Ser Val Ser Ser Tyr
1               5
```

<210> SEQ ID NO 110
<211> LENGTH: 9
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 110

```
gatgcatcc                                                              9
```

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Ala Ser
1

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cagcagcgta acaaccggcc tccattcact                                     30

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Gln Arg Asn Asn Arg Pro Pro Phe Thr
1               5                   10

<210> SEQ ID NO 114
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
caggtgcagc tggtgcagtc tggggctgag gtgaaagagc ctggggcctc agtgaagatc     60
tcctgcaagg cttctggata caccttcacc tcttatgata tcatctgggt gcgacaggcc    120
actggacaag ggcttgagtg gatgggatgg atgaacccaa acagtggtga cagaggctat    180
acacagaacc tccagggcag agtcaccttg accagggaca cctccataag tacagtctac    240
atggaactga gcagcctgag atctgaggac acggccgtat attattgtgc gcgagactac    300
agtaaccact actacggttt ggacgtctgg ggccaaggga ccacggtcac tgtctcctca    360
g                                                                   361

<210> SEQ ID NO 115
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Val Gln Ser Gly Ala Glu Val Lys Glu Pro Gly Ala
1               5                   10                  15

Ser Val Lys Ile Ser Cys Lys Ala Ser Gly Tyr Thr Phe Thr Ser Tyr
            20                  25                  30

Asp Ile Ile Trp Val Arg Gln Ala Thr Gly Gln Gly Leu Glu Trp Met
        35                  40                  45

Gly Trp Met Asn Pro Asn Ser Gly Asp Arg Gly Tyr Thr Gln Asn Leu
    50                  55                  60

Gln Gly Arg Val Thr Leu Thr Arg Asp Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asn His Tyr Tyr Gly Leu Asp Val Trp Gly Gln
            100                 105                 110

Gly Thr Thr Val Thr Val Ser Ser
        115                 120

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggatacacct tcacctctta tgat                                              24

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Tyr Thr Phe Thr Ser Tyr Asp
1               5

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atgaacccaa acagtggtga caga                                              24

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Met Asn Pro Asn Ser Gly Asp Arg
1               5

<210> SEQ ID NO 120
<211> LENGTH: 39

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gcgcgagact acagtaacca ctactacggt ttggacgtc                             39

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Arg Asp Tyr Ser Asn His Tyr Tyr Gly Leu Asp Val
1               5                   10

<210> SEQ ID NO 122
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
gacatccagt tgacccagtc tccatccttc ctgtctgcat ctgtaggaga cagagtcacc      60
atcacttgct gggccagtca ggacattagc aattatttag cctggtatca gcaaaaacca    120
gggaaagccc ctaagctcct gatctttgtt gcatccactt tgcagagtgg ggtcccatca    180
aggttcagcg gcagtggatc tgggacagaa ttcactctca caatcagtag cctgcagcct    240
gaagattttg caacttatta ctgtcaacag tttaatagtt acccgctcac tttcggcgga    300
gggaccaagg tggagatcag ac                                             322

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Phe Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Arg
            100                 105

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
caggacatta gcaattat                                                      18

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Asp Ile Ser Asn Tyr
1               5

<210> SEQ ID NO 126
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126 gttgcatcc                                                                 9

<210> SEQ ID NO 127
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Ala Ser
1

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
caacagttta atagttaccc gctcactttc                                         30

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Phe Asn Ser Tyr Pro Leu Thr

<210> SEQ ID NO 130
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
caggttcagc tggtgcagtc tggagctgag gtgaagaagc ctggggcctc agtgaaggtc        60
tcctgcaagg cttctggtta cacctttacc agttatggta tcagctgggt gcgacaggcc       120
cctggacaag gcttgagtg atgggatgg atcagcgctt acaatgatga cacaaactat         180
gcacagaagt tccaggggag agtcaccatg accacagaca catccacgag cacagcctac       240
atggagctga ggagcctgag atctgacgac acggccgttt attactgtgc gagagaagcg       300
cagctcgtcc tctactacta ctacggtatg gacgtctggg gccaagggac cacggtcacc       360
gtctcctcag                                                              370

<210> SEQ ID NO 131
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asp Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Gln Leu Val Leu Tyr Tyr Tyr Gly Met Asp Val
            100                 105                 110

Trp Gly Gln Gly Thr Thr Val Thr Val Ser Ser
        115                 120

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggttacacct ttaccagtta tggt                                               24

<210> SEQ ID NO 133
<211> LENGTH: 8
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 133

Gly Tyr Thr Phe Thr Ser Tyr Gly
1               5

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
atcagcgctt acaatgatga caca                                          24

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ile Ser Ala Tyr Asn Asp Asp Thr
1               5

<210> SEQ ID NO 136
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gcgagagaag cgcagctcgt cctctactac tactacggta tggacgtc                48

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Arg Glu Ala Gln Leu Val Leu Tyr Tyr Tyr Tyr Gly Met Asp Val
1               5                   10                  15

<210> SEQ ID NO 138
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gaaattgtgt tgacacagtc tccagccacc ctgtctttgt ctccagggga aagagccacc    60
ctctcctgca gggccagtca gagtgttagc agcttcttag cctggaacca acagaaacct   120

```
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgccagcag cgtagcaatt ggccgtacat ttttggccag    300
gggaccaagc tggagatcaa ac                                              322
```

<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Asn Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Ile Phe Gly Gln Gly Thr Lys Leu Glu Ile Lys
            100                 105

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140

```
cagagtgtta gcagcttc                                                   18
```

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Ser Val Ser Ser Phe
1               5

<210> SEQ ID NO 142
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142

```
gatgcatcc                                                              9
```

<210> SEQ ID NO 143
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Ala Ser
1

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
cagcagcgta gcaattggcc gtacatt                                              27

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Gln Arg Ser Asn Trp Pro Tyr Ile
1               5

<210> SEQ ID NO 146
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
gaagtgcagc tggtggagtc tgggggaggc ttggtacagc ctggcaggtc cctgagactc          60
tcctgtgcag cctctggatt cacctttgat gattatgccc tgcactgggt ccggcaagct         120
ccagggaagg gcctggagtg ggtctcaggt gttagttgga atggtggtag aataggctat         180
gcggactctg tgaaaggccg attcaccatc tccagagaca acgccaagaa ctccctcttt         240
ctgcaaatga acagtctgag agttgaggac acggccttgt attattgtgc aaaaggccgg         300
gatgcttttg atatctgggg ccaagggaca ttggtcaccg tctcttcag                     349

<210> SEQ ID NO 147
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
 50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Leu Tyr Tyr Cys
                85                  90                  95

Ala Lys Gly Arg Asp Ala Phe Asp Ile Trp Gly Gln Gly Thr Leu Val
            100                 105                 110

Thr Val Ser Ser
        115

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggattcacct ttgatgatta tgcc                                              24

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Phe Thr Phe Asp Asp Tyr Ala
1               5

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gttagttgga atggtggtag aata                                              24

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Val Ser Trp Asn Gly Gly Arg Ile
1               5

<210> SEQ ID NO 152
<211> LENGTH: 27
<212> TYPE: DNA

<210> SEQ ID NO 152
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
gcaaaaggcc gggatgcttt tgatatc    27

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Ala Lys Gly Arg Asp Ala Phe Asp Ile
1               5

<210> SEQ ID NO 154
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaaactcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacat gcttacagtt cccgtacac ttttggccag    300
gggaccaagc tggagatcaa ac                                             322

<210> SEQ ID NO 155
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ala Tyr Ser Phe Pro Tyr
                85                  90                  95

Thr Phe Gly Gln Gly Thr Lys Leu Glu Ile Lys
            100                 105

```
<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cagggtatta gcagctgg                                                       18

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Gly Ile Ser Ser Trp
1               5

<210> SEQ ID NO 158
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158 gctgcatcc                                                                  9

<210> SEQ ID NO 159
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Ala Ser
1

<210> SEQ ID NO 160
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
caacatgctt acagtttccc gtacact                                             27

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln His Ala Tyr Ser Phe Pro Tyr Thr
1               5
```

<210> SEQ ID NO 162
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
gaagtgcagc tggtggagtc tgggggaggc ttggtacagc ctggcaggtc cctgagactc      60
tcctgtgcag cctctggatt cacctttgat gattatgcct tgcactgggt ccggcaagct     120
ccagggaagg gcctggagtg gtctcaggt attagttgga acagtggtag aataggctat      180
gcggactctg tgaagggccg attcaccatt tccagagaca cgccaagaa ctccctcttt      240 ctgcaaatga acagtctgag agctgaggac acggccttgt attattgtgc aaaaggccgg     300
gatgcttttg atatctgggg ccaagggaca ttggtcaccg tctcttcag                 349

<210> SEQ ID NO 163
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Leu Tyr Tyr Cys
                85                  90                  95

Ala Lys Gly Arg Asp Ala Phe Asp Ile Trp Gly Gln Gly Thr Leu Val
            100                 105                 110

Thr Val Ser Ser
        115

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ggattcacct ttgatgatta tgcc                                             24

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Gly Phe Thr Phe Asp Asp Tyr Ala
1               5

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
attagttgga acagtggtag aata                                           24

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ile Ser Trp Asn Ser Gly Arg Ile
1               5

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gcaaaaggcc gggatgcttt tgatatc                                        27

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Lys Gly Arg Asp Ala Phe Asp Ile
1               5

<210> SEQ ID NO 170
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
gacatccaga tgacccagtc tccatcttcc gtgtctgcat ctgtaggaga cagagtcacc      60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240

```
gaagattttg caacttacta ttgtcaacag gctaacagtt tcccgtacac ttttggccag    300
gggaccaagc tggagatcaa ac                                             322
```

<210> SEQ ID NO 171
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Tyr
                 85                  90                  95

Thr Phe Gly Gln Gly Thr Lys Leu Glu Ile Lys
            100                 105
```

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172

```
cagggtatta gcagctgg                                                   18
```

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

```
Gln Gly Ile Ser Ser Trp
  1               5
```

<210> SEQ ID NO 174
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174

```
gctgcatcc                                                              9
```

<210> SEQ ID NO 175

-continued

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Ala Ser
1

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
caacaggcta acagtttccc gtacact                                         27

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Gln Ala Asn Ser Phe Pro Tyr Thr
1               5

<210> SEQ ID NO 178
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
caggtgcagc tggtgcagtc tggggctgag gtgaaagagc ctggggcctc agtgaaggtc      60
tcctgcaagg cttctggata caccttcacc tcttatgata tcatctgggt gcgacaggcc    120
actggacaag gcttgagtg gatgggatgg atgaacccaa acagtggtaa cacaggctat     180
acacagaacc tccagggcag agtcaccttg accaggaaca cctccataac tacagtctac    240
atggaactga gcagcctgag ctctgaggac acggccgttt attactgtgc gcgagactac    300
agtagccact actacggttt ggacgtctgg ggccaaggga ccacggtcac cgtctcctca    360
a                                                                   361

<210> SEQ ID NO 179
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Ala Glu Val Lys Glu Pro Gly Ala
1               5                   10                  15

Ser Val Lys Val Ser Cys Lys Ala Ser Gly Tyr Thr Phe Thr Ser Tyr
```

```
            20                  25                  30
Asp Ile Ile Trp Val Arg Gln Ala Thr Gly Gln Gly Leu Glu Trp Met
        35                  40                  45

Gly Trp Met Asn Pro Asn Ser Gly Asn Thr Gly Tyr Thr Gln Asn Leu
 50                  55                  60

Gln Gly Arg Val Thr Leu Thr Arg Asn Thr Ser Ile Thr Thr Val Tyr
 65                  70                  75                  80

Met Glu Leu Ser Ser Leu Ser Ser Glu Asp Thr Ala Val Tyr Tyr Cys
                85                  90                  95

Ala Arg Asp Tyr Ser Ser His Tyr Tyr Gly Leu Asp Val Trp Gly Gln
                100                 105                 110

Gly Thr Thr Val Thr Val Ser Ser
            115                 120

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ggatacacct tcacctctta tgat                                          24

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Tyr Thr Phe Thr Ser Tyr Asp
 1               5

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atgaacccaa acagtggtaa caca                                          24

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Met Asn Pro Asn Ser Gly Asn Thr
 1               5

<210> SEQ ID NO 184
<211> LENGTH: 39
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 184
gcgcgagact acagtagcca ctactacggt ttggacgtc                             39

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Arg Asp Tyr Ser Ser His Tyr Tyr Gly Leu Asp Val
1               5                   10

<210> SEQ ID NO 186
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
gacatccagt tgacccagtc tccatccttc ctgtctacat ctataggaga cagagtcacc      60
atcacttgct gggccagtca ggacattagc aattatttag cctggtatca gcaaaaacca     120
gggaaagccc ctaagctcct gatctttgtt gcatccactt tgcagagtgg ggtcccatca     180
aggttcagcg gcagtggatc tgggacagaa ttcactctca caatcagtag cctgcagcct     240
gaggattttg caacttatta ctgtcaacag tttaatagtt acccgctcac tttcggcgga     300
gggaccaagg tggaaatcaa ac                                              322

<210> SEQ ID NO 187
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Gln Leu Thr Gln Ser Pro Ser Phe Leu Ser Thr Ser Ile Gly
1               5                   10                  15

Asp Arg Val Thr Ile Thr Cys Trp Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Phe Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 188

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
caggacatta gcaattat                                                 18

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Asp Ile Ser Asn Tyr
1               5

<210> SEQ ID NO 190
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190 gttgcatcc                                                            9

<210> SEQ ID NO 191
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Val Ala Ser
1

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
caacagttta atagttaccc gctcactttc                                    30

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Gln Phe Asn Ser Tyr Pro Leu Thr Phe
1               5                   10
```

<210> SEQ ID NO 194
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
caggtccagc tggtgcagtc tgggggagac ttggtacagc ccggcaggtc cctgagactc        60
tcctgtgcag cctctggatt cacctttgat gattatgcca tgcactgggt ccggcaaact       120
ccagggaagg gcctggagtg ggtctcaggt attagttgga atagtggggc cataggctat       180
gcggactctg tgaagggccg attcaccatc tccagagaca acgccaagaa ctccctgtat       240
ctgcaaatga acagtctgag agctgaggac acggccttgt attactgtac aaaagaagaa       300
gtgggagcta cggtggatta tttctacttc tacggtatgg acgtctgggg ccaagggacc       360
acggtcaccg tctcctca                                                     378

<210> SEQ ID NO 195
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gln Val Gln Leu Val Gln Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Ala Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Glu Glu Val Gly Ala Thr Val Asp Tyr Phe Tyr Phe Tyr Gly
            100                 105                 110

Met Asp Val Trp Gly Gln Gly Thr Thr Val Thr Val Ser Ser
        115                 120                 125

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ggattcacct ttgatgatta tgcc                                               24

<210> SEQ ID NO 197
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 197

Gly Phe Thr Phe Asp Asp Tyr Ala
1               5

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
attagttgga atagtggggc cata                                          24

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ile Ser Trp Asn Ser Gly Ala Ile
1               5

<210> SEQ ID NO 200
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
acaaaagaag aagtgggagc tacggtggat tatttctact tctacggtat ggacgtc     57

<210> SEQ ID NO 201
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Thr Lys Glu Glu Val Gly Ala Thr Val Asp Tyr Phe Tyr Phe Tyr Gly
1               5                   10                  15

Met Asp Val

<210> SEQ ID NO 202
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
gaaattgtga tgactcagtc tccagccacc ctgtctttgt ctccagggga aagagccacc     60
ctctcctgct gggccagtca gagtgttagc aactacttag cctggtacca acagaaacct    120

```
ggccaggctc ccagactcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagcaact ggcctacgtt cggccaaggg      300
accaaggtgg aaatcaaa                                                    318
```

<210> SEQ ID NO 203
<211> LENGTH: 106
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 203

```
Glu Ile Val Met Thr Gln Ser Pro Ala Thr Leu Ser Leu Ser Pro Gly
1               5                   10                  15

Glu Arg Ala Thr Leu Ser Cys Trp Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 204
<211> LENGTH: 18
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 204

```
cagagtgtta gcaactac                                                    18
```

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 205

```
Gln Ser Val Ser Asn Tyr
1               5
```

<210> SEQ ID NO 206
<211> LENGTH: 9
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 206

```
gatgcatcc                                                               9
```

<210> SEQ ID NO 207
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asp Ala Ser
1

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
cagcagcgta gcaactggcc tacg                                           24

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Gln Arg Ser Asn Trp Pro Thr
1               5

<210> SEQ ID NO 210
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
caagtgcagc tggtgcagtc tgggggaggc ttggtacagc ctggcaggtc cctgagactc     60
tcctgtgcag cctctggatt cacctttgat gattatgcca tgcactgggt ccggcaagct    120
ccagggaagg gcctggagtg ggtctcaggt attagttgga atagtggtag ggtaggctat    180
gcggactctg tgaagggccg attcaccatc tccagagaca acgccaagaa ctccctgtat    240
ctgcaaatga acagtctgag agctgaggac acggccttgt attactgtac aaaaggccgg    300
gatgcttttg atatctgggg ccaggggaca atggtcaccg tctcttca                 348

<210> SEQ ID NO 211
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Val Gln Ser Gly Gly Gly Leu Val Gln Pro Gly Arg
1               5                   10                  15

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Gly Arg Asp Ala Phe Asp Ile Trp Gly Gln Gly Thr Met Val
            100                 105                 110

Thr Val Ser Ser
        115

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ggattcacct ttgatgatta tgcc                                           24

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Phe Thr Phe Asp Asp Tyr Ala
1               5

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
attagttgga atagtggtag ggta                                           24

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ile Ser Trp Asn Ser Gly Arg Val
1               5

<210> SEQ ID NO 216
<211> LENGTH: 27
<212> TYPE: DNA
```

<213> ORGANISM: Artificial Sequence
<220> FEATURE:
<223> OTHER INFORMATION: Description of Artificial Sequence: Synthetic
     oligonucleotide

<400> SEQUENCE: 216
acaaaaggcc gggatgcttt tgatatc                                      27

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 217

Thr Lys Gly Arg Asp Ala Phe Asp Ile
1               5

<210> SEQ ID NO 218
<211> LENGTH: 321
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 218
gatattgtga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccgtacac ttttggccag   300
gggaccaagc tggagatcaa a                                             321

<210> SEQ ID NO 219
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 219

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

```
<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
cagggtatta gcagctgg                                                  18

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Gly Ile Ser Ser Trp
1               5

<210> SEQ ID NO 222
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222 gctgcatcc                                                             9

<210> SEQ ID NO 223
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Ala Ser
1

<210> SEQ ID NO 224
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
caacaggcta acagtttccc gtacact                                        27

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gln Gln Ala Asn Ser Phe Pro Tyr Thr
1               5
```

<210> SEQ ID NO 226
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
gaagtgcagc tggtggaatc tggaggagga ctggtgcagc ctggaagatc tctgagactg    60
tcttgtgctg cttctggatt tatctttgat gattatgcta tgcattgggt gagacaggct   120
cctggaaagg gactggaatg ggtgtctgga atctcttgga attctggatc tatcggatat   180
gctgattctg tgaagggaag atttacaatc tctagagata atgctaagaa ttctctgtat   240
ctgcagatga attctctgag agctgaagat acagctctgt attattgtgc taaggatgga   300
ggatcttctt ggctgccttt tgtgtattat tatggaatgg atgtgtgggg acagggaaca   360
acagtgacag tgtcttct                                                  378

<210> SEQ ID NO 227
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Gly Ser Ser Trp Leu Pro Phe Val Tyr Tyr Tyr Gly
            100                 105                 110

Met Asp Val Trp Gly Gln Gly Thr Thr Val Thr Val Ser Ser
        115                 120                 125

<210> SEQ ID NO 228
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
gaaatcgtga tgacacagtc tcctgctaca ctgtctgtgt ctcctggaga aagagctaca    60
ctgtcttgta gagcttctca gtctatctct tctaatctgg cttggtatca gcagaagcct   120
ggacaggctc ctagactgct gatctatgga gcttctacaa gagctacagg aatccctgct   180
agattttctg gatctggatc tggaacagaa tttacactga caatctcttc tctgcagtct   240

```
gaagattttg ctgtgtatta ttgtcagcag tattcttctt ggcctcctta tacatttgga       300
cagggaacaa agctggaaat caag                                              324
```

<210> SEQ ID NO 229
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Trp Pro Pro
                85                  90                  95

Tyr Thr Phe Gly Gln Gly Thr Lys Leu Glu Ile Lys
            100                 105
```

<210> SEQ ID NO 230
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230

```
gaggtccagc tggtcgagtc aggaggaggc ctcgtccaac cagggcgcag ccttcgactc       60
tcctgtgccg ccagtaggtt tactttcgat gactatgcca tgcactgggt ccggcaggcc      120
cctggtaagg gcttggagtg ggtgtccggt atctcctgga actccggacg tatcggttac      180
gccgacagcg tgaagggaag gttcactatc tctcgtgaca acgccaagaa ctccttgtat      240
ctgcaaatga acagcctccg ggccgaagac accgccttgt attactgtgc caagggtagg      300
gatagtttcg atatctgggg tcaaggcacc atggtgactg tgtcttca                   348
```

<210> SEQ ID NO 231
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

```
Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45
```

```
Ser Gly Ile Ser Trp Asn Ser Gly Arg Ile Gly Tyr Ala Asp Ser Val
 50                  55                  60

Lys Gly Arg Phe Thr Ile Ser Arg Asp Asn Ala Glu Asn Ser Leu Phe
 65                  70                  75                  80

Leu Gln Met Asn Gly Leu Arg Ala Glu Asp Thr Ala Leu Tyr Tyr Cys
                 85                  90                  95

Ala Lys Gly Arg Asp Ser Phe Asp Ile Trp Gly Gln Gly Thr Met Val
            100                 105                 110

Thr Val Ser Ser
        115

<210> SEQ ID NO 232
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
gacatacaga tgacccaaag cccaagcagc gttagcgctt ccgtaggcga cagggtgaca      60
attacatgca gagcctctca gggaatttct tcatggctgg catggtatca gcagaagccc    120
ggaaaagctc ccaagctgct gatatatggt gcctcctctc tccaaagcgg agtcccatca    180
cgcttctccg ggagtggctc tggtacagat tttactttga caatctctag ccttcagcct    240
gaagactttg ctacatacta ctgtcagcag gccaacagtt ttccttacac cttcggtcag    300
ggaactaaac tggaaattaa g                                              321

<210> SEQ ID NO 233
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Gly Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Tyr
                 85                  90                  95

Thr Phe Gly Gln Gly Thr Lys Leu Glu Ile Lys
            100                 105

<210> SEQ ID NO 234
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 234

```
caggtgcagc tggtgcagtc tggagctgaa gtgaagaagc ctggagcttc tgtgaaggtg      60
tcttgtaagg cttctggata tacatttaca tcttatgata tcatctgggt gagacaggct     120
acaggacagg gactggaatg gatgggatgg atgaatccta attctggaaa tacaggatat     180
gctcagaagt ttcagggaag agtgacaatg acaagaaata catctatctc tacagtgtat     240
atggaactgt cttctctgag atctgaagat acagctgtgt attattgtgc tagagattat     300
tcttctcatt attatggact ggatgtgtgg ggacagggaa caacagtgac agtgtcttct     360
```

<210> SEQ ID NO 235
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ile Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Ser His Tyr Tyr Gly Leu Asp Val Trp Gly Gln
            100                 105                 110

Gly Thr Thr Val Thr Val Ser Ser
        115                 120
```

<210> SEQ ID NO 236
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236

```
gatatccagc tgacacagtc tccttctttt ctgtctgctt ctgtgggaga tagagtgaca      60
atcacatgta gagcttctca ggatatctct aattatctgg cttggtatca gcagaagcct     120
ggaaaggctc ctaagctgct gatctatgtg cttctacac tgcagtctgg agtgccttct      180 agatttctg gatctggatc tggaacagaa tttacactga caatctcttc tctgcagcct     240
gaagattttg ctacatatta ttgtcagcag tttaattctt atcctctgac atttggagga     300
ggaacaaagg tggaaatcaa g                                               321
```

<210> SEQ ID NO 237
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 237

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Val Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 238
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
gaagtgcagc tggtggagtc tgggggaggc ttggtacagc ctggcaggtc cctgagactc      60
tcctgtgcag cctctggatt cacctttgat gattatgccc tgcactgggt ccggcaagct    120
ccagggaagg gcctggagtg ggtctcaggt gttagttgga atggtggtag aataggctat    180
gcggactctg tgaaaggccg attcaccatc tccagagaca cgccaagaa ctccctcttt     240 ctgcaaatga acagtctgag agttgaggac acggccttgt attattgtgc aaaaggccgg    300
gatgcttttg atatctgggg ccaagggaca ttggtcaccg tctcttcag               349

<210> SEQ ID NO 239
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Val Ser Trp Asn Gly Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Val Glu Asp Thr Ala Leu Tyr Tyr Cys
                85                  90                  95

Ala Lys Gly Arg Asp Ala Phe Asp Ile Trp Gly Gln Gly Thr Met Val

<210> SEQ ID NO 240
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 240

```
gaagtgcagc tggtggaatc tggaggagga ctggtgcagc tggaagatc tctgagactg      60
tcttgtgctg cttctggatt tacatttgat gattatgcta tgcattgggt gagacaggct     120
cctggaaagg gactggaatg ggtgtctgga gtgtcttgga atggaggaag aatcggatat     180
gctgattctg tgaagggaag atttacaatc tctagagata atgctaagaa ttctctgtat     240
ctgcagatga attctctgag agctgaagat acagctctgt attattgtgc taagggaaga    300
gatgcttttg atatctgggg acagggaaca atggtgacag tgtcttct                 348
```

<210> SEQ ID NO 241
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 241

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
Ser Gly Val Ser Trp Asn Gly Gly Arg Ile Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Lys Gly Arg Asp Ala Phe Asp Ile Trp Gly Gln Gly Thr Met Val
            100                 105                 110
Thr Val Ser Ser
        115

<210> SEQ ID NO 242
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 243
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser

```
                    50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 244
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80
```

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 245
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Arg

<400> SEQUENCE: 245

Xaa Phe Thr Phe Asp Asp Tyr Ala
1               5

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Val
```

```
<400> SEQUENCE: 246

Xaa Ser Trp Asn Ser Gly Ser Ile
1               5

<210> SEQ ID NO 247
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MISC_FEATURE
<222> LOCATION: (10)...(19)
<223> OTHER INFORMATION: May or may not be present

<400> SEQUENCE: 247

Ala Lys Gly Arg Asp Xaa Phe Asp Ile Pro Phe Val Tyr Tyr Tyr Gly
1               5                   10                  15

Met Asp Val

<210> SEQ ID NO 248
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Gly Ile Ser Ser Trp
1               5

<210> SEQ ID NO 249
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala

<400> SEQUENCE: 249

Xaa Ala Ser
1

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (4)..(4)
<223> OTHER INFORMATION: Asn or Tyr

<400> SEQUENCE: 250
```

Gln Xaa Ala Xaa Ser Phe Pro Pro Thr
1               5

<210> SEQ ID NO 251
<211> LENGTH: 311
<212> TYPE: PRT
<213> ORGANISM: Macaca fascicularis

<400> SEQUENCE: 251

Ala Pro Gly Gly Cys Pro Ala Gln Glu Val Ala Arg Gly Val Leu Thr
1               5                   10                  15

Ser Leu Pro Gly Asp Ser Val Thr Leu Thr Cys Pro Gly Gly Glu Pro
                20                  25                  30

Glu Asp Asn Ala Thr Val His Trp Val Leu Arg Lys Pro Ala Val Gly
            35                  40                  45

Ser His Leu Ser Arg Trp Ala Gly Val Gly Arg Arg Leu Leu Leu Arg
        50                  55                  60

Ser Val Gln Leu His Asp Ser Gly Asn Tyr Ser Cys Tyr Arg Ala Gly
65                  70                  75                  80

Arg Pro Ala Gly Thr Val His Leu Leu Val Asp Val Pro Pro Glu Glu
                85                  90                  95

Pro Gln Leu Ser Cys Phe Arg Lys Ser Pro Leu Ser Asn Val Ala Cys
            100                 105                 110

Glu Trp Gly Pro Arg Ser Thr Pro Ser Pro Thr Thr Lys Ala Val Leu
        115                 120                 125

Leu Val Arg Lys Phe Gln Asn Ser Pro Ala Glu Asp Phe Gln Glu Pro
130                 135                 140

Cys Gln Tyr Ser Gln Glu Ser Gln Lys Phe Ser Cys Gln Leu Ala Val
145                 150                 155                 160

Pro Glu Gly Asp Ser Ser Phe Tyr Ile Val Ser Met Cys Val Ala Ser
                165                 170                 175

Ser Val Gly Ser Lys Leu Ser Lys Thr Gln Thr Phe Gln Gly Cys Gly
            180                 185                 190

Ile Leu Gln Pro Asp Pro Pro Ala Asn Ile Thr Val Thr Ala Val Ala
        195                 200                 205

Arg Asn Pro Arg Trp Leu Ser Val Thr Trp Gln Asp Pro His Ser Trp
210                 215                 220

Asn Ser Ser Phe Tyr Arg Leu Arg Phe Glu Leu Arg Tyr Arg Ala Glu
225                 230                 235                 240

Arg Ser Lys Thr Phe Thr Thr Trp Met Val Lys Asp Leu Gln His His
                245                 250                 255

Cys Val Ile His Asp Ala Trp Ser Gly Leu Arg His Val Val Gln Leu
            260                 265                 270

Arg Ala Gln Glu Glu Phe Gly Gln Gly Glu Trp Ser Glu Trp Ser Pro
        275                 280                 285

Glu Ala Met Gly Thr Pro Trp Thr Glu Ser Arg Ser Pro Pro Ala Glu
        290                 295                 300

Asn Glu Val Ser Thr Pro Thr
305                 310

METHODS AND COMPOSITIONS FOR TREATING SUBJECTS HAVING RHEUMATOID ARTHRITIS

RELATED APPLICATIONS

This application claims the benefit of priority to U.S. Provisional Application No. 62/724,212, filed on Aug. 29, 2018, U.S. Provisional Application No. 62/747,301, filed on Oct. 18, 2018, U.S. Provisional Patent Application No. 62/798,697, filed on Jan. 30, 2019, U.S. Provisional Patent Application No. 62/824,399, filed on Mar. 27, 2019, U.S. Provisional Application No. 62/856,431, filed on Jun. 3, 2019, and U.S. Provisional Application No. 62/858,443, filed on Jun. 7, 2019. This application claims the benefit of priority to European Patent Application No. 19192387.9, filed on Aug. 19, 2019. The entire contents of each of the foregoing applications are incorporated herein by reference.

SEQUENCE LISTING

The instant application contains a Sequence Listing which has been filed electronically in ASCII format and is hereby incorporated by reference in its entirety. Said ASCII copy, created on Sep. 30, 2019, is named 118003_10307_SL.txt and is 119,137 bytes in size.

BACKGROUND

Rheumatoid arthritis (RA) is an autoimmune disease characterized by chronic inflammation of synovial tissue, leading to destruction of the joint architecture. The hallmark of the disease is a symmetric polyarthritis characteristically involving the small joints of the hands and feet. The inflammatory process can also target other organs, typically bone marrow (anemia), eye (scleritis, episcleritis), lung (interstitial pneumonitis, pleuritis), cardiac (pericarditis) and skin (nodules, leukocytoclastic vasculitis). Systemic inflammation is characterized by laboratory abnormalities, such as anemia, elevated erythrocyte sedimentation rate, fibrinogen and C-reactive protein (CRP) and by clinical symptoms of fatigue, weight loss, and muscle atrophy in affected joint areas. The presence of polyclonal high-titer rheumatoid factors and anticyclic citrullinated peptide (anti-CCP) antibodies provides evidence of immune dysregulation. It is recognized that cytokines, such as tumor necrosis factor (TNF), interleukin-1 (IL-1) and interleukin-6 (IL-6), play a role in joint inflammation and cartilage damage observed in RA.

The American College of Rheumatology (ACR) and the European League Against Rheumatism (EULAR) have provided guidance for clinicians for treating subjects having RA (see, e.g., Singh, et al. (2016) *Arthritis Care Res* 68(1):1-25; Smollen, et al. (2017) *Ann Rheum Dis* 0:1-18). First-line therapy for subjects newly diagnosed with RA (naïve subjects) is treatment with a conventional synthetic (cs) disease modifying anti-rheumatic drug (DMARD), e.g., methotrexate (MTX), alone or in combination with a glucocorticoid, such as prednisone. In about 50% of subjects, however, disease activity is not effectively controlled by treatment with the csDMARD, and TNF-alpha inhibitor therapy is combined with the csDMARD therapy (Rohr, et al. (2017) *Arthritis Care & Res* 69(6):794). However, increasing data from real-world clinical practice and prescription drug registries across multiple countries indicate that biological (b) DMARDs are frequently used as monotherapy, either at the discretion of the physician or because of patient preference and/or, e.g., intolerance to MTX therapy (see, e.g., Catay, et al. (2016) *BMC Musculoskel Disord* (2016) 17:110). Nonetheless, a significant number of subjects are inadequate responders, non-responders, or intolerant to such treatments, and the disease, including joint destruction, continues to progresses despite the myriad of currently available treatments.

Accordingly, there is a need in the art for methods and compositions useful to identify first-line therapies that would be effective monotherapies for treating particular subjects having RA.

SUMMARY

The present disclosure is based, at least in part, on the surprising discovery that treatment of rheumatoid arthritis (RA) subjects having high baseline interleukin-6 (IL-6) levels with a human anti-interleukin 6 receptor (IL-6R) antibody, or antigen-binding portion thereof, is more efficacious as a first-line therapy than treatment with methotrexate (MTX) or a TNFα inhibitor (e.g., adalimumab).

In particular, an analysis of IL-6 levels from subjects having RA enrolled in the randomized 24-week MONARCH clinical trial (NCT02332590) demonstrated that subjects falling into the tertile of high baseline IL-6 levels (e.g., about ≥3 times the upper limit of normal (3×ULN), e.g., between about 15 pg/ml and about 800 pg/ml) were more likely to achieve a clinically meaningful response to a human anti-IL-6R antibody, or antigen-binding portion thereof, e.g., sarilumab, administration as compared to adalimumab, a TNFα inhibitor other than adalimumab (e.g. etanercept or inflixumab), or MTX administration. This effect was observed across all measured endpoints that included acute phase reactants (e.g., Disease Activity Score using 28 joints and C-reactive protein (DAS28-CRP)) and excluded acute phase reactants (e.g., Health Assessment Questionnaire Disability Index (HAQD1), Clinical Disease Activity Index (CDAI), and/or swollen joint counts), but was not related to a change in IL-6 levels from baseline. Subjects falling into the tertile of high baseline IL-6 levels (e.g., about ≥3 times the upper limit of normal (3×ULN), e.g., between about 15 pg/ml and about 800 pg/ml) were also more likely to achieve improvements in patient reported outcomes (PROs), e.g., pain VAS, SF-36 PCS, SF-36 MCS, and FACIT-F scores, in response to a human anti-IL-6R antibody, or antigen-binding portion thereof, e.g., sarilumab, administration as compared to adalimumab, a TNFα inhibitor other than adalimumab (e.g. etanercept or inflixumab), or MTX administration.

In addition, an analysis of IL-6 levels from subjects having RA enrolled in the Phase III MOBILITY clinical trial (NCT01061736) demonstrated that subjects falling into the tertile of high baseline IL-6 levels (e.g., about ≥3 times the upper limit of normal (3×ULN), e.g., between about 15 pg/ml and about 800 pg/ml) were more likely to achieve a clinically meaningful response to administration of a human anti-IL-6R antibody, or antigen-binding portion thereof, e.g., sarilumab, and MTX, as compared to MTX and placebo administration. The analysis demonstrated that a human anti-IL-6R antibody, or antigen-binding portion thereof, e.g., sarilumab, and MTX treatment was more efficacious for achieving ACR70 and CDAI and HAQDI remission as compared to currently available first-line therapies, but was not related to a change in IL-6 levels from baseline. Subjects falling into the tertile of high baseline IL-6 levels (e.g., about ≥3 times the upper limit of normal (3×ULN), e.g., between about 15 pg/ml and about 800 pg/ml) were also more likely to achieve improvements in patient reported outcomes (PROs), e.g., pain VAS, SF-36 PCS, SF-36 MCS, and FACIT-F scores, in response to a human anti-IL-6R antibody, or antigen-binding portion thereof, e.g., sarilumab, administration as compared to adalimumab, a TNFα inhibitor other than adalimumab (e.g. etanercept or infliximab), or MTX administration.

Furthermore, an analysis of IL-6 levels from subjects having RA and diabetes (e.g., subjects having RA and baseline fasting glucose ≥7 mmol/L or baseline glycosylated hemoglobin (HbA1c) ≥6.5%) who had inadequate response or intolerance to tumour necrosis factor inhibitors enrolled in the Phase III TARGET clinical trial (NCT01709578) or the randomized 24-week MONARCH clinical trial (NCT02332590) demonstrated that subjects falling into the tertile of high baseline IL-6 levels (e.g., about ≥3 times the upper limit of normal (3×ULN), e.g., between about 15 pg/ml and about 800 pg/ml) were more likely to achieve a clinically meaningful response in a measurement of diabetes, e.g., HbA1c levels, following administration of a human anti-IL-6R antibody, or antigen-binding portion thereof, e.g., sarilumab, as compared to adalimumab or placebo administration.

Accordingly, in one aspect, the present disclosure provides methods for treating a subject having rheumatoid arthritis (RA). The methods include determining the level of interleukin 6 (IL-6) in a sample(s) obtained from the subject, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, if the level of IL-6 in the subject sample(s) is determined to be a high IL-6 level, e.g., an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, thereby treating the subject. In one embodiment, the subject having RA also has diabetes. In one embodiment, the subject having RA does not have diabetes.

In another aspect, the present invention provides methods for treating a subject having high interleukin 6 rheumatoid arthritis (high IL-6RA). The methods include selecting a subject having high IL-6RA, e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes.

In another aspect, the present invention provides methods for treating a subject previously identified as having high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml. The methods include administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes.

In one aspect, the present invention provides methods for achieving Disease Activity Score using 28 Joints (DAS28) remission in a subject having high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml The methods include administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes. In one embodiment, the subject achieves a DAS28-CRP remission, e.g., a DAS-CRP score of less than about 2.6, e.g., after about 12 weeks of treatment, or after 24 weeks of treatment.

In another aspect, the present invention provides methods for achieving Clinical Disease Activity Index (CDAI) remission in a subject having high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml. The methods include administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes. In one embodiment, the subject achieves a CDI remission, e.g., a CDAI score of greater than or equal to about 2.8, e.g., after about 12 weeks of treatment, or after 24 weeks of treatment.

In yet another aspect, the present invention provides methods for achieving an ACR70 response in a subject having high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml. The methods include administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes. The subject may achieve an ACR70 response after about 12 weeks of treatment, or after 24 weeks of treatment.

In one aspect, the present invention provides methods for treating a subject having rheumatoid arthritis (RA) with a human anti-interleukin 6 receptor (IL-6R) antibody, or antigen-binding portion thereof. The methods include selecting a subject having a high interleukin 6 (IL-6) level, e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having RA also has diabetes. In one embodiment, the subject having RA does not have diabetes.

In one aspect, the present invention provides methods for inhibiting joint damage in a subject. The methods include selecting a treatment naïve subject having high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, as a monotherapy, thereby inhibiting joint damage in the subject. In one embodiment, the subject having high IL-6RA also has diabetes. In one embodiment, the subject having high IL-6RA does not have diabetes. In some embodiments, as a result of the treatment, e.g., 200 mg q2w sarilumab treatment, the subject achieves an inhibition of progression of structural damage at, e.g., week 52, as measured by the change in the modified Van der Heijde total Sharp score (mTSS), e.g., an mTSS score of 0.25. In some embodiments, as a result of the treatment, e.g., 200 mg q2w sarilumab treatment, the subject achieves a reduction of approximately 90% in the radiographic progression as assessed by the mTSS at, e.g., week 52. In some embodiments, after at least 24 weeks of treatment, e.g., 200 mg q2w sarilumab treatment, the subject achieves a change from baseline (BL) in the modified Van der Heijde total Sharp score (mTSS) of at most 0.6. In some embodiments, after at least 52 weeks of treatment, e.g., 200 mg q2w sarilumab treatment, the subject achieves a change from baseline (BL) in the modified Van der Heijde total Sharp score (mTSS) of at most 1. In some embodiments, after at least 24 weeks of treatment, e.g., 200 mg q2w sarilumab treatment, the subject achieves a change from baseline (BL) in the modified Van der Heijde total Sharp score (mTSS) of at most 0.2. In some embodiments, after at least 52 weeks of treatment, e.g., 200 mg q2w sarilumab treatment, the subject achieves a change from baseline (BL) in the modified Van der Heijde total Sharp score (mTSS) of at most 0.3.

In another aspect, the present invention provides methods for preventing further joint damage in a subject caused by intolerance or inadequate response to a treatment. The methods include selecting a subject having high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby preventing further joint damage in the subject. In one embodiment, the subject having high IL-6RA also has diabetes. In one embodiment, the subject having high IL-6RA does not have diabetes. In some embodiments, as a result of the treatment, e.g., 200 mg q2w sarilumab treatment, the subject achieves an inhibition of progression of structural damage at, e.g., week 52, as measured by the change in the modified Van der Heijde total Sharp score (mTSS), e.g., an mTSS score of 0.25. In some embodiments, as a result of the treatment, e.g., 200 mg q2w sarilumab treatment, the subject achieves a reduction of approximately 90% in the radiographic progression as assessed by the mTSS at, e.g., week 52. In some embodiments, after at least 24 weeks of treatment, e.g., 200 mg q2w sarilumab treatment, the subject achieves a change from baseline (BL) in the modified Van der Heijde total Sharp score (mTSS) of at most 0.6. In some embodiments, after at least 52 weeks of treatment, e.g., 200 mg q2w sarilumab treatment, the subject achieves a change from baseline (BL) in the modified Van der Heijde total Sharp score (mTSS) of at most 1. In some embodiments, after at least 24 weeks of treatment, e.g., 200 mg q2w sarilumab treatment, the subject achieves a change from baseline (BL) in the modified Van der Heijde total Sharp score (mTSS) of at most 0.2. In some embodiments, after at least 52 weeks of treatment, e.g., 200 mg q2w sarilumab treatment, the subject achieves a change from baseline (BL) in the modified Van der Heijde total Sharp score (mTSS) of at most 0.3.

In one aspect, the present invention provides methods for treating a subject. The methods include determining whether a subject suspected of having rheumatoid arthritis (RA) has high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes.

In one aspect, the present invention provides methods for treating a methotrexate-intolerant subject having rheumatoid arthritis (RA). The methods include determining whether the subject has high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes.

In another aspect, the present invention provides methods for treating a methotrexate-inadequate responder subject having rheumatoid arthritis (RA). The methods include determining whether the subject has high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby treating the subject. In one embodiment, the subject having high IL-6RA also has diabetes. In one embodiment, the subject having high IL-6RA does not have diabetes.

In one aspect, the present invention provides methods for treating a subject having rheumatoid arthritis. The methods include the steps of determining the level of IL-6 in a sample(s) from the subject so that the subject is determined to belong to either a first category of rheumatoid arthritis disease severity or a second category of rheumatoid arthritis disease severity; assigning a therapy to the subject if the subject is associated with the first category of rheumatoid arthritis disease severity, wherein the therapy is administration of a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof; and administering, e.g., subcutaneously administering, the human IL-6R antibody, or antigen-binding portion thereof, to the subject, thereby treating the subject having rheumatoid arthritis. In one embodiment, the subject having RA also has diabetes. In one embodiment, the subject having RA does not have diabetes.

In another aspect, the present invention provides methods for treating subjects having rheumatoid arthritis. The methods include the steps of determining the level of IL-6 in serum samples from the subjects so that each subject is determined to belong to either a first category of rheumatoid arthritis disease severity or a second category of rheumatoid arthritis disease severity; assigning a therapy to the subjects in the first category of rheumatoid arthritis disease severity, wherein the therapy is administration of a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof; and administering, e.g., subcutaneously administering, the human IL-6R antibody, or antigen-binding portion thereof, to the subjects in the first category of rheumatoid arthritis disease severity, thereby treating the subjects having rheumatoid arthritis. In one embodiment, the subject having RA also has diabetes. In one embodiment, the subject having RA does not have diabetes.

In one embodiment, the first category of rheumatoid arthritis disease severity corresponds to a high level of IL-6, e.g., an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml.

In one embodiment, the second category of rheumatoid arthritis disease severity corresponds to a moderate level of IL-6 and/or a low level of IL-6, e.g., an IL-6 level (e.g., serum level) less than about 1 times the upper limit of normal (1×ULN), e.g., less than about 3×ULN, e.g., between about 1×ULN and about 3×ULN); or an IL-6 level (e.g., serum level) less than about 15 pg/ml, e.g., less than about 35 pg/ml, e.g., between about 1 pg/ml and about 35 pg/ml.

In one aspect, the present invention provides methods for preventing further joint damage caused by intolerance or inadequate response to prior treatment with a DMARD in a subject having rheumatoid arthritis. The methods include selecting a subject having high interleukin 6 rheumatoid arthritis (high IL-6RA), e.g., a subject having RA and an IL-6 level (e.g., serum level) greater than about 1.5 times the upper limit of normal (1.5×ULN), e.g., between about 1.5×ULN and 70×ULN, e.g., greater than about 3×ULN, e.g., between about 3×ULN and 70×ULN; or an IL-6 level (e.g., serum level) greater than about 15 pg/ml, e.g., between about 15 and about 800 pg/ml, e.g., greater than about 35 pg/ml, e.g., between about 35 pg/ml and 800 pg/ml, and administering, e.g., subcutaneously administering, to the subject a therapeutically effective amount, e.g., about 75 mg to about 300 mg, such as about 200 mg, such as about 200 mg about once every two weeks (q2w), of a human anti-interleukin 6 receptor (IL-6R) antibody, or antigen-binding portion thereof, e.g., an anti-IL6R antibody, or antigen-binding portion thereof, comprising three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively, e.g., an anti-IL6R antibody, or antigen-binding portion thereof, comprising an HCVR having the amino acid sequence of SEQ ID NO: 19 and an LCVR having the amino acid sequence of SEQ ID NO: 27, e.g., sarilumab, or a biosimilar thereof, thereby preventing further joint damage in the subject. In one embodiment, the subject having high IL-6RA also has diabetes. In one embodiment, the subject having high IL-6RA does not have diabetes. In some embodiments, as a result of the treatment, e.g., 200 mg q2w sarilumab treatment, the subject achieves an inhibition of progression of structural damage at, e.g., week 52, as measured by the change in the modified Van der Heijde total Sharp score (mTSS), e.g., an mTSS score of 0.25. In some embodiments, as a result of the treatment, e.g., 200 mg q2w sarilumab treatment, the subject achieves a reduction of approximately 90% in the radiographic progression as assessed by the mTSS at, e.g., week 52. In some embodiments, after at least 24 weeks of treatment, e.g., 200 mg q2w sarilumab treatment, the subject achieves a change from baseline (BL) in the modified Van der Heijde total Sharp score (mTSS) of at most 0.6. In some embodiments, after at least 52 weeks of treatment, e.g., 200 mg q2w sarilumab treatment, the subject achieves a change from baseline (BL) in the modified Van der Heijde total Sharp score (mTSS) of at most 1. In some embodiments, after at least 24 weeks of treatment, e.g., 200 mg q2w sarilumab treatment, the subject achieves a change from baseline (BL) in the modified Van der Heijde total Sharp score (mTSS) of at most 0.2. In some embodiments, after at least 52 weeks of treatment, e.g., 200 mg q2w sarilumab treatment, the subject achieves a change from baseline (BL) in the modified Van der Heijde total Sharp score (mTSS) of at most 0.3.

In one embodiment, the subject is suspected of having RA. In another embodiment, the subject is suspected of having rheumatoid arthritis and the method further comprises determining whether the subject has high IL-6RA. In one embodiment, the subject is suspected of having RA and diabetes. In another embodiment, the subject is suspected of having rheumatoid arthritis and diabetes and the method further comprises determining whether the subject has high IL-6RA. In another embodiment, the subject is suspected of having rheumatoid arthritis and diabetes and the method further comprises determining whether the subject has high IL-6RA and diabetes. In one embodiment, the subject having high IL-6RA does not have diabetes.

The methods for determining whether the subject suspected of having RA (or RA and diabetes) has high IL-6RA may include determining one or more of erythrocyte sedimentation rate (ESR); C-reactive protein (CRP) level; complete blood count (CBC); the level of rheumatoid factor (RF); the level of antinuclear antibody (ANA); the level of anti-cyclic citrullinated peptide (anti-CCP); the level of anti-mutated citrullinated vimentin (anti-MCV); the level of glycosylated hemoglobin (HbA1c); and the level of IL-6.

In some embodiments, the subject was previously diagnosed as having RA.

In some embodiments, the subject was previously diagnosed as having RA and previously diagnosed as having diabetes.

In some embodiments, the subject is a treatment naïve RA subject.

In some embodiments, the subject is a treatment naïve RA subject and a treatment naïve diabetes subject.

In other embodiments, the subject was previously administered one or more therapeutic agents for treating RA, such as a disease-modifying antirheumatic drug (DMARD). In other embodiments, the subject was previously administered one or more therapeutic agents for treating diabetes.

In one embodiment, the subject has rheumatoid arthritis and diabetes. In one embodiment, the treatment results in a clinical improvement in a measure of diabetes, e.g., HbA1c, e.g., a decrease of about 0.4% HbA1c level from baseline HbA1c level.

The DMARD administered to the subject may be one or more of a conventional synthetic (cs) DMARD, e.g., methotrexate (MTX), leflunomide, or sulfasalazine; one or more of a biological (b) DMARD, e.g., one or more of a tumor necrosis factor (TNF)-inhibitor, such as, adalimumab, certolizumab pegol, etanercept, golimumab, infliximab, or a biosimilar thereof, abatacept, rituximab, tocilizumab, clazakizumab, or sirukumab, or a biosimilar thereof; and/or one or more of a targeted synthetic (ts) DMARD, e.g., a Janus kinase (Jak) inhibitor, such as tofacitinib or baricitinib.

In another embodiment, the one or more therapeutic agent for treating RA is a gluccocorticoid.

The subject may be a DMARD inadequate responder (DMARD-IR) subject; a DMARD intolerant subject; a TNF inhibitor inadequate responder subject; or a TNF inhibitor intolerant subject.

The subject sample(s) may be a fluid sample, such as a blood sample, e.g., a serum sample.

The level of IL-6 may be determined by ELISA assay.

In one embodiment, the anti-IL6R antibody, or antigen-binding portion thereof, is a fully human anti-IL6R antibody, or antigen-binding portion thereof.

In another embodiment, the anti-IL6R antibody, or antigen-binding portion thereof, comprises heavy and light chain CDR sequences from a HCVR/LCVR sequence pair selected from the group consisting of SEQ ID NOs: 3/11; 227/229; 19/27; 231/233; 35/43; 51/59; 67/75; 83/91; 99/107; 115/123; 131/139; 147/155; 239/155; 241/155; 163/171; 179/187; 235/237; 195/203; and 211/219.

In yet another embodiment, the anti-IL6R antibody, or antigen-binding portion thereof, comprises heavy and light chain CDR sequences from the HCVR/LCVR sequence pair of SEQ ID NOs: 19/27.

In one embodiment, the anti-IL6R antibody, or antigen-binding portion thereof, comprises three heavy chain complementarity determining region (HCDR) sequences comprising SEQ ID NOs:21, 23, and 25, respectively, and three light chain complementarity determining (LCDR) sequences comprising SEQ ID NOs: 29, 31, and 33, respectively.

In one embodiment, the anti-IL6R antibody, or antigen-binding portion thereof, comprises an HCVR having the amino acid sequence of SEQ ID NO: 19 and an LCVR having the amino acid sequence of SEQ ID NO: 27.

In another embodiment, the anti-IL6R antibody, or antigen-binding portion thereof, is sarilumab, or a biosimilar thereof.

In one embodiment, the anti-IL6R antibody, or antigen-binding portion thereof, is administered to the subject in a pharmaceutical composition.

In one embodiment, the pharmaceutical composition is present in a pre-filled syringe.

In one embodiment, the pharmaceutical composition comprises about 75 mg to about 300 mg of the antibody, or antigen-binding portion thereof.

In one embodiment, the pharmaceutical composition comprises about 45 mM arginine, about 21 mM histidine, about 0.2% w/v polysorbate-20, and about 5% w/v sucrose.

In one embodiment, the pharmaceutical composition is administered to the subject about once every two weeks (q2w).

In one embodiment, the pharmaceutical composition is administered to the subject as a dose of about 200 mg about once every two weeks (q2w).

The pharmaceutical composition may be administered to the subject subcutaneously or intravenously.

In one embodiment, the pharmaceutical composition is administered to the subject subcutaneously.

In one embodiment, the pharmaceutical composition the subcutaneous administration is self-administration.

BRIEF DESCRIPTION OF THE DRAWINGS

FIG. 3 is a Table depicting the baseline disease activity according to baseline IL-6 tertile for the subjects in the MOBILITY and MONARCH studies.

FIG. 6 is a table depicting the odds ratios for efficacy parameters in the subjects in the MOBILITY study.

FIG. 9 is a table depicting the odds ratios for efficacy parameters in the subjects in the MONARCH study.

FIG. 10A are tables depicting the comparison of responses according to baseline IL-6 or CRP in the subjects in the MOBILITY and MONARCH studies.

FIG. 10B is a table depicting that high baseline IL-6 is better than high CRP at predicting response to treatment.

FIG. 11A is a table depicting the consistency of treatment difference vs. comparator in the high IL-6 tertile in the subjects in the MOBILITY and MONARCH studies.

FIG. 11B is a table depicting the consistency of treatment difference in high IL-6 subgroups in MOBILITY and MONARCH studies across many endpoints (between group difference in high IL-6 tertile).

FIG. 12 is a table depicting the incidence of treatment-emergent adverse events by IL-6 tertile in the MOBILITY and MONARCH studies.

FIGS. 15A-15B are bar graphs depicting the proportion of responders at (A) Week 24 and (B) Week 52 according to baseline IL-6 tertile in the MOBILITY study. ACR20/50/70, patients achieving ≥20/50/70% improvement according to American College of Rheumatology criteria; CDAI, Clinical Disease Activity Index; CRP, C-reactive protein; DAS28, Disease Activity Score of 28 joints; HAQ-DI, Health Assessment Questionnaire-Disability Index; IL-6, interleukin-6; MTX, methotrexate; q2w, every 2 weeks.

DETAILED DESCRIPTION

Figure 1:
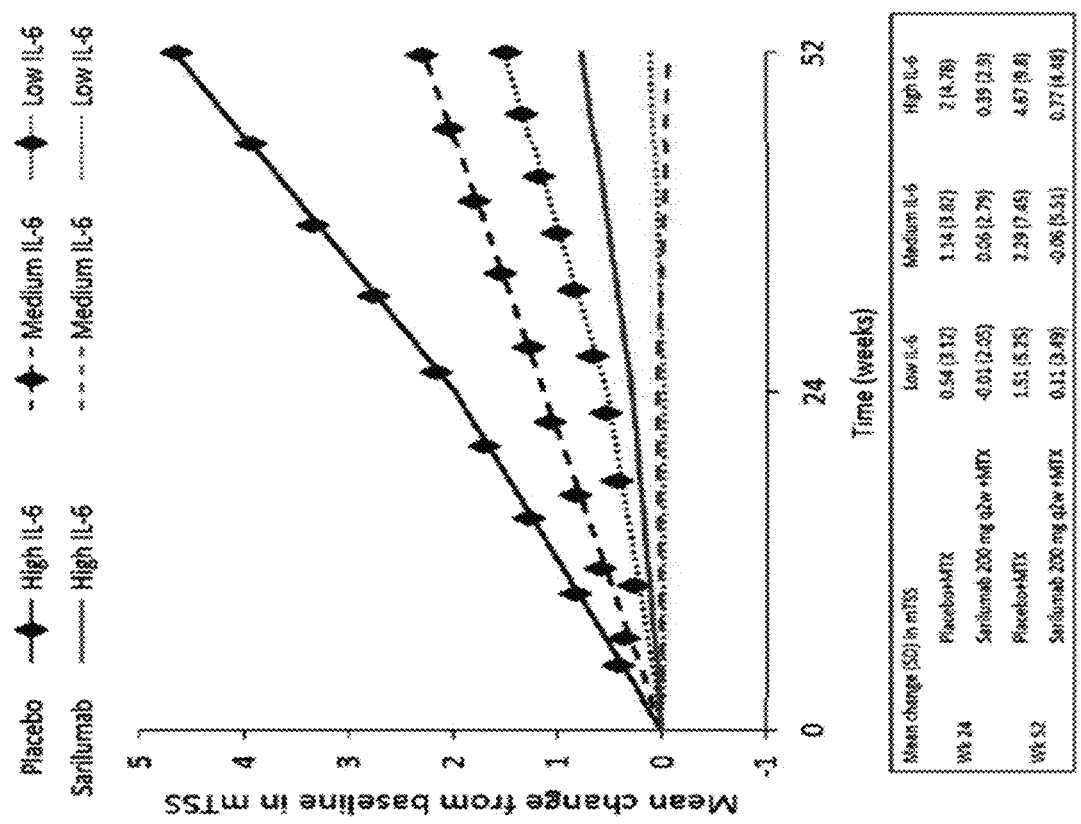
FIG. 1 is a graph depicting the mean change from baseline in the van der Heijde modified Total Sharp score (mTSS) in subjects in each of three tertiles of IL-6 levels (i.e., subjects having low IL-6 levels, medium or moderate IL-6 levels, or high IL-6 levels) and administered a placebo and methotrexate or sarilumab and methotrexate at 24 and 52 weeks post-administration. A Table below provides the numerical values of the points plotted on the graph.
Figure 2:
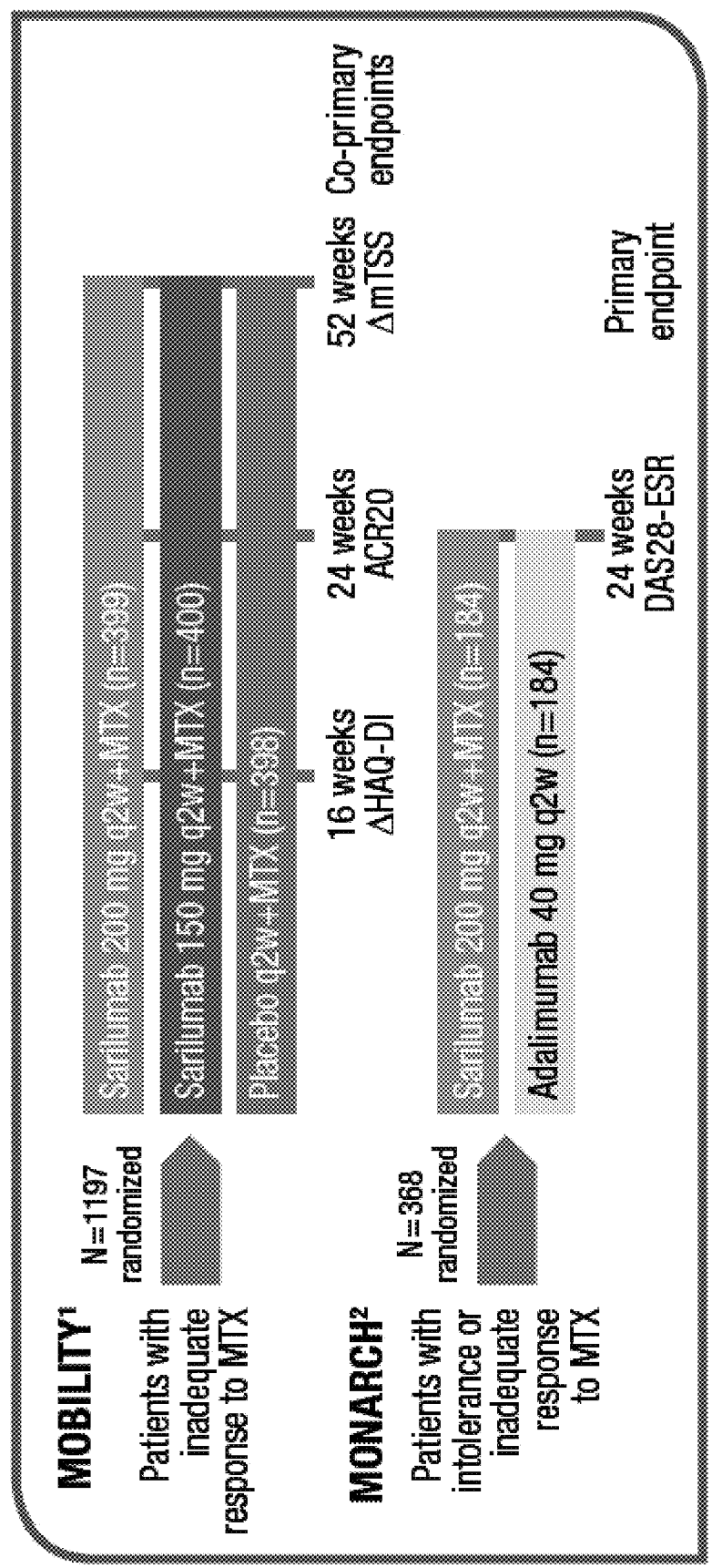
FIG. 2 schematically depicts the MOBILITY and MONARCH study designs.

The present disclosure is based, at least in part, on the surprising discovery that treatment of rheumatoid arthritis (RA) subjects having high baseline interleukin-6 (IL-6) levels with a human anti-interleukin 6 receptor (IL-6R) antibody, or antigen-binding portion thereof, is more efficacious as a first-line therapy than treatment with methotrexate (MTX), adalimumab, or a TNFα inhibitor other than adalimumab (e.g. etanercept or infliximab). It has also been surprisingly discovered that patient reported outcome quality of life measurements were improved in rheumatoid arthritis (RA) subjects having high baseline interleukin-6 (IL-6) levels treated with a human anti-interleukin 6 receptor (IL-6R) antibody, or antigen-binding portion thereof, as a first-line therapy as compared to subjects treated with methotrexate (MTX), adalimumab, or a TNFα inhibitor other than adalimumab (e.g. etanercept or infliximab).

In particular, an analysis of IL-6 levels from subjects having RA enrolled in the randomized 24-week MONARCH clinical trial (NCT02332590) demonstrated that subjects falling into the tertile of high baseline IL-6 levels (e.g., about ≥3 times the upper limit of normal (3×ULN), e.g., between about 15 pg/ml and about 800 pg/ml) were more likely to achieve a clinically meaningful response to a human anti-IL-6R antibody, or antigen-binding portion thereof, e.g., sarilumab, administration as compared to adalimumab, a TNFα inhibitor other than adalimumab (e.g. etanercept or infliximab), or MTX administration. This effect was observed across all measured endpoints that included acute phase reactants (e.g., Disease Activity Score using 28 joints and C-reactive protein (DAS28-CRP)) and excluded acute phase reactants (e.g., Health Assessment Questionnaire Disability Index (HAQD1), Clinical Disease Activity Index (CDAI), and/or swollen joint counts), but was not related to a change in IL-6 levels from baseline. Subjects falling into the tertile of high baseline IL-6 levels (e.g., about ≥3 times the upper limit of normal (3×ULN), e.g., between about 15 pg/ml and about 800 pg/ml) were also more likely to achieve improvements in patient reported outcomes (PROs), e.g., pain VAS, SF-36 PCS, SF-36 MCS, and FACIT-F scores, in response to a human anti-IL-6R antibody, or antigen-binding portion thereof, e.g., sarilumab, administration as compared to adalimumab, a TNFα inhibitor other than adalimumab (e.g. etanercept or infliximab), or MTX administration.

In addition, an analysis of IL-6 levels from subjects having RA enrolled in the Phase III MOBILITY clinical trial (NCT01061736) demonstrated that subjects falling into the tertile of high baseline IL-6 levels (e.g., about ≥3 times the upper limit of normal (3×ULN), e.g., between about 15 pg/ml and about 800 pg/ml) were more likely to achieve a clinically meaningful response to administration of a human anti-IL-6R antibody, or antigen-binding portion thereof, e.g., sarilumab, and MTX as compared to MTX and placebo administration. The analysis demonstrated that a human anti-IL-6R antibody, or antigen-binding portion thereof, e.g., sarilumab, and MTX treatment was more efficacious for achieving ACR70 and CDAI and HAQDI remission as compared to currently available first-line therapies, but was not related to a change in IL-6 levels from baseline. Subjects falling into the tertile of high baseline IL-6 levels (e.g., about ≥3 times the upper limit of normal (3×ULN), e.g., between about 15 pg/ml and about 800 pg/ml) were also more likely to achieve improvements in patient reported outcomes (PROs), e.g., pain VAS, SF-36 PCS, SF-36 MCS, and FACIT-F scores, in response to a human anti-IL-6R antibody, or antigen-binding portion thereof, e.g., sarilumab, administration as compared to adalimumab, a TNFα inhibitor other than adalimumab (e.g. etanercept or infliximab), or MTX administration.

Furthermore, an analysis of IL-6 levels from subjects having RA and diabetes (e.g., subjects having RA and baseline fasting glucose ≥7 mmol/L or baseline glycosylated hemoglobin (HbA1c) ≥6.5%) who had inadequate response or intolerance to tumour necrosis factor inhibitors enrolled in the Phase III TARGET clinical trial (NCT01709578) or the randomized 24-week MONARCH clinical trial (NCT02332590) demonstrated that subjects falling into the tertile of high baseline IL-6 levels (e.g., about ≥3 times the upper limit of normal (3×ULN), e.g., between about 15 pg/ml and about 800 pg/ml) were more likely to achieve a clinically meaningful response in a measurement of diabetes, e.g., HbA1c levels, e.g., a decrease of about 0.4% HbA1c level from baseline HbA1c level, following administration of a human anti-IL-6R antibody, or antigen-binding portion thereof, e.g., sarilumab, as compared to adalimumab or placebo administration.

Various aspects of the disclosure are described in further detail in the following subsections:

I. Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "determining" means methods which include detecting the presence or absence of IL-6 in a sample and/or quantifying the amount of IL-6 in a sample. Measuring can be accomplished by methods known in the art and those further described herein.

The term "level of interleukin 6" or "level of IL-6" refers to an amount of IL-6 protein present in a sample being tested. In one embodiment, the level of IL-6 is an absolute level or amount (e.g., pg/ml). In another embodiment, the level of IL-6 is a relative level or amount (e.g., relative intensity of signals).

The terms "high IL-6 levels" and "high interleukin-6 levels," used interchangeably herein, refer to levels of IL-6 in a sample(s) from a subject that are, in one embodiment, a level of IL-6 in a sample(s) from a subject having RA (or a subject having RA and diabetes) who more likely to achieve a clinically meaningful response, e.g., DAS28-CRP remission, CDAI remission, an ACR70 response, inhibition of joint damage, e.g., further joint damage, following administration of a human anti-IL-6R antibody, or antigen-binding portion thereof, e.g., sarilumab, as compared to adalimumab, a TNFα inhibitor other than adalimumab (e.g. etanercept or infliximab), or MTX administration; and or who is more likely to achieve a clinically meaningful response, e.g., DAS28-CRP remission, CDAI remission, an ACR70 response, inhibition of joint damage, e.g., further joint damage, to administration of a human anti-IL-6R antibody, or antigen-binding portion thereof, e.g., sarilumab, and MTX administration as compared to MTX and placebo administration.

In another embodiment, a high IL-6 level is greater than about 1.5 times the upper limit of normal (1.5×ULN); greater than about 1.75×ULN; about 2×ULN; about 2.25× ULN; about 2.5×ULN; about 2.75×ULN; about 2.80×ULN; about 2.85×ULN; about 2.90×ULN; about 2.95×ULN; or greater than about 3×ULN. The upper limit of normal of IL-6 in the serum of a subject is about 12.5 pg/ml. Ranges and values intermediate to the above recited ranges and values are also contemplated to be part of the invention.

In another embodiment, high IL-6 levels are greater than about 15 pg/ml, e.g., about 20 pg/ml; 25 pg/ml; 30 pg/ml; 35 pg/ml; 40 pg/ml; 45 pg/ml; 50 pg/ml; 55 pg/ml; 60 pg/ml; 65 pg/ml; 70 pg/ml; 75 pg/ml; 80 pg/ml; 85 pg/ml; 90 pg/ml; 95 pg/ml; 100 pg/ml; 105 pg/ml; 110 pg/ml; 120 pg/ml; 130 pg/ml; 140 pg/ml; 150 pg/ml; 160 pg/ml; 170 pg/ml; 180 pg/ml; 190 pg/ml; 200 pg/ml; 210 pg/ml; 220 pg/ml; 230 pg/ml; 240 pg/ml; 250 pg/ml; 260 pg/ml; 270 pg/ml; 280 pg/ml; 290 pg/ml; 300 pg/ml; 310 pg/ml; 320 pg/ml; 330 pg/ml; 340 pg/ml; 350 pg/ml; 360 pg/ml; 370 pg/ml; 380 pg/ml; 390 pg/ml; 400 pg/ml; 410 pg/ml; 420 pg/ml; 430 pg/ml; 440 pg/ml; 450 pg/ml; 460 pg/ml; 470 pg/ml; 480 pg/ml; 490 pg/ml; 500 pg/ml; 510 pg/ml; 520 pg/ml; 530 pg/ml; 540 pg/ml; 550 pg/ml; 560 pg/ml; 570 pg/ml; 580 pg/ml; 590 pg/ml; 600 pg/ml; 610 pg/ml; 620 pg/ml; 630 pg/ml; 640 pg/ml; 650 pg/ml; 660 pg/ml; 670 pg/ml; 680 pg/ml; 690 pg/ml; 700 pg/ml; 710 pg/ml; 720 pg/ml; 730 pg/ml; 740 pg/ml; 750 pg/ml; 760 pg/ml; 770 pg/ml; 780 pg/ml; 790 pg/ml; or about 800 pg/ml; e.g., between about 15 and about 800 pg/ml; between about 20 and about 800 pg/ml; between about 25 and about 800 pg/ml; between about 30 and about 800 pg/ml; between about 35 and about 800 pg/ml; between about 40 and about 800 pg/ml; between about 45 and about 800 pg/ml; between about 50 and about 800 pg/ml; between about 55 and about 800 pg/ml; between about 60 and about 800 pg/ml; between about 65 and about 800 pg/ml; between about 70 and about 800 pg/ml; between about 75 and about 800 pg/ml; between about 80 and about 800 pg/ml; between about 85 and about 800 pg/ml; between about 90 and about 800 pg/ml; between about 95 and about 800 pg/ml; between about 100 and about 800 pg/ml; between about 105 and about 800 pg/ml; between about 15 and about 800 pg/ml; between about 20 and about 800 pg/ml; between about 25 and about 750 pg/ml; between about 30 and about 750 pg/ml; between about 40 and about 750 pg/ml; between about 45 and about 750 pg/ml; between about 50 and about 750 pg/ml; between about 55 and about 750 pg/ml; between about 60 and about 750 pg/ml; between about 65 and about 750 pg/ml; between about 70 and about 750 pg/ml; between about 75 and about 750 pg/ml; between about 80 and about 750 pg/ml; between about 85 and about 750 pg/ml; between about 90 and about 750 pg/ml; between about 95 and about 750 pg/ml; between about 100 and about 750 pg/ml; between about 105 and about 750 pg/ml; between about 15 and about 800 pg/ml; between about 20 and about 800 pg/ml; between about 25 and about 700 pg/ml; between about 30 and about 700 pg/ml; between about 40 and about 700 pg/ml; between about 45 and about 700 pg/ml; between about 50 and about 700 pg/ml; between about 55 and about 700 pg/ml; between about 60 and about 700 pg/ml; between about 65 and about 700 pg/ml; between about 70 and about 700 pg/ml; between about 75 and about 700 pg/ml; between about 80 and about 700 pg/ml; between about 85 and about 700 pg/ml; between about 90 and about 700 pg/ml; between about 95 and about 700 pg/ml; between about 100 and about 700 pg/ml; or between about 105 and about 700 pg/ml. In one embodiment, high IL-6 levels are greater than about 35 pg/ml, e.g., about 35 pg/ml to about 800 pg/ml. Ranges and values intermediate to the above recited ranges and values are also contemplated to be part of the invention.

A subject having "high interleukin 6 rheumatoid arthritis" or "high IL-6RA" (e.g., a subject belonging to a first category of RA disease severity) (or "high IL-6RA and diabetes") is, in one embodiment, a subject having RA who has a high level of IL-6 and is more likely to achieve a clinically meaningful response following administration of a human anti-IL-6R antibody, or antigen-binding portion thereof, e.g., sarilumab, as compared to adalimumab, a TNFα inhibitor other than adalimumab (e.g. etanercept or infliximab), or MTX administration; and/or who is were more likely to achieve a clinically meaningful response to administration of a human anti-IL-6R antibody, or antigen-binding portion thereof, e.g., sarilumab, and MTX administration as compared to MTX and placebo administration.

In another embodiment, a subject having high IL-6RA (or "high IL-6RA and diabetes") is a subject having rheumatoid arthritis and an IL-6 level greater than about 1.5 times the upper limit of normal (1.5×ULN); about 1.75×ULN; about 2×ULN; about 2.25×ULN; about 2.5×ULN; about 2.75× ULN; or about 3×ULN, e.g., between about 1.5×ULN and 70×ULN; between about 1.75×ULN and 70×ULN; between about 2×ULN and 70×ULN; between about 2.5×ULN and 70×ULN; between about 2.75×ULN and 70×ULN; between about 3×ULN and 70×ULN; between about 1.5×ULN and 60×ULN; between about 1.75×ULN and 60×ULN; between about 2×ULN and 60×ULN; between about 2.5×ULN and 60×ULN; between about 2.75×ULN and 60×ULN; between about 3×ULN and 60×ULN; between about 1.5×ULN and 50×ULN; between about 1.75×ULN and 50×ULN; between about 2×ULN and 50×ULN; between about 2.5×ULN and 50×ULN; between about 2.75×ULN and 50×ULN; between about 3×ULN and 50×ULN; between about 1.5×ULN and 40×ULN; between about 1.75×ULN and 40×ULN; between about 2×ULN and 40×ULN; between about 2.5×ULN and 40×ULN; between about 2.75×ULN and 40×ULN; between about 3×ULN and 40×ULN; between about 1.5×ULN and 30×ULN; between about 1.75×ULN and 30×ULN; between about 2×ULN and 30×ULN; between about 2.5×ULN and 30×ULN; between about 2.75×ULN and 30×ULN; between about 3×ULN and 30×ULN; between about 1.5×ULN and 20×ULN; between about 1.75×ULN and 20×ULN; between about 2×ULN and 20×ULN; between about 2.5×ULN and 20×ULN; between about 2.75×ULN and 20×ULN; between about 3×ULN and 20×ULN; between about 1.5×ULN and 10×ULN; between about 1.75×ULN and 10×ULN; between about 2×ULN and 10×ULN; between about 2.5×ULN and 10×ULN; between about 2.75×ULN and 10×ULN; between about 3×ULN and 10×ULN. In one embodiment, a subject having high IL-6RA (or "high IL-6RA and diabetes") is a subject having rheumatoid arthritis and an IL-6 level greater than about 3 times the upper limit of normal (3×ULN); e.g., between about 3×ULN and about 70×ULN.

Ranges and values intermediate to the above recited ranges and values are also contemplated to be part of the invention.

In yet another embodiment, a subject having high IL-6RA (or "high IL-6RA and diabetes") is a subject having rheumatoid arthritis (or a subject having RA and diabetes) and an IL-6 level (e.g., serum level) greater than about 15 pg/ml, e.g., about 20 pg/ml; 25 pg/ml; 30 pg/ml; 35 pg/ml; 40 pg/ml; 45 pg/ml; 50 pg/ml; 55 pg/ml; 60 pg/ml; 65 pg/ml; 70 pg/ml; 75 pg/ml; 80 pg/ml; 85 pg/ml; 90 pg/ml; 95 pg/ml; 100 pg/ml; 105 pg/ml; 110 pg/ml; 120 pg/ml; 130 pg/ml; 140 pg/ml; 150 pg/ml; 160 pg/ml; 170 pg/ml; 180 pg/ml; 190 pg/ml; 200 pg/ml; 210 pg/ml; 220 pg/ml; 230 pg/ml; 240 pg/ml; 250 pg/ml; 260 pg/ml; 270 pg/ml; 280 pg/ml; 290 pg/ml; 300 pg/ml; 310 pg/ml; 320 pg/ml; 330 pg/ml; 340 pg/ml; 350 pg/ml; 360 pg/ml; 370 pg/ml; 380 pg/ml; 390 pg/ml; 400 pg/ml; 410 pg/ml; 420 pg/ml; 430 pg/ml; 440 pg/ml; 450 pg/ml; 460 pg/ml; 470 pg/ml; 480 pg/ml; 490 pg/ml; 500 pg/ml; 510 pg/ml; 520 pg/ml; 530 pg/ml; 540 pg/ml; 550 pg/ml; 560 pg/ml; 570 pg/ml; 580 pg/ml; 590 pg/ml; 600 pg/ml; 610 pg/ml; 620 pg/ml; 630 pg/ml; 640 pg/ml; 650 pg/ml; 660 pg/ml; 670 pg/ml; 680 pg/ml; 690 pg/ml; 700 pg/ml; 710 pg/ml; 720 pg/ml; 730 pg/ml; 740 pg/ml; 750 pg/ml; 760 pg/ml; 770 pg/ml; 780 pg/ml; 790 pg/ml; or about 800 pg/ml; e.g., between about 15 and about 800 pg/ml; between about 20 and about 800 pg/ml; between about 25 and about 800 pg/ml; between about 30 and about 800 pg/ml; between about 35 and about 800 pg/ml; between about 40 and about 800 pg/ml; between about 45 and about 800 pg/ml; between about 50 and about 800 pg/ml; between about 55 and about 800 pg/ml; between about 60 and about 800 pg/ml; between about 65 and about 800 pg/ml; between about 70 and about 800 pg/ml; between about 75 and about 800 pg/ml; between about 80 and about 800 pg/ml; between about 85 and about 800 pg/ml; between about 90 and about 800 pg/ml; between about 95 and about 800 pg/ml; between about 100 and about 800 pg/ml; between about 105 and about 800 pg/ml; between about 25 and about 750 pg/ml; between about 30 and about 750 pg/ml; between about 40 and about 750 pg/ml; between about 45 and about 750 pg/ml; between about 50 and about 750 pg/ml; between about 55 and about 750 pg/ml; between about 60 and about 750 pg/ml; between about 65 and about 750 pg/ml; between about 70 and about 750 pg/ml; between about 75 and about 750 pg/ml; between about 80 and about 750 pg/ml; between about 85 and about 750 pg/ml; between about 90 and about 750 pg/ml; between about 95 and about 750 pg/ml; between about 100 and about 750 pg/ml; between about 105 and about 750 pg/ml; between about 25 and about 700 pg/ml; between about 30 and about 700 pg/ml; between about 40 and about 700 pg/ml; between about 45 and about 700 pg/ml; between about 50 and about 700 pg/ml; between about 55 and about 700 pg/ml; between about 60 and about 700 pg/ml; between about 65 and about 700 pg/ml; between about 70 and about 700 pg/ml; between about 75 and about 700 pg/ml; between about 80 and about 700 pg/ml; between about 85 and about 700 pg/ml; between about 90 and about 700 pg/ml; between about 95 and about 700 pg/ml; between about 100 and about 700 pg/ml; or between about 105 and about 700 pg/ml. In one embodiment, a subject having high IL-6RA (or "high IL-6RA and diabetes") is a subject having rheumatoid arthritis (or RA and diabetes) and an IL-6 level (e.g., serum level) greater than about 35 pg/ml, e.g., about 35 pg/ml to about 800 pg/ml. Ranges and values intermediate to the above recited ranges and values are also contemplated to be part of the invention.

In another embodiment, a subject having high IL-6RA (or "high IL-6RA and diabetes") is a subject having rheumatoid arthritis (or a subject having RA and diabetes) and a C-reactive protein (CRP) level (e.g., serum level) of greater than about 20 mg/L, e.g., about 20 mg/L; 25 mg/L; 30 mg/L; 35 mg/L; 40 mg/L; 45 mg/L; 50 mg/L; 55 mg/L; 60 mg/L; 65 mg/L; 70 mg/L; 75 mg/L; 80 mg/L; 85 mg/L; 90 mg/L; 95 mg/L; 100 mg/L; 105 mg/L; 110 mg/L; 120 mg/L; 130 mg/L; 140 mg/L; 150 mg/L; 160 mg/L; 170 mg/L; 180 mg/L; 190 mg/L; 200 mg/L; 210 mg/L; 220 mg/L; 230 mg/L; 240 mg/L; 250 mg/L; 260 mg/L; 270 mg/L; 280 mg/L; 290 mg/L; 300 mg/L; 310 mg/L; 320 mg/L; 330 mg/L; 340 mg/L; 350 mg/L; 360 mg/L; 370 mg/L; 380 mg/L; 390 mg/L; or about 400 pg/ml; e.g., between about 15 and about 400 mg/L; between about 20 and about 400 mg/L; between about 25 and about 400 mg/L; between about 30 and about 400 mg/L; between about 35 and about 400 mg/L; between about 40 and about 400 mg/L; between about 45 and about 400 mg/L; between about 50 and about 400 mg/L; between about 55 and about 400 mg/L; between about 60 and about 400 mg/L; between about 65 and about 400 mg/L; between about 70 and about 400 mg/L; between about 75 and about 400 mg/L; between about 80 and about 400 mg/L; between about 85 and about 400 mg/L; between about 90 and about 400 mg/L; between about 95 and about 400 mg/L;

between about 100 and about 400 mg/L; between about 105 and about 400 mg/L; between about 20 and about 350 mg/L; between about 25 and about 350 mg/L; between about 30 and about 350 mg/L; between about 40 and about 350 mg/L; between about 45 and about 350 mg/L; between about 50 and about 350 mg/L; between about 55 and about 350 mg/L; between about 60 and about 350 mg/L; between about 65 and about 350 mg/L; between about 70 and about 350 mg/L; between about 75 and about 350 mg/L; between about 80 and about 350 mg/L; between about 85 and about 350 mg/L; between about 90 and about 350 mg/L; between about 95 and about 350 mg/L; between about 100 and about 350 mg/L; between about 105 and about 350 mg/L; between about 20 and about 300 mg/L; between about 25 and about 300 mg/L; between about 30 and about 300 mg/L; between about 40 and about 300 mg/L; between about 45 and about 300 mg/L; between about 50 and about 300 mg/L; between about 55 and about 300 mg/L; between about 60 and about 300 mg/L; between about 65 and about 300 mg/L; between about 70 and about 300 mg/L; between about 75 and about 300 mg/L; between about 80 and about 300 mg/L; between about 85 and about 300 mg/L; between about 90 and about 300 mg/L; between about 95 and about 300 mg/L; between about 100 and about 300 mg/L; or between about 105 and about 300 mg/L. Ranges and values intermediate to the above recited ranges and values are also contemplated to be part of the invention.

A subject that does not have high interleukin 6 rheumatoid arthritis or high IL-6RA (or "high IL-6RA and diabetes") (e.g., a subject belonging to a second category of RA disease severity, e.g., a subject having a "moderate level of IL-6" (or "medium level of IL-6") or a "low level of IL-6") is, in one embodiment, a subject having RA and a level of IL-6 who less likely to achieve a clinically meaningful response to administration of a human anti-IL-6R antibody, or antigen-binding portion thereof, e.g., sarilumab, as compared to adalimumab, a TNFα inhibitor other than adalimumab (e.g. etanercept or infliximab), or MTX administration; and or who is less likely to achieve a clinically meaningful response to administration of a human anti-IL-6R antibody, or antigen-binding portion thereof, e.g., sarilumab, and MTX administration as compared to MTX and placebo administration.

In another embodiment, a subject that does not have high IL-6RA (or "high IL-6RA and diabetes") (e.g., a subject belonging to a second category of RA disease severity, e.g., a subject having a "moderate level of IL-6" (or "medium level of IL-6") or a "low level of IL-6") is a subject having rheumatoid arthritis (or a subject having RA and diabetes) and an IL-6 level less than about 1.5 times the upper limit of normal (1.5×ULN); less than about 1.75×ULN; less than about 2×ULN; less than about 2.25×ULN; less than about 2.5×ULN; less than about 2.75×ULN; less than about 2.80× ULN; less than about 2.85×ULN; less than about 2.90× ULN; less than about 2.95×ULN; or less than about 3×ULN. In one embodiment, a subject that does not have high IL-6RA (or "high IL-6RA and diabetes") is a subject having rheumatoid arthritis and an IL-6 level less than about 3 times the upper limit of normal (3×ULN); e.g., between about 1×ULN and about 3×ULN. Ranges and values intermediate to the above recited ranges and values are also contemplated to be part of the invention.

In yet another embodiment, a subject that does not have high IL-6RA (or "high IL-6RA and diabetes") (e.g., a subject belonging to a second category of RA disease severity, e.g., a subject having a "moderate level of IL-6" (or "medium level of IL-6") or a "low level of IL-6") is a subject having rheumatoid arthritis (or a subject having RA and diabetes) and a level of IL-6 less than about 35 pg/ml, e.g., about 35 pg/ml, 30 pg/ml, 25 pg/ml, 20 pg/ml, 15 pg/ml, 10 pg/ml, 5 pg/ml, 1 pg/ml, e.g., between about 1 and 35 pg/ml, between about 1 and 30 pg/ml, between about 1 and 25 pg/ml, between about 1 and 20 pg/ml, between about 1 and 15 pg/ml, between about 1 and 10 pg/ml; or between about 1 and 5 pg/ml. In one embodiment, a subject that does not have high IL-6RA (or "high IL-6RA and diabetes") is a subject having rheumatoid arthritis (or RA and diabetes) and a level of IL-6 less than about 35 pg/ml, e.g., between about 1 and 35 pg/ml. Ranges and values intermediate to the above recited ranges and values are also contemplated to be part of the invention.

"Interleukin 6" or "IL-6" is the well-known cytokine secreted by T cells and macrophages that signals through a cell-surface type I cytokine receptor complex consisting of the ligand-binding IL-6Rα chain (CD126), and the signal-transducing component gp130 (also called CD130). CD130 is the common signal transducer for several cytokines including leukemia inhibitory factor (LIF), ciliary neurotropic factor, oncostatin M, IL-11 and cardiotrophin-1, and is almost ubiquitously expressed in most tissues. As IL-6 interacts with its receptor, it triggers the gp130 and IL-6R proteins to form a complex, thus, activating the receptor. These complexes bring together the intracellular regions of gp130 to initiate a signal transduction cascade through certain transcription factors, Janus kinases (JAKs) and Signal Transducers and Activators of Transcription (STATs).

Methods for determining the level of IL-6 in a sample(s) obtained from a subject are well known to one of ordinary skill in the art and include commercially available nucleic acid and protein based assays. Exemplary commercially available protein based assays to determine IL-6 levels include, for example, Quantikine IL-6 Immunoassay (R&D Systems Inc, Minneapolis, Minn., USA); Human IL-6 ELISA Kit (Thermo Fisher/Abcam/Biocompare/Cisbio/GE Healthcare); IL-6 (human) AlphaLISA Detection Kit (PerkinElmer); Bio-Plex Pro Human Cytokine IL-6 Assay (BIO-RAD); MSD—IL-6 Ultra Sensitive Assay (Meso Scale Discovery); ULX—IL-6 Ultrasensitive Singleplex Bead Kit (Invitrogen); and iLite® IL-6 Assay Ready Cells (Euro Diagnostica).

As used herein, the terms "patient" or "subject" refer to human and non-human animals, e.g., veterinary patients. The term "non-human animal" includes all vertebrates, e.g., mammals and non-mammals, such as non-human primates, mice, rabbits, sheep, dog, cat, horse, cow, chickens, amphibians, and reptiles. In one embodiment, the subject is a human, e.g., a pediatric and adult human.

The term "sample" as used herein refers to a collection of similar cells or tissue isolated from a subject, as well as tissues, cells and fluids present within a subject. The term "sample" includes any body fluid (e.g., blood fluids, lymph, gynecological fluids, cystic fluid, urine, ocular fluids and fluids collected by bronchial lavage and/or peritoneal rinsing), or a cell from a subject. In one embodiment, the tissue or cell is removed from the subject. In another embodiment, the tissue or cell is present within the subject. Other subject samples include tear drops, serum, cerebrospinal fluid, feces, sputum and cell extracts. In one embodiment the sample is a blood sample. In another embodiment, the sample is a serum sample. In one embodiment, the biological sample contains protein molecules from the test subject. In another embodiment, the biological sample may contain mRNA molecules from the test subject or genomic DNA molecules from the test subject.

As used herein, the term "Disease Activity Score using 28 joints" or "DAS28" refers to the well-known measure of disease activity in subjects having RA. DAS28 is a composite outcome measure that generally assesses how many joints in the hands, wrists, elbows, shoulders, and knees are swollen and/or tender; the erythrocyte sedimentation rate (ESR) or C reactive protein (CRP) level in the blood to measure the degree of inflammation; the patient's Visual Analogue Score (a simple scale) to assess how they are feeling on that day from 0 (very good) to 10 (very bad). When a DAS28 score includes a level of CRP, the score is referred to as a "DAS28-CRP score." When a DAS28 score includes a level of ESR, the score is referred to as a "DAS28-ESR score." A DAS28 composite score may readily be assessed and calculated by one of ordinary skill in the art using the following formula:

$$DAS28 = 0.56*\sqrt{(TJC28)} + 0.28*\sqrt{(SJC28)} + 0.70*\ln(ESR) + 0.014*GH$$

TJC28: Tender 28-joint count (shoulders, elbows, wrists, MCPs, PIPs including thumb IP, knees)

SJC28: Swollen 28-joint count (shoulders, elbows, wrists, MCPs, PIPs including thumb IP, knees)

ESR: Erythrocyte sedimentation rate (mm/h); C-reactive protein (CRP) may be used as an alternative to ESR GH: Patient's assessment of general health: VAS 1-10 cm (10=maximal activity)

(see, e.g., Aletaha D, Smolen *J. Clin Exp Rheumatol* (2005) 23 (Suppl 39):S100-S108, the entire contents of which are expressly incorporated herein by reference).

The results are combined to produce the DAS28 score, which correlates with the extent of disease activity:

DAS28-CRP <2.6: Disease remission
DAS28-CRP 2.6-3.2: Low disease activity
DAS28-CRP 3.2-5.1: Moderate disease activity
DAS28-CRP >5.1: High disease activity As used herein, the term "Clinical Disease Activity Index" or "CDAI" refers to the well-known measure of disease activity in subjects having RA. CDAI is a composite score and may readily be assessed and calculated by one of ordinary skill in the art using the following formula:

$$CDAI = SJC(28) + TJC(28) + PGA + EGA$$

SJC(28): Swollen 28-Joint Count (shoulders, elbows, wrists, MCPs, PIPs including thumb IP, knees)

TJC(28): Tender 28-Joint Count (shoulders, elbows, wrists, MCPs, PIPs including thumb IP, knees)

PGA: Patient Global disease Activity (patient's self-assessment of overall RA disease activity on a scale 1-10 where 10 is maximal activity)

EGA: Evaluator's Global disease Activity (evaluator's assessment of overall RA disease activity on a scale 1-10 where 10 is maximal activity).

The results are combined to produce the CDAI which correlates with the extent of disease activity:

| Remission | CDAI ≤ 2.8 |
|---|---|
| Low Disease Activity | CDAI > 2.8 and ≤ 10 |
| Moderate Disease Activity | CDAI > 10 and ≤ 22 |
| High Disease Activity | CDAI > 22 |

As used herein, the term "ACR70 response" refers to the well-known measure, based on American College of Rheumatology criteria, of at least a 70% improvement in the number of tender and swollen joints, and a 70% improvement in at least 3 of the following: the patient's global assessment of disease status; the patient's assessment of pain; the patient's assessment of function—measured using the Stanford Health Assessment Questionnaire—the physician's global assessment of disease status; serum C-reactive protein levels.

As used herein, the term "FACIT Fatigue Scale," also referred to as the "Functional Assessment of Chronic Illness Therapy-Fatigue," "FACIT-F," and the like, refers to the well-known measure that is part of a collection of health-related quality of life (HRQOL) questionnaires targeted to the management of chronic illness. The FACIT-F scale ranges from 0-52. The higher the score, the better the quality of life; a score of less than 30 indicates severe fatigue.

As used herein, the terms "SF-36," "Short Form-36," and the like, refer to the well-known 36-item, patient-reported survey of patient health. The SF-36 consists of eight scaled scores, which are the weighted sums of the questions in their section. Each scale is directly transformed into a 0-100 scale on the assumption that each question carries equal weight. The lower the score the more disability or lower quality of life. The higher the score, the less disability or higher quality of life, e.g., a score of zero is equivalent to maximum disability and a score of 100 is equivalent to no disability. The eight sections are physical functioning (PF), bodily pain (BP), role limitations due to physical health problems (RP), role limitations due to personal or emotional problems (RE), general mental health (MH), social functioning (SF), energy/fatigue or vitality (VIT), and general health perceptions (GH). Emotional well-being and vitality are used interchangeably with general mental health and energy/fatigue, respectively.

There are two distinct concepts measured by the SF-36: a physical dimension, represented by the Physical Component Summary (PCS; "SF-36 PCS"), and a mental dimension, represented by the Mental Component Summary (MCS "SF-36 MCS").

As used herein, the terms "Pain Visual Analog Score" or "Pain VAS" Scores refer to the well-known unidimensional measure of pain intensity. It is based on self-reported measures of symptoms that are recorded with a single handwritten mark placed at one point along the length of a 10-cm line that represents a continuum between the two ends of the scale—"no pain" on the left end (0 cm) of the scale and the "worst pain" on the right end of the scale (10 cm). 10 Measurements from the starting point (left end) of the scale to the patients' marks are recorded in centimeters and are interpreted as their pain. A higher score indicates greater pain intensity.

As used herein, the terms "Sleep Visual Analog Score" or "Sleep VAS" Scores refer to the well-known unidimensional measure of sleep. It is based on self-reported measures of symptoms that are recorded with a single handwritten mark placed at one point along the length of a 10-cm line that represents a continuum between the two ends of the scale— "good sleep" on the left end (0 cm) of the scale and the "bad sleep" on the right end of the scale (10 cm). 10 Measurements from the starting point (left end) of the scale to the patients' marks are recorded in centimeters. A higher score indicates greater bad sleep.

"Type 2 diabetes" also referred to herein as "diabetes" is characterized by a combination of peripheral insulin resistance and inadequate insulin secretion by pancreatic beta cells.

A "subject has diabetes" if the subject has a fasting plasma glucose (FPG) level of about 126 mg/dL (about 7.0 mmol/L) or higher; a 2-hour plasma glucose (PG) level of about 200 mg/dL (about 11.1 mmol/L) or higher during a 75-g oral glucose tolerance test (OGTT); a random plasma glucose of about 200 mg/dL (about 11.1 mmol/L) or higher in a subject having symptoms of hyperglycemia or hyperglycemic crisis; and/or a glycosylated hemoglobin A1c (HbA1c) level of about 6.5% or higher.

The term "disease-modifying anti-rheumatic drug" or "DMARD" refers to a group of otherwise chemically unrelated drugs defined by their use in rheumatoid arthritis to, e.g., slow down disease progression.

In one embodiment, a DMARD is a "conventional synthetic DMARD" ("csDMARD"). Exemplary csDMARDs include methotrexate (MTX), hydroxychloroquine, leflunomide, and sulfasalazine.

In one embodiment, a DMARD is a "biological DMARD" ("bDMARD"). In one embodiment, a bDMARD is a tumor necrosis factor (TNF) inhibitor. Non-limiting examples of a TNF inhibitor include, for example, adalimumab, certolizumab pegol, etanercept, golimumab, and infliximab, and a biosimilar of any of the foregoing.

In one embodiment, the bDMARD is a T-cell costimulatory blocker, e.g., a T-lymphocyte-associated antigen 4 (CTLA-4) fusion protein, e.g., abatacept, or a biosimilar thereof; or an anti-CTLA-4 antibody, or antigen-binding portion thereof, or a biosimilar thereof.

In another embodiment, the bDMARD is B cell deleting agent, e.g., an anti-CD20 antibody, or antigen-binding portion thereof, e.g., rituximab, or a biosimilar thereof.

In yet another embodiment, the bDMARD is an IL-6 inhibitor, e.g., an anti-IL-6 receptor antibody or antigen-binding portion thereof, e.g., tocilizumab, or a biosimilar thereof; or an anti-IL-6 antibody or antigen-binding portion thereof, e.g., clazakizumab (formerly ALD518 and BMS-945429), or sirukumab (formerly CNTO-136), or a biosimilar thereof.

In another embodiment, the bDMARD is an IL-1 receptor antagonist (IL1ra), e.g., anakinra.

In one embodiment, the DMARD is a "targeted synthetic DMARD" ("tsDMARD"), such as a Janus kinase (Jak) inhibitor, e.g., tofacitinib and baricitinib.

Joint damage inhibition and/or progression may readily be assessed by one of ordinary skill in the art. For example, in one embodiment, the van der Heijde modified Total Sharp score (mTSS) can be used to show the degree of joint damage (also called structural damage). The mTSS methodology, which is standard in the field of Rheumatoid Arthritis, quantifies the extent of bone erosions for 44 joints and joint space narrowing for 42 joints, with higher scores representing greater damage. The van der Heijde mTSS at a time point is the sum of the scores from both the erosion score and the joint space narrowing score, for a maximum score of 448.

Typically, the progression of structural damage in a subject is measured by the change from Baseline (BL) of the Van der Heijde modified Total Sharp score (mTSS). Baseline (BL) is defined as the score obtained by the subject before being administered with an anti-IL-6R antibody, or antigen-binding portion thereof, according to the disclosure. Change from baseline is defined as the difference existing between the score obtained by the subject at baseline and the score obtained by the subject after being administered the anti-IL-6R antibody, or antigen-binding portion thereof, typically measured after 24 or 52 weeks of treatment. By comparing the mTSS at baseline and after treatment with the anti-IL-6R antibody, or antigen-binding portion thereof, typically at 24 weeks or 52 weeks, it is possible to measure the progression of structural damage in the subject.

As used herein, the term "biosimilar" (of an approved reference product/biological drug, such as a therapeutic protein, e.g., an antibody, or antigen-binding portion thereof) refers to a biologic product that is similar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biosimilar are the same as those of the reference product. In one embodiment, the facility in which the biosimilar is manufactured, processed, packed, or held meets standards designed to assure that the biosimilar continues to be safe, pure, and potent. The reference product may be approved in at least one of the U.S., Europe, or Japan.

II. Methods of the Invention

The present disclosure provides therapeutic methods for treating a subject having rheumatoid arthritis, such as a subject having high IL-6RA. In some embodiments, the subject having high IL6RA also has diabetes. In one embodiment, the subject having high IL-6RA does not have diabetes.

In one aspect, the present disclosure provides a method for treating a subject having rheumatoid arthritis (RA). The method includes determining the level of interleukin 6 (IL-6) in a sample(s) obtained from the subject, and administering to the subject a therapeutically effective amount of a human anti-interleukin 6 receptor (IL-6R) antibody, or antigen-binding portion thereof, if the level of IL-6 in the subject sample(s) is determined to be a high IL-6 level, thereby treating the subject. In one embodiment, the subject having RA also has diabetes. In one embodiment, the subject having RA does not have diabetes.

In another aspect, the present disclosure provides a method for treating a subject having high interleukin 6 rheumatoid arthritis (high IL-6RA). The methods include selecting a subject having high IL-6RA, and administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

In one aspect, the present disclosure provides a method for treating a subject previously identified as having high interleukin 6 rheumatoid arthritis (high IL-6RA). The method includes administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

The present disclosure also provides a method for achieving Disease Activity Score using 28 Joints (DAS28) remission in a subject having high interleukin 6 rheumatoid arthritis (high IL-6RA). The method includes administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

In another aspect, the present disclosure provides a method for achieving Clinical Disease Activity Index (CDAI) remission in a subject having high interleukin 6 rheumatoid arthritis (high IL-6RA). The method includes administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

In yet another aspect, the present disclosure provides a method for achieving an ACR70 response in a subject having high interleukin 6 rheumatoid arthritis (high IL-6RA). The methods include administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

In one aspect, the present disclosure provides a method for treating a subject having rheumatoid arthritis (RA) with a human anti-interleukin 6 receptor (IL-6R) antibody, or antigen-binding portion thereof. The methods include selecting a subject having a high interleukin 6 (IL-6) level, and administering to the subject a therapeutically effective amount of a human anti-interleukin 6 receptor (IL-6R) antibody, or antigen-binding portion thereof, thereby treating the subject. In one embodiment, the subject having RA also has diabetes. In one embodiment, the subject having RA does not have diabetes.

In another aspect, the present disclosure provides a method for inhibiting joint damage in a subject. The methods include selecting a treatment naïve subject having high interleukin 6 rheumatoid arthritis (high IL-6RA), and administering to the subject a therapeutically effective amount of a human anti-interleukin 6 receptor (IL-6R) antibody, or antigen-binding portion thereof, as a monotherapy, thereby inhibiting joint damage in the subject. In one embodiment, the subject having high IL-6RA also has diabetes. In one embodiment, the subject having high IL-6RA does not have diabetes.

In one aspect, the present disclosure provides a method for preventing further joint damage in a subject caused by intolerance or inadequate response to a treatment. The methods include selecting a subject having high interleukin 6 rheumatoid arthritis (high IL-6RA), and administering to the subject a therapeutically effective amount of a human anti-interleukin 6 receptor (IL-6R) antibody, or antigen-binding portion thereof, thereby preventing further joint damage in the subject. In one embodiment, the subject having high IL-6RA also has diabetes. In one embodiment, the subject having high IL-6RA does not have diabetes.

In another aspect, the present disclosure provides a method for treating a subject. The methods include determining whether a subject suspected of having rheumatoid arthritis (RA) has high interleukin 6 rheumatoid arthritis (high IL-6RA), and administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

In yet another embodiment, the present disclosure provides a method for treating a methotrexate-intolerant subject having rheumatoid arthritis (RA). The methods include determining whether the subject has high interleukin 6 rheumatoid arthritis (high IL-6RA), and administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

The present disclosure also provides a method for treating a methotrexate-inadequate responder subject having rheumatoid arthritis (RA). The methods include determining whether the subject has high interleukin 6 rheumatoid arthritis (high IL-6RA), and administering to the subject a therapeutically effective amount of a human anti-interleukin 6 receptor (IL-6R) antibody, or antigen-binding portion thereof, thereby treating the subject. In one embodiment, the subject having high IL-6RA also has diabetes. In one embodiment, the subject having high IL-6RA does not have diabetes.

In one aspect, the present disclosure provides a method of treating a subject having rheumatoid arthritis. The method includes determining the level of IL-6 in a sample(s) from the subject so that the subject is determined to belong to either a first category of rheumatoid arthritis disease severity or a second category of rheumatoid arthritis disease severity; assigning a therapy to the subject if the subject is associated with the first category of rheumatoid arthritis disease severity, wherein the therapy is administration of a therapeutically effective amount of a human IL-6R antibody, or antigen-binding portion thereof; and administering the human IL-6R antibody, or antigen-binding portion thereof, to the subject, thereby treating the subject having rheumatoid arthritis. In one embodiment, the subject having RA also has diabetes. In one embodiment, the subject having RA does not have diabetes.

In another aspect, the present disclosure provides a method of treating subjects having rheumatoid arthritis. The method includes determining the level of IL-6 in serum samples from the subjects so that each subject is determined to belong to either a first category of rheumatoid arthritis disease severity or a second category of rheumatoid arthritis disease severity; assigning a therapy to the subjects in the first category of rheumatoid arthritis disease severity, wherein the therapy is administration of a therapeutically effective amount of a human IL-6R antibody, or antigen-binding portion thereof; and administering the human IL-6R antibody, or antigen-binding portion thereof, to the subjects in the first category of rheumatoid arthritis disease severity, thereby treating the subjects having rheumatoid arthritis. In one embodiment, the subject having RA also has diabetes. In one embodiment, the subject having RA does not have diabetes.

In one embodiment, the first category of rheumatoid arthritis disease severity corresponds to a high level of IL-6.

In one embodiment, the second category of rheumatoid arthritis disease severity corresponds to a moderate level of IL-6 and/or a low level of IL-6.

In another aspect, the present disclosure provides a method of preventing further joint damage caused by intolerance or inadequate response to prior treatment with a DMARD in a subject having rheumatoid arthritis. The methods include selecting a subject having high interleukin 6 rheumatoid arthritis (high IL-6RA), and administering to the subject a therapeutically effective amount of a human anti-interleukin 6 receptor (IL-6R) antibody, or antigen-binding portion thereof, thereby preventing further joint damage in the subject. In one embodiment, the subject having high IL-6RA also has diabetes. In one embodiment, the subject having high IL-6RA does not have diabetes.

Subjects that would benefit from the therapeutic methods of the disclosure include subjects that are suspected of having RA (or RA and diabetes); subjects previously diagnosed as having RA (or RA and diabetes), including treatment naïve RA subjects, subjects previously administered one or more therapeutic agents for treating RA, including DMARD inadequate responder (DMARD-IR) subjects (including DMARD non-responders), DMARD intolerant subjects, TNF inhibitor inadequate responder subjects (including TNF inhibitor non-responders), and TNF inhibitor-intolerant subjects.

In some embodiments, a subject was treated for at least three months with a DMARD and was intolerant or had an inadequate response to the DMARD.

As used herein, a "DMARD-intolerant subject" is a subject having RA and treated with a DMARD, that develops abdominal pain, nausea, vomiting and behavioral symptoms, occurring upon, prior to (anticipatory), and/or when thinking of a DMARD (associative). Such subjects may be intolerant to a csDMARD (e.g., methotrexate, "methotrexate-intolerant subjects" or "MTX-intolerant subjects") or may be intolerant to a bDMARD, e.g., a TNF-inhibitor, e.g., TNF inhibitor, e.g., etanercept, infliximab, adalimumab, golimumab or certolizumab (e.g., TNF-inhibitor-intolerant subjects"). A "DMARD-intolerant subject" may also include subjects that cannot tolerate DMARD doses above a certain amount. For example, a "DMARD-intolerant subject" may be a subject who cannot tolerate a DMARD, e.g., MTX, above a dosage of 25 mg/week. In some embodiments, a "DMARD-intolerant subject" is a subject that cannot tolerate a DMARD, e.g., MTX, at a dosage of 20 mg/week. The upper limit of tolerance for a DMARD, e.g. MTX, may be less than 25 mg/week, e.g., 20 mg/week, 15 mg/week or 10 mg/week.

In one embodiment, a DMARD-intolerant subject is identified by completing the "methotrexate intolerance severity score ("MISS") questionnaire" (Bulatovic, et al. (2011) *Arthritis Rheum.* 15:2007-2013). The MISS consists of four domains: abdominal pain, nausea, vomiting and behavioural symptoms, assessing symptoms after DMARD, e.g., MTX, administration, anticipatory (before DMARD, e.g., MTX) and associative symptoms (when thinking of DMARD, e.g., MTX). The behavioural symptoms domain includes restlessness, irritability and refusal of DMARD, e.g., MTX, which develop in response to DMARD-, e.g., MTX-, induced gastrointestinal symptoms and anticipation thereof. A subject could score 0 (no symptoms), 1 (mild symptoms), 2 (moderate symptoms) or 3 (severe symptoms) points on each item. A DMARD-intolerant subject, e.g., MTX-intolerant subject, is a subject having a MISS score of ≥6, including at least one anticipatory, associative or behavioural symptom.

As used herein, a "DMARD-inadequate responder subject" (e.g., a "methotrexate-inadequate responder subject," "MTX-inadequate responder subject" ("MTXIR") or "TNF-inhibitor-inadequate responder subject") is a subject having RA and treated with a DMARD that still presents as having "active disease" after treatment. Patients present as having active disease when they exhibit at least 8 of 68 tender joints and 6 of 66 swollen joints, and high sensitivity C-reactive protein (hs-CRP) >8 mg/L (>0.8 mg/dL) or erythrocyte sedimentation rate (ESR) ≥28 mm/hours and a 28-joint disease activity score using ESR (DAS28-ESR) of >5.1.

For example, a "DMARD-inadequate responder subject" may have received continuous treatment with a DMARD, e.g., a csDMARD, e.g., MTX, at a dose of about 10 to 25 mg/week (or per local labeling requirements if the dose range differs) for at least 12 weeks and on a stable dose of MTX for a minimum of 8 weeks and still presents a moderate-to-severely active RA, defined as: (i) at least 8 of 68 tender joints and 6 of 66 swollen joints, and (ii) high sensitivity C-reactive protein (hs-CRP) >8 mg/L (>0.8 mg/dL) or erythrocyte sedimentation rate (ESR) ≥28 mm/hours.

In another example, a "DMARD-inadequate responder subject" may not have an improvement in, e.g., chronic disease anemia, fever, depression, fatigue, rheumatoid nodules, vasculitis, neuropathy, scleritis, pericarditis, Felty's syndrome and/or joint destruction, a detectable improvement in ACR20, ACR50, and/or ACR70, or a detectable improvement in a DAS28 score.

In a further example, a "DMARD-inadequate responder subject" may have received continuous treatment with a DMARD, e.g., a bDMARD, e.g., a TNF-inhibitor, e.g., adalimumab, for at least three months and still presents a moderate-to-severely active RA, defined as: (i) at least 8 of 68 tender joints and 6 of 66 swollen joints, and (ii) high sensitivity C-reactive protein (hs-CRP) >8 mg/L (>0.8 mg/dL).

The amount of an anti-IL-6R antibody, or antigen-binding portion thereof, administered to a subject according to the methods of the present disclosure is, generally, a therapeutically effective amount.

As used herein, the phrase "therapeutically effective amount" means an amount of an anti-IL-6R antibody, or antigen-binding portion thereof, that inhibits, prevents, lessens, or delays the progression of RA in a subject, or that results in a detectable improvement in one or more symptoms or indicia of rheumatoid arthritis as described herein, e.g., or which causes a biological effect (e.g., a decrease in the level of a particular biomarker) that is correlated with the underlying pathologic mechanism(s) giving rise to the condition or symptom(s) of rheumatoid arthritis. For example, a dose of an anti-hIL6R antibody which causes an improvement in any of the following symptoms or conditions is deemed a "therapeutically effective amount": chronic disease anemia, fever, depression, fatigue, rheumatoid nodules, vasculitis, neuropathy, scleritis, pericarditis, Felty's syndrome and/or joint destruction. A detectable improvement can also be detected using a clinical measure or a patient reported outcome (PRO). For example, a detectable improvement can be detected using a clinical measure, such as, e.g., the American College of Rheumatism (ACR) rheumatoid arthritis classification criteria. For example a 20% (ACR20), 50% (ACR50) or 70% (ACR70) improvement from baseline can be used to show detectable improvement. The disease activity score (DAS28) can be used to show detectable improvement. In addition, a detectable improvement can be detected using a PRO, such as, e.g., an improvement in a VAS score.

An improvement of physical function and/or mental function may assessed by the change from baseline (BL) in the Health Assessment Questionnaire Disability Index (HAQ-DI), Short Form-36 (SF-36), SF-36 physical health component summary (PCS), SF-36, mental health component summary (MCS), FACIT Fatigue, morning stiffness VAS, Pain VAS, or sleep VAS, or any combination thereof.

Inhibition of the progression of structural damage may be assessed by the change from baseline (BL) in the modified Van der Heijde total Sharp score (mTSS).

A therapeutically effective amount of an anti-IL-6R antibody, or antigen-binding portion thereof, can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-6R antibody. In certain embodiments, 75 mg, 150 mg, 200 mg, or 300 mg of an anti-IL-6R antibody, or antigen-binding portion thereof, is administered to a subject. In other embodiments, The an anti-IL-6R antibody, or antigen-binding portion thereof, e.g., sarilumab, is administered to a subject at between about 50 and 150 mg per week or between about 100 and 200 mg once every two weeks (q2w).

The amount of an anti-IL-6R antibody, or antigen-binding portion thereof, contained within the individual doses may be expressed in terms of milligrams of antibody per kilogram of patient body weight (i.e., mg/kg). For example, an anti-IL-6R antibody, or antigen-binding portion thereof, may be administered to a patient at a dose of about 0.0001 to about 10 mg/kg of patient body weight.

In some embodiments of the invention, the methods include administering to the subject one or more additional therapeutic agents in combination with an anti-IL-6R antibody, or antigen-binding portion thereof, e.g., sarilumab. As used herein, the phrase "in combination with" means that the additional therapeutic agent(s) is administered before, after, or concurrent with the an anti-IL-6R antibody, or antigen-binding portion thereof, e.g., sarilumab, or a pharmaceutical compositions comprising the anti-IL-6R antibody, or antigen-binding portion thereof, e.g., sarilumab.

For example, when administered "before" the anti-IL-6R antibody, or antigen-binding portion thereof, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the anti-IL-6R antibody, or antigen-binding portion thereof. When administered "after" the anti-IL-6R antibody, or antigen-binding portion thereof, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the anti-IL-6R antibody, or antigen-binding portion thereof. Administration "concurrent" with the anti-IL-6R antibody, or antigen-binding portion thereof, means that the additional therapeutic agent is administered to the subject in a separate dosage form within less than 5 minutes (before, after, or at the same time) of administration of the anti-IL-6R antibody, or antigen-binding portion thereof, or administered to the subject as a single combined dosage formulation comprising both the additional therapeutic agent and the anti-IL-6R antibody, or antigen-binding portion thereof.

Examples of additional therapeutic agents which can be administered in combination with an anti-IL-6R antibody, or antigen-binding portion thereof, e.g., sarilumab, in the practice of the methods of the present invention include, but are not limited to NSAIDs, DMARDs, TNFα antagonists, T-cell blockers, CD-20 antagonists (e.g., anti-CD-20 antibodies), IL-1 antagonists, JAK antagonists, IL-17 antagonists, and any other compound known to treat, prevent, or ameliorate rheumatoid arthritis in a human subject. Specific, non-limiting examples of additional therapeutic agents that may be administered in combination with an anti-IL-6R antibody, or antigen-binding portion thereof, in the context of a method of the present invention include, but are not limited to methotrexate, sulfasalazine, hydroxychloroquine, leflunomide, etanercept, infliximab, adalimumab, golimumab, rilonacept, anakinra, abatacept, certolizumab and rituximab. In the present methods, the additional therapeutic agent(s) can be administered concurrently or sequentially with the anti-IL-6R antibody, or antigen-binding portion thereof, e.g., sarilumab. For example, for concurrent administration, a pharmaceutical formulation can be made which contains both an anti-hIL-6R antibody and at least one additional therapeutic agent. The dose of the additional therapeutic agent that is administered in combination with the anti-IL-6R antibody, or antigen-binding portion thereof, in the practice of the methods of the present invention can be easily determined using routine methods known and readily available in the art.

The present disclosure includes methods comprising administering to a subject a pharmaceutical composition comprising an anti-IL-6R antibody, or antigen-binding portion thereof, at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-IL-6R antibody, or antigen-binding portion thereof, once a week dosing at an amount of about 75 mg, 150 mg, 200 mg, or 300 mg, can be employed.

According to certain embodiments of the present disclosure, multiple doses of an anti-IL-6R antibody, or antigen-binding portion thereof, may be administered to a subject over a defined time course. The methods according to this aspect of the disclosure comprise sequentially administering to a subject multiple doses of an anti-IL-6R antibody, or antigen-binding portion thereof. As used herein, "sequentially administering" means that each dose of an anti-IL-6R antibody, or antigen-binding portion thereof, is administered to the subject at a different point in time, e.g., on different days separated by a predetermined interval (e.g., hours, days, weeks or months). The present disclosure includes methods which comprise sequentially administering to the patient a single initial dose of an anti-IL-6R antibody, or antigen-binding portion thereof, followed by one or more secondary doses of the anti-IL-6R antibody, or antigen-binding portion thereof, and optionally followed by one or more tertiary doses of the anti-IL-6R antibody, or antigen-binding portion thereof.

The terms "initial dose," "secondary doses," and "tertiary doses," refer to the temporal sequence of administration of the anti-IL-6R antibody, or antigen-binding portion thereof. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of an anti-IL-6R antibody, or antigen-binding portion thereof, but generally may differ from one another in terms of frequency of administration. In certain embodiments, however, the amount of an anti-IL-6R antibody, or antigen-binding portion thereof, contained in the initial, secondary and/or tertiary doses varies from one another (e.g., adjusted up or down as appropriate) during the course of treatment. In certain embodiments, two or more (e.g., 2, 3, 4, or 5) doses area at the beginning of the treatment regimen as "loading doses" followed by subsequent doses that are administered on a less frequent basis (e.g., "maintenance doses").

In one exemplary embodiment of the present disclosure, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of an anti-IL-6R antibody, or antigen-binding portion thereof, which is administered to a patient prior to the administration of the very next dose in the sequence with no intervening doses.

The methods according to this aspect of the disclosure may comprise administering to a patient any number of secondary and/or tertiary doses of an anti-IL-6R antibody, or antigen-binding portion thereof. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In some embodiments, as a result of the treatment, the subject achieves a 70% improvement in the American College of Rheumatology core set disease index (ACR70) after, e.g., 12 weeks of treatment, or after 24 weeks of treatment, e.g., 200 mg q2w sarilumab treatment.

In some embodiments, as a result of the treatment, the subject achieves DAS28-CRP remission after, e.g., 12 weeks of treatment, or after 24 weeks of treatment, e.g., 200 mg q2w sarilumab treatment.

In some embodiments, as a result of the treatment, the subject achieves CDAI remission after, e.g., 12 weeks of treatment, or after 24 weeks of treatment, e.g., 200 mg q2w sarilumab treatment.

In some embodiments, as a result of the treatment, e.g., 200 mg q2w sarilumab treatment, the subject achieves an inhibition of progression of structural damage at, e.g., week 52, as measured by the change in the modified Van der Heijde total Sharp score (mTSS), e.g., an mTSS score of 0.25.

In some embodiments, as a result of the treatment, e.g., 200 mg q2w sarilumab treatment, the subject achieves a reduction of approximately 90% in the radiographic progression as assessed by the mTSS at, e.g., week 52.

In some embodiments, after at least 24 weeks of treatment, e.g., 200 mg q2w sarilumab treatment, the subject achieves a change from baseline (BL) in the modified Van der Heijde total Sharp score (mTSS) of at most 0.6.

In some embodiments, after at least 52 weeks of treatment, e.g., 200 mg q2w sarilumab treatment, the subject achieves a change from baseline (BL) in the modified Van der Heijde total Sharp score (mTSS) of at most 1.

In some embodiments, after at least 24 weeks of treatment, e.g., 200 mg q2w sarilumab treatment, the subject achieves a change from baseline (BL) in the modified Van der Heijde total Sharp score (mTSS) of at most 0.2.

In some embodiments, after at least 52 weeks of treatment, e.g., 200 mg q2w sarilumab treatment, the subject achieves a change from baseline (BL) in the modified Van der Heijde total Sharp score (mTSS) of at most 0.3.

In some embodiments, after at least 24 weeks of treatment, e.g., 200 mg q2w sarilumab treatment, the subject achieves a clinical improvement in a measure of diabetes, e.g., a reduction in HbA1c, e.g., a decrease of about 0.4% HbA1c level from baseline HbA1c level.

According to certain embodiments of the present disclosure, a patient may exhibit a decrease in the level of one or more of CRP (e.g., high-sensitivity (hs) CRP), serum amyloid A (SAA), ESR and/or hepcidin following administration of an anti-hIL-6R antibody, e.g., 200 mg q2w sarilumab administration. For example, at about week 12 following administration of anti-hIL-6R antibody the subject may exhibit one or more of the following: (i) a decrease in hsCRP by about 40%, 45%, 50%, 55%, 60%, 65%, 70%, 75%, 80%, 85%, 90%, 95% or more; (ii) a decrease in SAA by about 40%, 45%, 50%, 55%, 60%, 65%, 70%, 75%, 80%, 85%, 90%, 95% or more; (iii) a decrease in ESR by about 15%, 20%, 25%, 30%, 35%, 40%, 45%, 50%, 55% or more; and/or (iv) a decrease in hepcidin by about 30%, 35%, 40%, 45%, 50%, 55%, 60%, 65%, 70%, 75% or more.

In some embodiments, as a result of the treatment, e.g., 200 mg q2w sarilumab treatment, the subject achieves an improvement in the American College of Rheumatology (ACR) criterion of C-reactive protein (CRP) levels, e.g., the CRP level decreases by at least 30 mg/dL (e.g., 30, 31, 32, 33, 34, 35, 36, 37, 38, 39, or 40 mg/dL) between the start of treatment and, e.g., at 12 weeks.

III. Interleukin-6 Receptor Antibodies, and Antigen-Binding Portions Thereof, for Use in the Methods of the Disclosure Exemplary anti-IL-6R antibodies are described in U.S. Pat. Nos. 7,582,298; 6,410,691; 5,817,790; 5,795,965; and 6,670,373, the entire contents of each of which are expressly incorporated herein by reference.

As used herein, the term "hIL-6R" refers to a human cytokine receptor that specifically binds human interleukin-6 (IL-6). In certain embodiments, the antibody that is administered to the subject binds specifically to the extracellular domain of hIL-6R. The extracellular domain of hIL-6R is shown in the amino acid sequence of SEQ ID NO:1 The term "antibody," as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-IL-6R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences.

In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody of the present disclosure using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody," as used herein, is intended to include antibodies having variable and constant regions derived from human germline immunoglobulin sequences. The human antibodies of the disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, CH2 or CH3 region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-6R, as used in the context of the present disclosure, includes antibodies that bind IL-6R or portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-6R may, however, have cross-reactivity to other antigens, such as IL-6R molecules from other (non-human) species.

The anti-IL-6R antibodies useful for the methods of the present disclosure may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present disclosure.

The present disclosure also includes methods involving the use of anti-IL-6R antibodies comprising variants of any of the HCVR, LCVR, and/or CDR amino acid sequences disclosed herein having one or more conservative substitutions. For example, the present disclosure includes the use of anti-IL-6R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance," as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "KD," as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Methods for generating human antibodies in transgenic mice are known in the art. Any such known methods can be used in the context of the present disclosure to make human antibodies that specifically bind to human IL-6R.

Using VELOCIMMUNE™ technology (see, for example, U.S. Pat. No. 6,596,541, Regeneron Pharmaceuticals) or any other known method for generating monoclonal antibodies, high affinity chimeric antibodies to IL-6R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the disclosure, for example wild-type or modified IgG1 or IgG4. While the constant region selected may vary according to specific use, high affinity antigen-binding and target specificity characteristics reside in the variable region.

In general, the antibodies that can be used in the methods of the present disclosure possess high affinities, as described above, when measured by binding to antigen either immobilized on solid phase or in solution phase. The mouse constant regions are replaced with desired human constant regions to generate the fully human antibodies of the disclosure. While the constant region selected may vary according to specific use, high affinity antigen-binding and target specificity characteristics reside in the variable region.

Specific examples of human antibodies or antigen-binding fragments of antibodies that specifically bind IL-6R which can be used in the context of the methods of the present disclosure include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs:3, 227, 19, 231, 35, 51, 67, 83, 99, 115, 131, 147, 239, 241, 163, 179, 235, 195 and 211. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs: 11, 229, 27, 233, 43, 59, 75, 91, 107, 123, 139, 155, 171, 187, 203 and 219. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

In certain embodiments of the present disclosure, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs: 3/11; 227/229; 19/27; 231/233; 35/43; 51/59; 67/75; 83/91; 99/107; 115/123; 131/139; 147/155; 239/155; 241; 155; 163/171; 179/187; 235/237; 195/203; and 211/219.

In certain embodiments of the present disclosure, the antibody or antigen-binding fragment thereof comprises HCVR/LCVR amino acid sequence pairs selected from the group consisting of SEQ ID NOs: 3/11; 227/229; 19/27;

231/233; 35/43; 51/59; 67/75; 83/91; 99/107; 115/123; 131/139; 147/155; 239/155; 241; 155; 163/171; 179/187; 235/237; 195/203; and 211/219.

In certain embodiments of the present disclosure, the antibody or antigen-binding fragment thereof comprises an HCVR/LCVR amino acid sequence pair having SEQ ID NOs:19/27, and HCDR1-HCDR2-HCDR3/LCDR1-LCDR2-LCDR3 domains represented by SEQ ID NOs:21-23-25/SEQ ID NOs:29-31-33. Such an antibody may also be referred to as "mAb1" or mAb1 (VQ8F11-21)

It is to be understood that, the methods of the present disclosure can be practiced using any anti-IL-6R antibody disclosed herein, as well as variants and antigen-binding fragments of such antibody.

IV. Pharmaceutical Compositions

The present disclosure includes methods which comprise administering an anti-IL-6R antibody, or antigen-binding portion thereof, to a subject, wherein the an anti-IL-6R antibody, or antigen-binding portion thereof, is contained within a pharmaceutical composition. The pharmaceutical compositions of the disclosure are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present disclosure may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-6R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL6R antibodies, and administration regimens involving the same, that can be used in the context of the present disclosure are disclosed elsewhere herein.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, *CRC Crit. Ref Biomed. Eng.* 14:201). In another embodiment, polymeric materials can be used; see, *Medical Applications of Controlled Release*, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-6R antibody that can be used in the context of the present disclosure are disclosed, e.g., in US Patent Application Publication Nos. 2011/0171241 and 2016/0002341, the entire contents of each of which are incorporated herein by reference.

In certain embodiments, a pharmaceutical formulation for use in the methods of the present disclosure comprises one or more excipients. The term "excipient," as used herein, means any non-therapeutic agent added to the formulation to provide a desired consistency, viscosity or stabilizing effect.

In certain embodiments, the pharmaceutical formulation of the disclosure comprises at least one amino acid. Exemplary amino acids suitable for use in the formulations of the present disclosure include, inter alia, arginine and/or histidine.

The amount of amino acid contained within the pharmaceutical formulations of the present disclosure may vary depending on the specific properties desired of the formulations, as well as the particular circumstances and purposes for which the formulations are intended to be used. In certain embodiments, the formulations may contain about 1 mM to about 200 mM of an amino acid; about 2 mM to about 100 mM of an amino acid; about 5 mM to about 50 mM of an amino acid; or about 10 mM to about 25 mM of an amino acid. For example, the pharmaceutical formulations of the present disclosure may comprise about 1 mM; about 1.5 mM; about 2 mM; about 2.5 mM; about 3 mM; about 3.5 mM; about 4 mM; about 4.5 mM; about 5 mM; about 5.5 mM; about 6 mM; about 6.5 mM; about 7 mM; about 7.5 mM; about 8 mM; about 8.5 mM; about 9 mM; about 9.5 mM; about 10 mM; about 10.5 mM; about 11 mM; about 11.5 mM; about 12 mM; about 12.5 mM; about 13 mM; about 13.5 mM; about 14 mM; about 14.5 mM; about 15 mM; about 15.5 mM; about 16 mM; about 16.5 mM; about 17 mM; about 17.5 mM; about 18 mM; about 18.5 mM; about 19 mM; about 19.5 mM; about 20 mM; about 20.5 mM; about 21 mM; about 21.5 mM; about 22 mM; about 22.5 mM; about 23 mM; about 23.5 mM; about 24 mM; about 24.5 mM; about 25 mM; about 25.5 mM; about 26 mM; about 26.5 mM; about 27 mM; about 27.5 mM; about 28 mM; about 28.5 mM; about 29 mM; about 29.5 mM; about 30 mM; about 35 mM; about 40 mM; about 45 mM; or about 50 mM of an amino acid (e.g., histidine and/or arginine).

The pharmaceutical formulations of the present disclosure may also comprise one or more carbohydrate, e.g., one or more sugar. The sugar can be a reducing sugar or a non-reducing sugar. "Reducing sugars" include, e.g., sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose. Non-reducing sugars can comprise an anomeric carbon that is an acetal and is not substantially reactive with amino acids or polypeptides to initiate a Maillard reaction. Specific examples of non-reducing sugars include sucrose, trehalose, sorbose, sucralose, melezitose and raffinose. Sugar acids include, for example, saccharic acids, gluconate and other polyhydroxy sugars and salts thereof.

The amount of sugar contained within the pharmaceutical formulations of the present disclosure will vary depending on the specific circumstances and intended purposes for which the formulations are used. In certain embodiments, the formulations may contain about 0.1% to about 20% sugar; about 0.5% to about 20% sugar; about 1% to about 20% sugar; about 2% to about 15% sugar; about 3% to about 10% sugar; about 4% to about 10% sugar; or about 5% to about 10% sugar. For example, the pharmaceutical formulations of the present disclosure may comprise about 0.5%; about 1.0%; about 1.5%; about 2.0%; about 2.5%; about 3.0%; about 3.5%; about 4.0%; about 4.5%; about 5.0%; about 5.5%; about 6.0%; 6.5%; about 7.0%; about 7.5%; about 8.0%; about 8.5%; about 9.0%; about 9.5%; about 10.0%; about 10.5%; about 11.0%; about 11.5%; about 12.0%; about 12.5%; about 13.0%; about 13.5%; about 14.0%; about 14.5%; about 15.0%; about 15.5%; about 16.0%; 16.5%; about 17.0%; about 17.5%; about 18.0%; about 18.5%; about 19.0%; about 19.5%; or about 20.0% sugar (e.g., sucrose).

The pharmaceutical formulations of the present disclosure may also comprise one or more surfactant. As used herein, the term "surfactant" means a substance which reduces the surface tension of a fluid in which it is dissolved and/or reduces the interfacial tension between oil and water. Surfactants can be ionic or non-ionic. Exemplary non-ionic surfactants that can be included in the formulations of the present disclosure include, e.g., alkyl poly(ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants that can be included in the formulations of the present disclosure include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 188, poloxamer 407; polyethylene-polypropylene glycol; or polyethylene glycol (PEG). Polysorbate 20 is also known as TWEEN 20, sorbitan monolaurate and polyoxyethylenesorbitan monolaurate.

The amount of surfactant contained within the pharmaceutical formulations of the present disclosure may vary depending on the specific properties desired of the formulations, as well as the particular circumstances and purposes for which the formulations are intended to be used. In certain embodiments, the formulations may contain about 0.05% to about 5% surfactant; or about 0.1% to about 0.2% surfactant. For example, the formulations of the present disclosure may comprise about 0.05%; about 0.06%; about 0.07%; about 0.08%; about 0.09%; about 0.10%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; or about 0.30% surfactant (e.g., polysorbate 20).

The pharmaceutical formulations of the present disclosure may have a pH of from about 5.0 to about 8.0. For example, the formulations of the present disclosure may have a pH of about 5.0; about 5.2; about 5.4; about 5.6; about 5.8; about 6.0; about 6.2; about 6.4; about 6.6; about 6.8; about 7.0; about 7.2; about 7.4; about 7.6; about 7.8; or about 8.0.

In one embodiment, a pharmaceutical formulation for use in the methods of the disclosure comprises: (i) a human antibody that specifically binds to human anti-IL-6R antibody, or antigen-binding portion thereof; (ii) an amino acid (e.g., histidine); and (iii) a sugar (e.g., sucrose).

In another embodiment of the present disclosure, a pharmaceutical formulation for use in the methods of the disclosure comprises: (i) a human antibody that specifically binds to human anti-IL-6R antibody, or antigen-binding portion thereof; (ii) an amino acid (e.g., histidine); (iii) a sugar (e.g., sucrose); and (iv) a surfactant (e.g., polysorbate 20).

In another embodiment of the present disclosure, a pharmaceutical formulation for use in the methods of the disclosure comprises: (i) a human antibody that specifically binds to human anti-IL-6R antibody, or antigen-binding portion thereof; (ii) a first amino acid (e.g., histidine); (iii) a sugar (e.g., sucrose); (iv) a surfactant (e.g., polysorbate 20); and (v) a second amino acid (e.g., arginine).

In one embodiment, the pharmaceutical composition comprises about 200 mg sarilumab, about 45 mM arginine, about 21 mM histidine, about 0.2% w/v polysorbate-20, and about 5% w/v sucrose. In one embodiment, the pH of the pharmaceutical composition is about 6.0.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

Example 1. High Baseline Serum IL-6 Identifies a Subgroup of Rheumatoid Arthritis (RA) Patients with Rapid Joint Damage and Clinical Progression and Predicts Sarilumab Treatment Response Despite the key role of IL-6 in RA, there are limited data on IL-6 as a predictor of prognosis or treatment response in RA. A post hoc analysis of the Phase 3 MOBILITY study (NCT01061736) was conducted to investigate whether patients with high levels of IL-6 have a differential response to sarilumab+MTX compared to MTX treatment across different outcomes. Details of the MOBILITY clinical trial are described elsewhere (see, for example, U.S. Patent Application Publication 2013/0149310, and Genovese, M et al., Arthritis & Rheumatology 2015, 67(6): 1424-1437, the entire contents of which are incorporated herein by reference).

Morning serum IL-6 levels were measured at baseline in 1193 patients randomized to sarilumab (SC 150 or 200 mg q2w)+MTX or placebo (PBO)+MTX. Normal IL-6 was <12.5 pg/ml in the assay used. Comparisons were made within and between treatment groups for radiographic and clinical efficacy endpoints based on tertiles of baseline IL-6 levels, using linear and logistic regression.

85% of patients in the high tertile had IL-6≥23×ULN; all patients in the low tertile had normal IL-6. At baseline, patients with high IL 6 levels had significantly more joint damage, greater disease activity and elevated levels of CRP compared with low or medium IL-6 groups (Table 1). Over 52 weeks, on PBO+MTX, patients with high IL-6 were more likely to develop joint damage (Table 2; FIG. 1) versus low IL-6 (mean±SD mTSS progression 4.67±9.80 versus 1.51±5.25 (FIG. 1); Odds Ratio (OR) mTSS, 95% Confidence Interval (CI) 3.3 [1.9, 5.6]). The magnitude of sarilumab+MTX clinical and radiographic efficacy versus PBO+MTX improved with increasing levels of baseline IL-6 at Weeks 24 and 52. ORs at Week 52 are shown in Table 1. The incidence of treatment emergent adverse events was similar across IL-6 tertiles.

TABLE 1

| MOBILITY (pts with an inadequate response to MTX) | | | | |
|---|---|---|---|---|
| | High IL-6 (N = 398) | Medium IL-6 (N = 398) | Low IL-6 (N = 397) | P value |
| Sarilumab 150 mg q2w/200 mg q2w/PBO q2w (all + MTX), n | 146/121/131 | 129/147/122 | 126/128/143 | |
| IL-6 level (pg/ml), median [range] | 61.0 [31.2-648.7] | 17.3 [9.8-30.7] | 5.0 [1.6-9.6] | |
| Baseline disease activity, mean (SD) | | | | |
| CRP (mg/L) | 36.4 (30.1) | 18.3 (15.5) | 10.5 (11.6) | * |
| HAQ-DI | 1.8 (0.7) | 1.6 (0.6) | 1.6 (0.6) | * |
| DAS28-CRP | 6.3 (0.8) | 5.9 (0.8) | 5.6 (0.8) | * |
| mTSS | 56.7 (65.7) | 49.8 (62.1) | 40.8 (56.5) | * |
| CDAI | 43.0 (12.4) | 40.1 (12.3) | 38.3 (11.6) | * |
| Mantel-Haenszel odds ratio (95% CI) sarilumab 200 mg q2w + MTX versus PBO + q2w MTX (Week 52) | | | | |
| mTSS progression | 0.3 (0.1, 0.4) | 0.6 (0.4, 1.0) | 0.7 (0.4, 1.1) | ** |
| ACR20 | 4.9 (2.8, 8.3) | 3.3 (1.9, 5.7) | 1.9 (1.2, 3.2) | ** |
| ACR50 | 6.4 (3.5, 11.8) | 3.4 (1.9, 6.2) | 2.0 (1.2, 3.4) | ** |
| ACR70 | 7.3 (3.3, 16.3) | 3.5 (1.7, 7.4) | 1.9 (1.0, 3.8) | ** |
| DAS28-CRP < 2.6 | 39.3 (9.4, 163.9) | 4.4 (2.2, 8.9) | 2.5 (1.4, 4.7) | ** |
| CDAI ≤ 2.8 | 42.4 (4.7, 383.4) | 3.9 (1.6, 9.5) | 1.8 (0.8, 4.0) | ** |
| HAQ-DI improvement ≥ 0.3 (Wk 16) | 3.1 (1.8, 5.2) | 2.2 (1.3, 3.7) | 1.1 (0.7, 1.8) | ** |

*Kruskal-Wallis test $P < 0.05$ and **nominal $P < 0.05$ for (high vs low) tertile IL-6-by-treatment interaction (logistic regression with treatment, study randomization stratification factors [prior biological use and region], tertile IL-6 at baseline, and tertile IL-6 at baseline-by-treatment interaction as fixed effects)

TABLE 2

| Mean change (SD) in mTSS | | Low IL-6 | Medium IL-6 | High IL-6 |
|---|---|---|---|---|
| Week 24 | Placebo + MTX | 0.54 (3.12) | 1.14 (3.82) | 2 (4.78) |
| | Sarilumab 200 mg q2w + MTX | −0.01 (2.05) | 0.06 (2.79) | 0.39 (2.9) |
| Week 52 | Placebo + MTX | 1.51 (5.25) | 2.29 (7.45) | 4.67 (9.8) |
| | Sarilumab 200 mg q2w + MTX | 0.11 (3.49) | −0.06 (5.51) | 0.77 (4.48) |

In summary, high baseline IL-6 levels predicted faster and substantially more radiographic progression in the PBO+MTX group. Efficacy was greater with sarilumab+MTX versus PBO+MTX in all tertiles. The magnitude of treatment difference with sarilumab+MTX was greater in patients with high versus normal baseline IL-6 in terms of preventing radiographic evidence of progression at Week 24 and 52 and other clinical endpoints which include and exclude acute-phase reactants.

Example 2. Elevated Serum Baseline IL-6 Differentiates Sarilumab and Adalimumab Treatment Response: Using Precision Medicine for Treatment Selection in Rheumatoid Arthritis (RA)

There remains a great need for predictive biomarkers to guide treatment decisions in patients with RA. A post-hoc analysis of the randomized 24-week MONARCH trial (NCT02332590) was conducted to determine whether baseline IL-6 levels were associated with differential response to sarilumab versus adalimumab monotherapy. Details of the MONARCH clinical trial are described elsewhere (see, for example, Burmester G R, Lin Y, Patel R, et al. Ann Rheum Dis 2017; 76:840-847,], the entire contents of which are incorporated herein by reference).

Patients who received adalimumab 40 mg q2w (every two weeks) or sarilumab 200 mg q2w subcutaneously and consented to biomarker assessment were grouped into tertiles based on pre-dose serum IL-6 level (normal level is <12.5 pg/ml). IL-6 data were available in 300 of the 369 patients in the MONARCH ITT (intent to treat) population. Efficacy was compared between the two treatments and within treatment groups according to baseline IL-6 tertile for Week 24 endpoints (ACR20/50/70, DAS28-CRP and -ESR, CDAI, joint counts, HAQ-DI) using linear and logistic regression.

All patients in the high tertile had elevated IL-6 level ≥3×ULN and all patients in the low tertile had normal IL-6 level (Table 3). More patients achieved response on sarilumab compared with adalimumab in each tertile across endpoints that include and exclude acute phase reactants, however, the treatment difference was greatest in patients with high baseline IL-6 versus low baseline IL-6; Wk 24 ACR70 was 30.4% (sailumab) vs 3.7% (adalimumab) in the high tertile and 18.2% vs 17.8%, respectively, in the low tertile (Table 3). High baseline IL-6 also significantly impacted differences in swollen joint count and CRP reduction between sarilumab and adalimumab. Within the adalimumab treatment group, significantly fewer responses were achieved in patients with elevated vs normal IL-6 (high vs low tertile) for ACR70 and DAS28, and numerically fewer for CDAI. The incidence of treatment emergent adverse events was similar across IL-6 tertiles These results show that patients with elevated baseline IL-6 levels had greater clinical response to sarilumab vs adalimumab monotherapy.

TABLE 3

| MONARCH (pts with an intolerance or inadequate response to MTX) | | | | |
|---|---|---|---|---|
| | High IL-6 (N = 100) | Medium IL-6 (N = 100) | Low IL-6 (N = 100) | P value |
| Sarilumab/adalimumab, n | 46/54 | 47/53 | 55/45 | |
| IL-6 level (pg/ml), median [range] | 64.7 [39.6-692.3] | 16.2 [7.2-39.5] | 2.4 [1.6-7.1] | |
| Baseline disease activity, mean (SD) | | | | |
| CRP (mg/L) | 41.5 (34.1) | 15.2 (17.1) | 5.6 (9.2) | |
| HAQ-DI | 1.8 (0.6) | 1.6 (0.6) | 1.5 (0.6) | * |
| DAS28-CRP | 6.5 (0.8) | 6.0 (0.7) | 5.5 (0.8) | * |
| CDAI | 46.0 (12.2) | 42.9 (11.4) | 40.6 (11.7) | * |
| Mantel-Haenszel odds ratio (95% CI) sarilumab versus adalimumab (Week 24) | | | | |
| ACR20 | 6.6 (2.3, 18.6) | 1.2 (0.5, 3.0) | 1.4 (0.6, 3.1) | ** |
| ACR50 | 5.5 (2.3, 13.2) | 1.5 (0.6, 3.5) | 1.6 (0.7, 3.7) | ** |
| ACR70 | 10.5 (2.3, 48.4) | 1.7 (0.6, 4.6) | 1.1 (0.4, 3.2) | ** |
| DAS28-ESR < 2.6 | 33.9 (3.5, 328.7) | 5.6 (1.6, 19.4) | 1.5 (0.5, 4.4) | ** |
| DAS28-ESR < 3.2 | 10.5 (3.5, 31.4) | 5.1 (1.8, 14.1) | 2.6 (1.0, 6.7) | |
| DAS28-CRP < 2.6 | 18.4 (3.8, 90.0) | 4.0 (1.5, 10.9) | 2.0 (0.8, 5.3) | ** |
| DAS28-CRP < 3.2 | 9.2 (3.4, 24.8) | 2.2 (1.0, 5.1) | 3.2 (1.3, 7.6) | |
| CDAI ≤ 10 | 3.6 (1.4, 9.0) | 1.6 (0.7, 3.7) | 3.1 (1.2, 7.7) | |
| HAQ-DI improvement ≥ 0.3 | 4.5 (1.8, 10.9) | 1.4 (0.6, 3.2) | 1.4 (0.6, 3.2) | ** |

*Kruskal-Wallis test P < 0.05 and **nominal P < 0.05 for (high vs low) tertile IL-6-by-treatment interaction (logistic regression with treatment, study randomization stratification factors [prior biological use and region], tertile IL-6 at baseline, and tertile IL-6 at baseline-by-treatment interaction as fixed effects)

In summary, patients with high baseline IL-6 levels showed greater treatment efficiency with sarilumab vs. adalimumab. High baseline IL-6 level patients had greater reductions in swollen joint count and CRP levels as well as greater response for ACR70, DAS28, and CDAi scores when treated with sarilumab as compared to the adalimumab group.

Example 3. High Baseline Serum IL-6 Identifies a Subgroup of Rheumatoid Arthritis Progression and Predicts Increased Sarilumab Treatment Response Abstract
Background/Purpose:
Clinical application of biomarkers to predict response to therapy is the next frontier in RA. Despite the key role of IL-6 in RA, the utility of IL-6 to predict prognosis or treatment response in RA is limited. Post-hoc analyses of MOBILITY (NCT01061736) and MONARCH (NCT02332590) studies investigated if serum baseline IL-6 level was associated with radiographic and clinical responses to sarilumab versus comparator treatment.

Methods:
Baseline IL-6 levels were measured using a validated assay in 1193 patients (pts) randomized to sarilumab (SC (subcutaneous) 150 mg or 200 mg q2w)+MTX or placebo (PBO)+MTX, and 300 randomized to sarilumab 200 mg or adalimumab 40 mg q2w. Efficacy was compared between and within treatment groups according to baseline IL-6 tertile using linear and logistic regression.

Results:
All low tertile pts had normal IL-6 levels (<12.5 pg/mL) and >85% of high tertile pts had IL-6 levels 3×ULN. At baseline, pts in the high tertile had more joint damage, greater disease activity, and elevated levels of CRP vs the low tertile pts (nominal P<0.05). In the MOBILITY PBO+MTX group, pts in the high tertile developed more joint damage than pts in the low tertile (mean±SD mTSS progression 4.67±9.80 vs 1.51±5.25; odds ratio 3.3; 95% CI 1.9, 5.6).

Clinical and radiographic efficacy (sarilumab+MTX vs PBO+MTX) in MOBILITY improved with increasing baseline IL-6 tertile. In MONARCH, sarilumab efficacy vs adalimumab was greater in the high vs low tertile-ACR20/70 for sarilumab vs adalimumab: 89%/30% vs 52%/4% [high tertile] and 64%/18% vs 58%/18% [low tertile]. Data show that high IL6 is better than high CRP at predicting efficacy outcomes. The incidence of treatment emergent adverse events was similar across IL-6 tertiles.

Conclusion:
Across clinical and radiographic endpoints, pts with elevated baseline IL-6 levels had greater response to sarilumab compared with MTX or adalimumab than pts with normal IL-6 levels.

Background and Objectives
Clinical tools, including biomarkers, are not currently available in rheumatology practice to predict response prior to initiating or switching biologic therapies.

Given the multitude of approved biologics for rheumatoid arthritis (RA) therapy, additional tools will enable physicians to identify patients who may differentially benefit from one therapy (or mechanism of action) over another.

Obstacles to achieving precision medicine for individual RA patients include: inconsistency of predictive biomarkers identified in clinical studies; lack of translatability to real-world patient care.

The Phase 3 MOBILITY and MONARCH studies investigated the efficacy and safety of the anti-IL-6R mAb sarilumab in patients with RA (Genovese M C, et al. Arthritis Rheumatol 2015; 67:1424-37; Burmester G R, et al. Ann Rheum Dis 2017; 76:840-7).

In these studies, evaluation of baseline interleukin-6 (IL-6) was carried out prior to initiation of therapy for the following reasons: patients with RA have elevated levels of IL-6 in serum and synovial fluid compared with healthy individuals (Robak T, et al. Mediators Inflamm 1998; 7:347-53; Park Y J, et al. Sci Rep 2016; 6:35242); targeting IL-6 signaling reduces radiographic progression, improves signs and symptoms of RA, and increases patients' quality of life (June R R, et al. *Expert Opin Biol Ther* 2016; 16:1303-9).

Data on serum IL-6 levels as a predictor of prognosis or treatment response have been inconclusive to date (Shimamoto K, et al. J Rheumatol 2013; 40; 1074-81; Uno K, et al. PLoS One 2015; 10:e0132055; Diaz-Torne C, et al. Semin Arthritis Rheum 2018; 47:757-64; Nishina N, et al. Arthritis Rheumatol 2017; 69 (Suppl 10): abs 1426; Wang J, et al. BMJ Open 2013; 3:e003199).

The objective of this study was to determine whether baseline IL-6 levels in serum could predict differential response to anti-IL-6R therapy, compared with either methotrexate (MTX) alone or adalimumab, in patients enrolled in the Phase 3 MOBILITY and MONARCH studies Methods
The study designs have been described previously (Genovese M C, et al. Arthritis Rheumatol 2015; 67:1424-37; Burmester G R, et al. Ann Rheum Dis 2017; 76:840-7).

Briefly:
MOBILITY (MTX-IR patients) compared subcutaneous (SC) sarilumab 150 or 200 mg every two weeks (q2w) with placebo over 52 weeks in patients receiving background MTX; and MONARCH (MTX-IR/INT, bDMARD naive patients) compared SC sarilumab 200 mg q2w with adalimumab 40 mg q2w over 24 weeks as monotherapy.

These post-hoc analyses were performed on the biomarker population, encompassing all randomized patients who signed, and did not later withdraw, the informed consent for future use of samples (MONARCH study), with at least one evaluable biomarker sample at baseline collected pre-dose.

Patients were divided into tertiles based on baseline (pre-dose) IL-6 or C-reactive protein (CRP) levels (high, medium, or low) in the biomarker population (see FIG. 3 for ranges).

Approximately 90% of the serum samples were collected in the morning (before 12:00 pm).

Serum IL-6 was measured using a validated ELISA (Quantikine R&D) at Covance Central Labs; the intra-assay precision was ≤9% CV; the inter-assay precision was ≤12%, and the reportable range was 3.12-153,600 pg/mL. The normal value of IL-6 identified by the assay vendor was <12.5 pg/mL (Fraunberger P, et al. Clin Chem Lab Med 1998; 36:797-801).

As a comparison, CRP was measured using the high-sensitivity CRP (Siemens) assay at Covance Central Labs; the intra-assay coefficient of variation (CV) was <3%, the inter-assay CV was <5%; the reference values for healthy controls were ≤2.87 mg/L.

Disease activity and patient-reported outcomes were analyzed

Statistical Methods
The ability of IL-6 to predict response was tested using a logistic regression with treatment, study randomization stratification factors (region for both studies and prior biologic use for MOBILITY), IL-6 tertile at baseline, and IL-6 tertile at baseline-by-treatment interaction as fixed effects.

P-values for the interaction for each sarilumab group vs placebo were calculated using the low tertile as reference.

Pairwise comparisons of efficacy endpoints between sarilumab and placebo were performed separately in each IL-6 tertile, and the Mantel-Haenszel estimate (stratified by randomization factors) of odds ratio (OR) and corresponding 95% confidence intervals (CIs) were derived by testing each dose group vs placebo. A similar analysis was performed on CRP tertiles to compare predictive properties.

The incidence of treatment-emergent adverse events in each IL-6 tertile was analyzed descriptively.

Results

Serum IL-6 was measured at baseline in 1193 patients (>99% intention-to-treat [ITT] population) in MOBILITY and in 300 patients (82% ITT population) in MONARCH.

In each study, all patients in the low baseline IL-6 tertile had normal IL-6 levels (<12.5 pg/mL).

In the high baseline IL-6 tertile, 85% and 100% of patients in MOBILITY and MONARCH, respectively, had IL-6 levels ≥3× the upper limit of normal (FIG. 3).

At baseline, patients in the high IL-6 tertile had significantly higher disease activity (both studies) and significantly more joint damage (MOBILITY), compared with patients in the low IL-6 tertile.

Given the correlation between IL-6 and CRP in each study (Rho=0.71 in MONARCH and 0.58 in MOBILITY), patients in the high IL-6 tertile had significantly elevated CRP compared to patients in the low IL-6 tertile.

MOBILITY—Radiographic Progression

To determine whether baseline IL-6 levels affected progression of joint damage, patients in the MOBILITY study were evaluated by X-ray over 52 weeks.

In the overall ITT group, patients who received placebo+MTX progressed more significantly than patients in either the 150 mg or 200 mg sarilumab treatment group (mean change from baseline in modified total Sharp score [mTSS] 2.78, 0.90, and 0.25, respectively) (Genovese M C, et al. Arthritis Rheumatol 2015; 67:1424-37).

Figure 4:
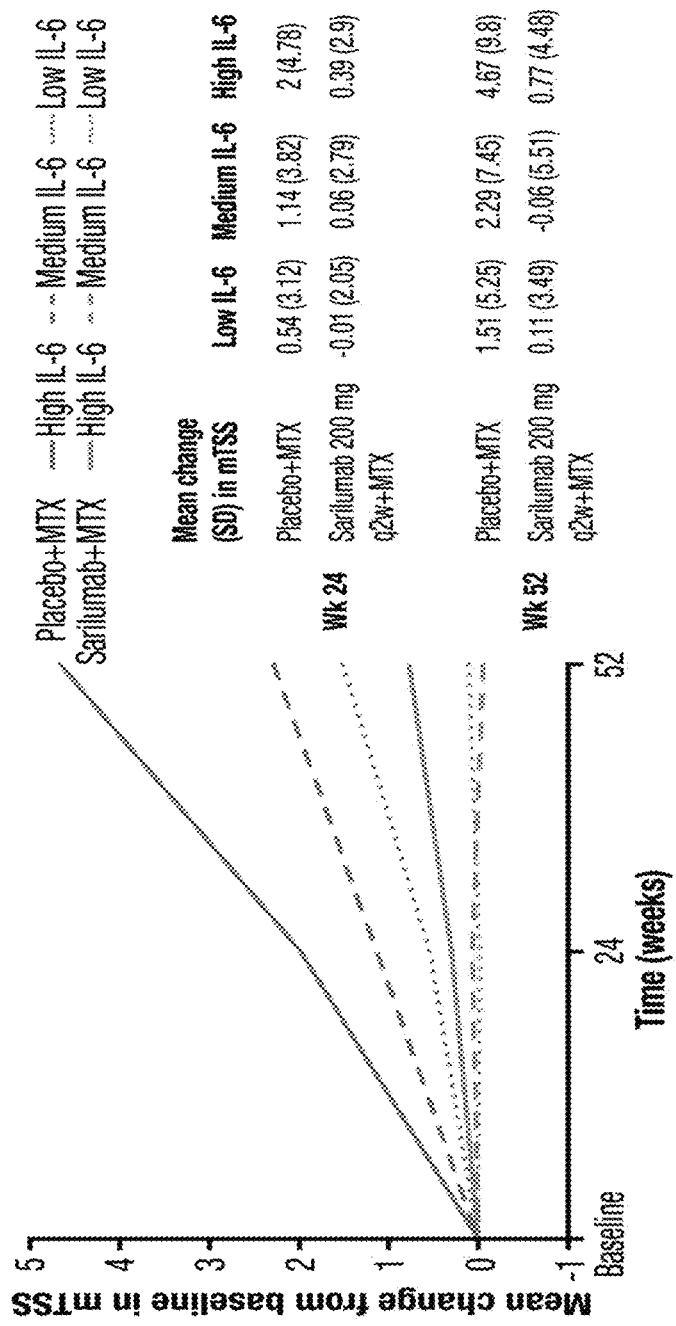
FIG. 4 is a graph depicting the mean change in mTSS according to baseline IL-6 tertile in the subjects in the MOBILITY study.

When assessing patients according to baseline IL-6 levels, placebo+MTX-treated patients in the high IL-6 tertile developed significantly more joint damage over 52 weeks than patients in the low tertile (mean±SD mTSS progression 4.67±9.80 vs 1.51±5.25 [FIG. 4]; OR [95% CI] of the progression defined by a change in mTSS >0: 3.3 [1.9, 5.6]).

The progression experienced by patients in the high IL-6 tertile was more consistent with the level of joint damage in patients with early RA (Smolen J S, et al. Ann Rheum Dis 2009; 68:823-27; Breedveld F C, et al. Arthritis Rheum 2006; 54:26-37), despite this study evaluating more established RA patients. Placebo+MTX-treated patients with high baseline IL-6 experienced more erosion and joint space narrowing (JSN) over 52 weeks than those with low IL-6 (OR [95% CI] for JSN 2.6 [1.6, 4.3]; OR [95% CI] for erosion score: 3.2 [2.0, 5.4]).

Patients treated with sarilumab+MTX demonstrated less joint damage across all IL-6 tertiles compared with those treated with placebo+MTX.

Sarilumab+MTX-treated patients in the low and medium IL-6 tertiles experienced minimal or no joint damage change over the 52 weeks of treatment (FIG. 4).

MOBILITY—Signs, Symptoms, and Disability

Figure 5:
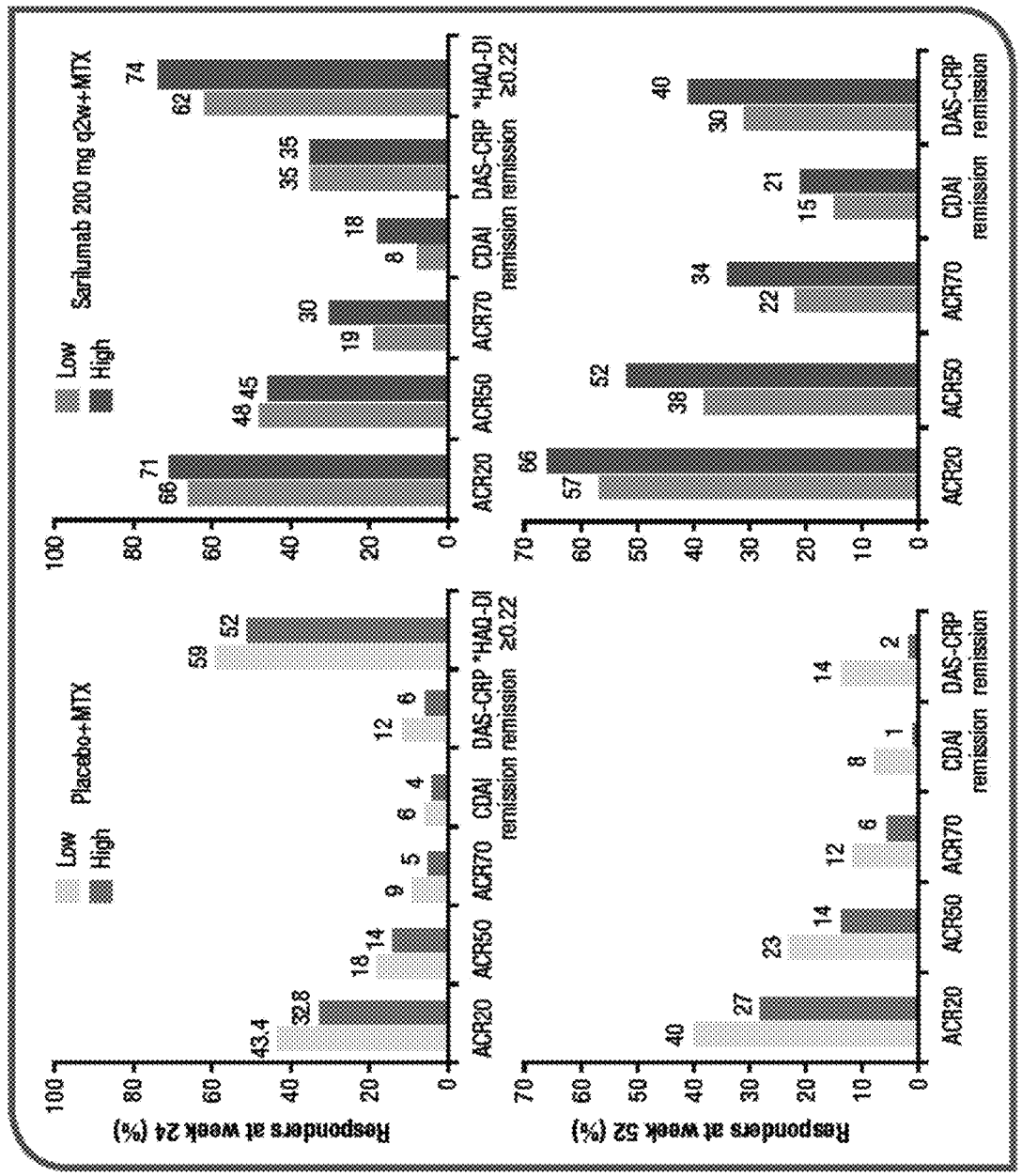
FIG. 5 are graphs depicting 24- and 52-week efficacy according to baseline IL-6 tertile in the subjects in the MOBILITY study.

Although the clinical efficacy of sarilumab was similar across IL-6 tertiles, efficacy decreased numerically in patients with high IL-6 compared with low IL-6 in the placebo+MTX group (FIG. 5)

In addition, placebo+MTX-treated patients with high baseline IL-6 were much less likely to respond compared to sarilumab+MTX-treated patients (FIG. 6).

MONARCH—Efficacy

Figure 7:
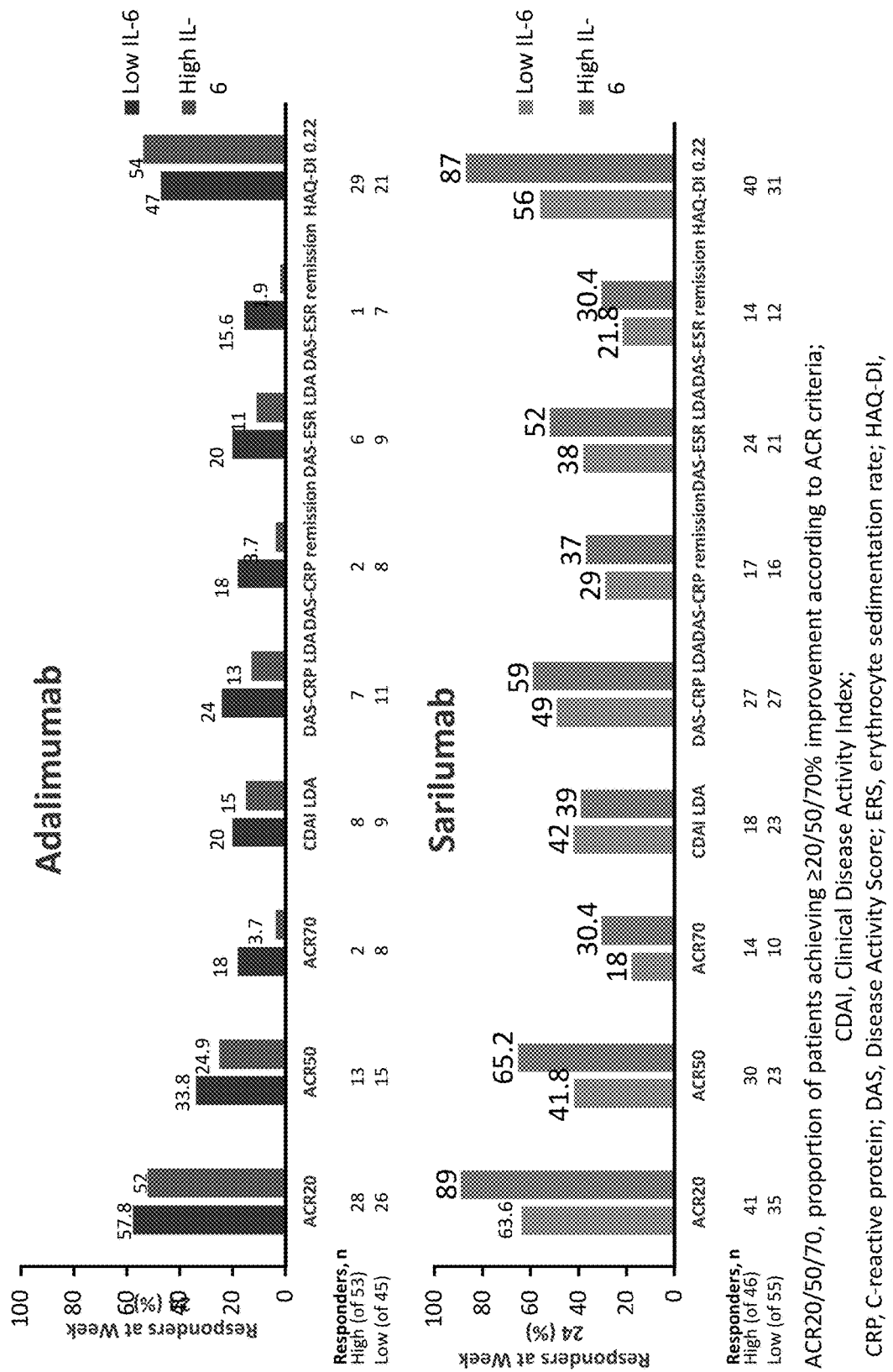
FIG. 7 are graphs depicting the 24-week efficacy according to baseline IL-6 tertile in the subjects in the MONARCH study.
Figure 8:
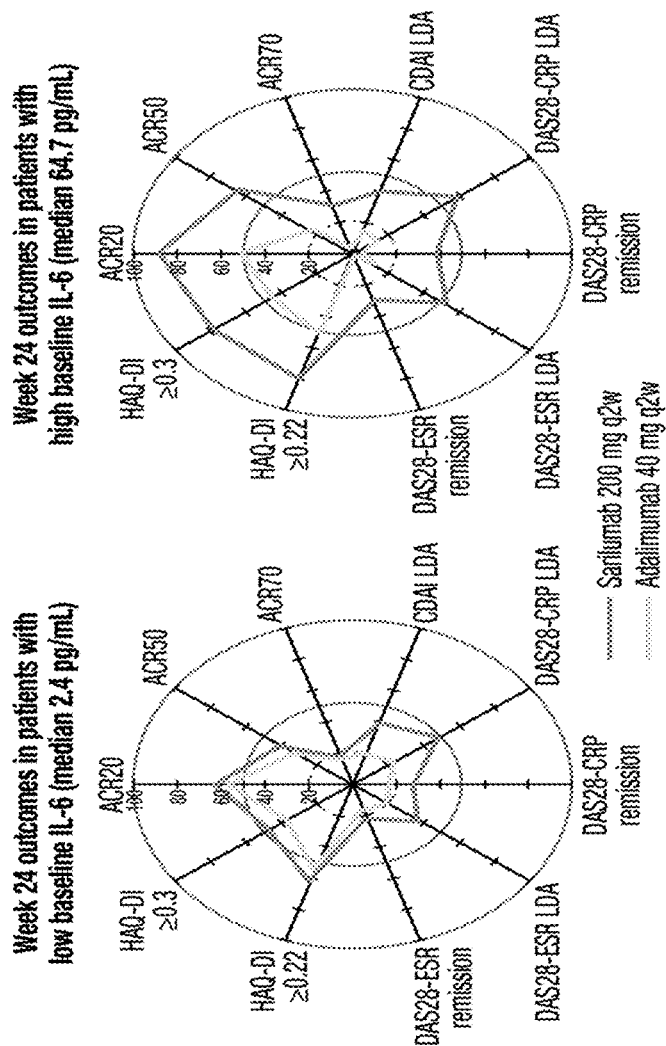
FIG. 8 schematically depicts the responses according to baseline IL-6 tertile in the subjects in the MONARCH study.

Adalimumab-treated patients with high baseline IL-6 had lower efficacy for American College of Rheumatology 50% improvement criteria (ACR50), ACR70 (70% improvement), and disease activity score (DAS) remission (FIGS. 7 and 8).

Sarilumab-treated patients with high baseline IL-6 had higher ACR20 (20% improvement)/50/70 and Health Assessment Questionnaire-Disability Index (HAQ-DI) compared with patients with lower baseline IL-6 (FIGS. 7 and 8).

Consequently, the efficacy of sarilumab compared with adalimumab was significantly greater in the high IL-6 tertile across a number of efficacy endpoints (FIG. 9).

MOBILITY and MONARCH—Efficacy Outcomes by Baseline IL-6 and CRP

In both studies, baseline IL-6 level was better at predicting outcomes than CRP (FIG. 10A) including endpoints such as Clinical Disease Activity Index (CDAI) remission (MOBILITY) and HAQ-DI (both studies) without acute-phase reactant measurements.

The differences in efficacy between sarilumab and comparator therapies in patients with high baseline IL-6 were consistent between studies across a number of endpoints (FIG. 11A).

MOBILITY and MONARCH—Safety

The safety profiles were similar between patients in the low, medium, and each study (FIG. 12).

Conclusions

Across clinical and radiographic endpoints, patients with RA who had elevated baseline IL-6 levels had a greater response to sarilumab (compared with MTX alone or adalimumab) than patients with normal IL-6 levels.

Example 4. High Baseline Serum IL-6 Identifies a Subgroup of Rheumatoid Arthritis Progression and Predicts Increased Sarilumab Treatment Response Currently, clinical tools, including biomarkers, are not available in rheumatology practice to predict response prior to initiating or switching biologic therapies.

Tools that enable physicians to identify patients who may differentially benefit from one therapy over another would be valuable.

The utility of baseline blood IL-6 levels in predicting differential treatment response to sarilumab compared to either methotrexate (in the placebo-controlled MOBILITY study), or adalimumab (in the monotherapy MONARCH study) have been evaluated Post-hoc analyses were performed using baseline blood IL-6 levels divided into low, medium and high thirds or tertiles.

In MOBILITY, all patients in the low tertile had normal IL-6 levels, while more than 85 percent of patients in the high tertile had levels three times the upper limit of normal.

Sarilumab, in combination with methotrexate, suppressed radiographic joint damage relative to placebo plus methotrexate in patients in all IL-6 tertiles.

Compared to patients with low baseline blood IL-6 levels, those in the high IL-6 tertile had higher radiographic (i.e., viewed on X-ray) progression of joint destruction at 52 weeks.

When clinical responses were evaluated, the largest increase in treatment difference between those treated with sarilumab plus methotrexate versus methotrexate alone was in patients with the highest baseline IL-6 levels. This was most notable for CDAI remission, where patients treated with sarilumab plus methotrexate were 42 times more likely to attain CDAI remission at 52 weeks than those treated with methotrexate alone.

In the MONARCH study, patients in the high baseline IL-6 tertile were more likely to achieve ACR20/50/70 responses, DAS remission, and HAQ-DI improvements with sarilumab compared to adalimumab.

In both studies, the incidence of treatment-emergent adverse events was comparable across IL-6 tertiles.

In summary, across clinical and radiographic or X-ray endpoints, patients with RA who had elevated baseline blood IL-6 levels had a greater response to sarilumab (compared with methotrexate alone or adalimumab) than patients with normal IL-6 levels.

Example 5. High Levels of Interleukin-6 (IL-6) in RA Patients are Associated with Greater Improvements in Patient-Reported Outcomes (PROs) for Sarilumab Compared with Adalimumab Increased levels of cytokines, including interleukin-6 (IL-6), reflect inflammation and are predictive of therapeutic responses in patients with RA (Burska A et al. *Mediators Inflamm.* 2014; 2014: 545493). IL-6 has been implicated in fatigue, pain, depression in RA, but a formal association with PROs has not been performed (Choy E et al. *Rheumatology* 2018; 57:18851895). Sarilumab, a fully human monoclonal antibody directed against IL-6Ra, is approved for treatment of moderate-to-severely active RA. The phase 3 MONARCH randomized controlled trial (NCT01061736) compared the efficacy and safety of sarilumab monotherapy vs adalimumab in RA patients who should not continue methotrexate treatment due to intolerance or inadequate responses. Greater reductions in disease activity and improvements in the clinical signs and function of RA were demonstrated with sarilumab vs adalimumab (Choy E et al. *Rheumatology* 2018; 57:18851895).

Therefore, a better understanding of the association between IL-6 levels and PROs is warranted to evaluate IL-6 as a biomarker for guiding RA clinical decision-making and, accordingly, a post-hoc analysis of the MONARCH study was performed in order to determine baseline if baseline IL-6 levels can differentially predict the improvement in PRO of sarilumab vs adalimumab in MONARCH.

Serum IL-6 levels were measured at baseline in 300/369 patients in the intent to treat (ITT) population. Patients were categorized in high, medium, or low IL-6 levels at baselines using tertiles. Between-group comparisons of differences at Week 24 in Short Form-36 (SF-36) physical and mental component summaries (PCS, MCS) and domain scores, Functional Assessment of Chronic Illness Therapy (FACIT)-fatigue, and morning stiffness visual analog scale (VAS) measures were performed within each tertile using a linear fixed effect model. In order to evaluate the differential effect of sarilumab vs adalimumab in the baseline high vs low IL-6 groups, an interaction test of treatment-by-baseline IL-6 group analysis was performed using low IL-6 group as the reference.

At baseline, patients in the high IL-6 tertile presented a significantly more severe condition in terms of MCS and morning stiffness (P<0.05). (Table 4). The model interaction comparing high vs low IL-6 tertiles was significant for SF-36 PCS and physical functioning domains, and for morning stiffness. In patients with high IL-6, sarilumab showed a significant (P<0.05) improvement vs adalimumab in SF-36 PCS (LS mean [LSM; least square means] of the difference: 5.57, 95% CI (2.85, 8.28)) and physical functioning (PF, 16.59 (8.15, 25.03)), role physical (9.44 (0.78, 18.10)), bodily pain (BP, 10.87 (3.92, 17.81)), vitality (8.93 (1.11, 16.74)), and social functioning (12.82 (3.07, 22.58)) domains; sarilumab also showed significant (P<0.05) effect vs adalimumab for FACIT-Fatigue (4.86 (1.06, 8.65)) and morning stiffness VAS (−19.93 (−30.30, −9.56)), with LSM changes exceeding minimum clinically important differences.

These data, evaluating IL-6 biomarker associations with SF-36 and morning stiffness VAS scores, indicate that patients with high IL-6 report better improvements for sarilumab vs adalimumab; the effect of adalimumab treatment is stable through IL-6 tertiles but the effect of sarilumab is higher, particularly in the high tertile group. The effect on PCS scores is mainly driven by the PF, consistent with previous reports of marked improvement in pain with high IL-6 levels (Gossec L et al. *Arthritis Rheumatol.* 2018; 70 (suppl 10)).

TABLE 4

| | IL-6 at baseline | | | |
| --- | --- | --- | --- | --- |
| | Low | Medium | High | Kruskal-Wallis test P-value |
| SF-36 - physical component summary score | | | | |
| Number | 98 | 100 | 100 | 0.0951 |
| Mean (SD) | 31.78 (6.16) | 30.96 (6.25) | 30.36 (6.56) | |
| SF-36 mental component summary score | | | | |
| Number | 98 | 100 | 100 | 0.0092 |
| Mean (SD) | 37.49 (10.47) | 38.80 (12.02) | 34.98 (12.61) | |
| Morning Stiffness VAS (0-100) | | | | |
| Number | 99 | 100 | 100 | 0.0002 |
| Mean (SD) | 64.60 (19.89) | 68.01 (19.70) | 75.17 (20.33) | |
| FACIT-Fatigue (0-52) | | | | |
| Number | 100 | 100 | 100 | 0.067 |
| Mean (SD) | 24.12 (9.77) | 24.86 (9.80) | 21.89 (9.62) | |

Example 6. High Serum Interleukin-6 is Associated with Severe Progression of Rheumatoid Arthritis and Increased Response to Sarilumab Compared with Methotrexate or Adalimumab A variety of conventional synthetic, biologic, and targeted synthetic disease-modifying anti-rheumatic drugs (csD-MARDs/bDMARDs/tsDMARDs) are available to reduce disease activity, inhibit joint damage progression, and prevent disability in patients with rheumatoid arthritis (RA) (Singh J A, et al. (2016) *Arthritis Rheumatol.* 68(1):1-26; Smolen J S, et al. (2017) *Ann Rheum Dis.* 76(6):960-77). However, it is estimated that up to 40% will not respond to a treatment and only 30% will achieve sustained remission (Chaves Chaparro L M, et al. (2011) *Reumatologia clinica.* 27(2):141-4; Ajeganova S, and Huizinga T. (2017) *Ther Adv Musculoskelet Dis.* 9(10):249-62; de Punder Y M, et al. (2012) Rheumatology (Oxford) 51(9):1610-7).

Treatment algorithms recommend a csDMARD such as methotrexate (MTX), followed by initiation of a bDMARD/tsDMARD for patients with inadequate control of disease activity (Singh J A, et al. (2016) *Arthritis Rheumatol.*

68(1):1-26; Smolen J S, et al. (2017) *Ann Rheum Dis.* 76(6):960-77). Selection of a bDMARD is often determined by patient access, physician experience/bias, or consideration of high-risk comorbidities (Jin Y, et al. (2017) *Arthritis Res Ther.* 19(1):159.

Treatment decisions could be optimised if diagnostics were available to help identify patients most likely to benefit from a particular therapy prior to treatment. However, currently, there are no validated predictive markers of treatment response. Although biomarkers have been evaluated in randomised controlled trials and real-world cohorts, the ability to predict outcomes before therapy initiation remains elusive (Fleischmann R, et al. (2016) *Arthritis Rheumatol.* 68(9):2083-9). For example, C-reactive protein (CRP) is routinely measured in rheumatology practice, generally correlates with disease activity, and may be elevated during flares. However, CRP testing is not currently utilised when selecting biologic therapies as there is insufficient predictive value for response to specific RA treatments (Orr C K, et al. (2018) *Frontiers in medicine.* 5:185).

Patients with RA have elevated levels of interleukin 6 (IL-6) in serum and synovial fluid (Park Y J, et al. (2016) *Sci Rep.* 6:35242; Robak T, et al. (1998) *Mediators Inflamm.* 7(5):347-53). IL-6 drives inflammation and promotes articular destruction, is involved in the development of extra-articular manifestations, and correlates with disease activity in RA (Robak T, et al. (1998) *Mediators Inflamm.* 7(5):347-53; Choy E. (2012) Rheumatology (Oxford) 51 Suppl 5:v3-11; Dayer J M, and Choy E. (2010) *Rheumatology* (Oxford) 49(1): 15-24). Despite the key role of IL-6 in RA, there is limited and inconclusive data on the potential of serum IL-6 level to predict treatment response (Wang J, et al. (2013) *BMJ Open.* 3(8):e003199).

Two monoclonal antibodies that specifically target the IL-6 signaling pathway (sarilumab and tocilizumab) are approved for the treatment of patients with RA (Genentech. Actemra® (tocilizumab) Prescribing Information updated Revised September 2018. Available from: Regeneron SG. Kevzara® (sarilumab) Prescribing Information April 2018. Since there are patients with elevated IL-6 signaling, patients with high IL-6 activity may be more likely to derive benefit from these IL-6-targeting agents versus others. The objective of this study was to investigate, by post hoc analysis, whether baseline IL-6 could differentially predict response (clinical efficacy and patient-reported outcomes (PROs)) to sarilumab vs MTX treatment in the MOBILITY (NCT01061736) trial and to sarilumab vs adalimumab treatment in the MONARCH (NCT02332590) trial (Burmester G R, et al. (2017) *Ann Rheum Dis.* 76(5):840-7; Genovese M C, et al. (2015) *Arthritis Rheumatol.* 67(6):1424-37).

Methods

Study Design

Figure 13:
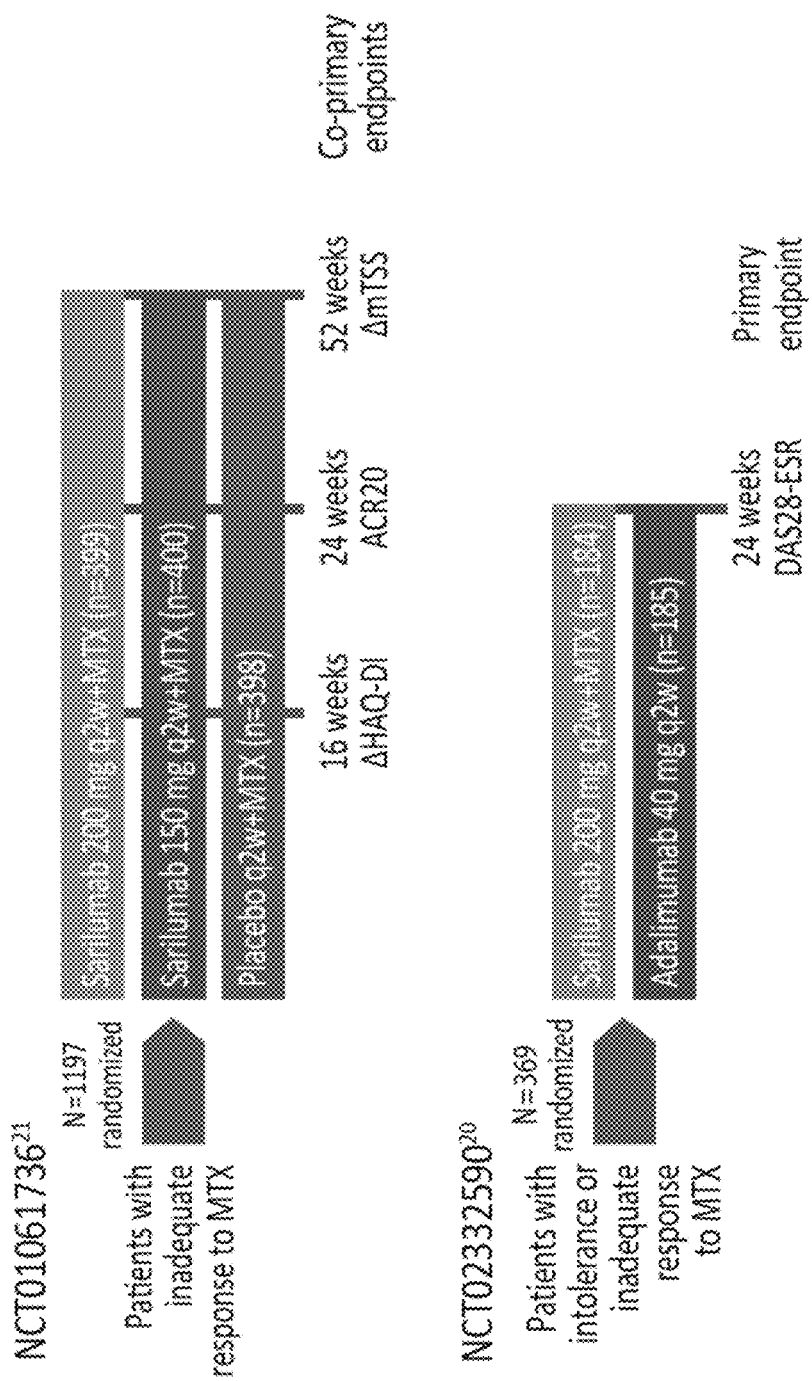
FIG. 13 depicts the design of the MOBILITY and MONARCH clinical trials. N=the numbers of patients randomized in each treatment group. ACR20, proportion of patients achieving ≥20% improvement according to American College of Rheumatology criteria; DAS28, Disease Activity Score of 28 joints; ESR, erythrocyte sedimentation rate; HAQ-DI, Health Assessment Questionnaire-Disability Index; mTSS, modified total Sharp score; MTX, methotrexate; q2w, every 2 weeks.

Details of the NCT01061736 and NCT02332590 studies have been described previously (FIG. 13) (Burmester G R, et al. (2017) *Ann Rheum Dis.* 76(5):840-7; Genovese M C, et al. (2015) *Arthritis Rheumatol.* 67(6): 1424-37).

Briefly, in NCT01061736, patients with moderate-to-severe RA and an inadequate response to MTX (MTX-IR) were randomised to receive sarilumab 150 mg (n=400), sarilumab 200 mg (n=399) or placebo (n=398) every 2 weeks (q2w) along with weekly MTX for 52 weeks. In NCT02332590, patients with moderate-to-severe RA who were intolerant of MTX or were MTX-IR were randomised to receive monotherapy with sarilumab 200 mg q2w (n=184) or adalimumab 40 mg q2w (n=185) for 24 weeks.

Both trials were conducted in accordance with the Declaration of Helsinki, approved by the appropriate ethics committees/institutional review boards, and each patient provided written informed Biomarker Assessments In NCT01061736, serum IL-6 and CRP levels were measured in the intent-to-treat (ITT) population at baseline and 24 and 52 weeks post-baseline. In NCT02332590, measurement of serum IL-6 was not a prespecified procedure, therefore, analyses were performed on samples from randomised patients who signed, and did not subsequently withdraw, informed consent for future use of samples and who had at least one evaluable serum sample drawn at baseline. This cohort is referred to as the biomarker population and consisted of 307/369 patients in the ITT population in NCT02332590 and 1194/1197 patients in the ITT population in NCT01061736 (IL-6 or CRP at baseline). Additional continuous and categorical biomarker variables, with patients grouped into tertiles according to baseline IL-6 or CRP level (high, medium, or low; Table 5). Additional biomarkers were also assessed in both studies (Boyapati A, et al. (2016) *Arthritis Res Ther.* 18(1):225; Gabay C B, et al. A. Differential effects of sarilumab and adalimumab on circulating biomarkers of bone resorption and cardiovascular risk, and predictions of clinical and patient-reported outcomes. In preparation).

Serum IL-6 levels were measured using a validated enzyme-linked immunosorbent assay (Quantikine, R&D Systems, Minneapolis, Minn., USA) at Covance Central Labs (Indianapolis, Ind., USA); the intra-assay precision was ≤9.1% coefficient of variation (CV); the inter-assay precision was ≤12% CV; the reportable range was 3.1-153, 600 pg/mL. The normal value of IL-6 identified by the laboratory was <12.5 pg/mL, (Fraunberger P, et al. (1998) *Clin Chem Lab Med* 36:797-801.) and this value was used as the definition of normal for these analyses. For both studies, approximately 90% of serum samples were collected in the morning.

CRP was measured using the high-sensitivity CRP (Siemens, Erlangen, Germany) assay at Covance (Indianapolis, Ind., USA); the intra-assay precision was <3%; the inter-assay precision was <5.4%; the reference range for healthy controls was ≤2.87 mg/L. Inclusion criteria specified a minimum CRP value required at study entry (>6 mg/L for NCT01061736; ≥8 mg/L or erythrocyte sedimentation rate (ESR) ≥28 mm/h, assessed between screening and randomisation, for NCT02332590).

Correlative analyses were performed using continuous and categorical biomarker variables, with patients grouped into tertiles according to baseline IL-6 or CRP level (high, medium or low; Table 5). Values below the lower limit of quantification (LLOQ) were replaced by a value equal to half of the LLOQ to retain these values for the analysis.

TABLE 5

Range of IL-6 and CRP levels in tertiles at baseline

| Study | IL-6, pg/mL | | | CRP, mg/L | | |
|---|---|---|---|---|---|---|
| | Low | Medium | High | Low | Medium | High |
| NCT01061736 | 1.6-9.6 | 9.8-30.7 | 31.2-648.7 | 0.2-8.9 | 9.0-22.5 | 22.6-209.0 |
| NCT02332590 | 1.6-7.1 | 7.2-39.5 | 39.6-692.3 | 0.2-4.2 | 4.3-19.4 | 19.5-202.0 |

CRP, C-reactive protein; IL-6, interleukin-6.

Efficacy and Patient Reported Outcomes (PRO) Endpoints

Efficacy was evaluated as either continuous endpoints using change from baseline, binary endpoints using a minimal clinically important difference threshold for change from baseline, or using a clinical threshold, such as low disease activity (LDA) or remission. Primary, a subset of secondary, and exploratory endpoints were evaluated.

Proportion of patients achieving ≥20/50/70% improvement according to American College of Rheumatology criteria (ACR20/50/70), Clinical Disease Activity Index (CDAI) remission (≤2.8), CDAI-LDA (≤10), Disease Activity Score in 28 joints (DAS28)-CRP or -ESR remission (≤2.6), DAS28-CRP or -ESR LDA (≤3.2), and Health Assessment Questionnaire-Disability Index (HAQ-DI) (improvement ≥0.22 or ≥0.30 and change from baseline; NCT01061736 at Week 16, NCT02332590 at Week 24). Due to low patient numbers, DAS28-ESR and CDAI-LDA were not assessed in NCT01061736 and NCT02332590, respectively. Additional PRO endpoints evaluated at Week 24 in both studies and at Week 52 in NCT01061736 included continuous change from baseline in Patient Global Assessment visual analogue scale (VAS), and pain VAS. Co-primary endpoints for NCT01061736 were ACR20, modified total Sharp score and HAQ-DI; secondary endpoints included ACR70, DAS28-CRP and CDAI. The primary endpoint for NCT02332590 was DAS28-ESR; secondary endpoints included DAS28-ESR remission, HAQ-DI and ACR20/50/70.

Statistical Methods

Baseline disease characteristics by IL-6 tertile were summarised for each study and compared using a Kruskal-Wallis test. For all endpoints, baseline was defined as the last value before the first dose of study drug. In all analyses, patients were analysed according to the treatment received.

The predictive value of serum IL-6 level for binary efficacy outcomes was tested using a logistic regression with treatment, study randomisation stratification factors (region for both studies and prior biologic use for NCT01061736), baseline IL-6 tertile and IL-6 tertile at baseline-by-treatment interaction as fixed effects; the interaction p-value was used to perform this assessment across the high and low IL-6 tertiles. Pairwise comparisons of efficacy endpoints were then performed separately between each sarilumab and comparator arm in each IL-6 tertile, and the Mantel-Haenszel estimate (stratified by randomisation factors) of odds ratio (OR) and corresponding 95% confidence interval (CI) were derived. Pairwise comparisons between IL-6 tertiles within each treatment group were similarly computed. For continuous endpoints, the analysis of covariance was performed with treatment, study randomisation stratification factors, baseline value, IL-6 tertile at baseline, and IL-6 tertile at baseline-by-treatment interaction as fixed effects. Pairwise comparisons of efficacy endpoints between sarilumab and comparator arms were performed separately for each IL-6 tertile, and the least squares (LS) means and corresponding 95% CI were derived.

The predictive value of serum IL-6 level on change from baseline in PROs was tested using an analysis of covariance using the same fixed effects as described for efficacy outcomes.

Similar regressions were performed using baseline IL-6 as a continuous measure.

As all predictive analyses were post hoc, all p-values should be considered nominal.

The incidence of treatment-emergent adverse events (AEs) in each IL-6 tertile was analysed descriptively.

All analyses were performed using SAS version 9.2 or higher.

Results

IL-6 Distribution and Baseline Disease Activity

Serum IL-6 was measured at baseline in 1193/1197 patients in the NCT01061736 ITT population and in 300/369 patients in the NCT02332590 ITT population (Table 6). In both studies, all patients in the low baseline IL-6 tertile had normal IL-6 (<12.5 pg/mL). In the high baseline IL-6 tertile, 85% of patients in NCT01061736 and all patients in NCT02332590 had IL-6 levels ≥3× the upper limit of normal (ULN). The distribution of IL-6 among tertiles was consistent in both studies (Table 5).

Given the moderate-to-high correlation reported between IL-6 and CRP (Spearman coefficient 0.71 in NCT02332590 and 0.58 in NCT01061736), CRP was significantly elevated in high versus low IL-6 tertile patients. Compared with patients in the low IL-6 tertile, those in the high IL-6 tertile had significantly greater disease activity at baseline in both studies and significantly more joint damage (Table 6). Health assessment questionnaire disability index (HAQ-DI) and patient global assessments were also significantly elevated in the high IL-6 tertile relative to low (Table 6).

TABLE 6

Baseline disease activity according to baseline IL-6 tertile

| Baseline parameter, mean (SD) | Low IL-6 | Medium IL-6 | High IL-6 |
|---|---|---|---|
| NCT01061736 | (n = 397) | (n = 398) | (n = 398) |
| Sarilumab 150 mg/200 mg/ placebo, n | 126/128/143 | 129/147/122 | 146/121/131 |
| IL-6, pg/mL, median [range]† | 5.0 [1.6-9.6] | 17.3 [9.8-30.7] | 61.0 [31.2-648.7] |
| CRP, mg/L† | 10.5 (11.6) | 18.4 (15.5) | 36.4 (30.1)* |
| mTSS | 40.8 (56.5) | 49.8 (62.1) | 56.7 (65.7)* |
| HAQ-DI | 1.6 (0.6) | 1.6 (0.6) | 1.8 (0.7)* |
| DAS28-CRP | 5.6 (0.8) | 5.9 (0.8) | 6.3 (0.8)* |
| CDAI | 38.3 (11.6) | 40.1 (12.3) | 43.0 (12.4)* |
| TJC | 25.9 (14.0) | 26.7 (14.2) | 27.8 (14.1) |
| SJC | 15.8 (9.1) | 16.5 (9.3) | 17.7 (9.5)* |
| Pain VAS | 61.6 (20.7) | 64.7 (21.4) | 69.4 (19.8)* |
| Patient global VAS | 60.5 (20.2) | 64.3 (20.1) | 69.6 (19.9)* |

TABLE 6-continued

Baseline disease activity according to baseline IL-6 tertile

| Baseline parameter, mean (SD) | Low IL-6 | Medium IL-6 | High IL-6 |
|---|---|---|---|
| NCT02332590 | (n = 100) | (n = 100) | (n = 100) |
| Sarilumab/adalimumab, n | 55/45 | 47/53 | 46/54 |
| IL-6, pg/mL, median [range]† | 2.4 [1.6-7.1] | 16.2 [7.2-39.5] | 64.7 [39.6-692.3] |
| CRP, mg/L† | 5.6 (9.2) | 15.2 (17.1) | 41.5 (34.1)* |
| HAQ-DI | 1.5 (0.6) | 1.6 (0.6) | 1.8 (0.6)* |
| DAS28-CRP | 5.5 (0.8) | 6.0 (0.7) | 6.5 (0.8)* |
| DAS28-ESR | 6.5 (0.7) | 6.8 (0.7) | 7.1 (0.9)* |
| CDAI | 40.6 (11.7) | 42.9 (11.4) | 46.0 (12.2)* |
| TJC | 26.3 (13.1) | 28.2 (14.0) | 27.8 (13.9) |
| SJC | 15.9 (10.1) | 18.6 (10.0) | 18.8 (10.7)* |
| Pain VAS | 66.2 (18.8) | 70.1 (17.4) | 77.5 (18.9)* |
| Patient global VAS | 63.4 (18.8) | 67.1 (17.0) | 73.6 (16.9)* |

*$p < 0.05$ (Kruskal-Wallis test).
†Normal IL-6 < 12.5 pg/mL; normal CRP < 2.87 mg/L.
CDAI, Clinical Disease Activity Index;
CRP, C-reactive protein;
DAS28, Disease Activity Score in 28 joints;
ESR, erythrocyte sedimentation rate;
HAQ-DI, Health Assessment Questionnaire-Disability Index;
IL-6, interleukin-6; mTSS, modified total Sharp score;
SD, standard deviation;
SJC, swollen joint count;
TJC, tender joint count.

Predictive Value of Baseline IL-6 Level for Radiographic Progression (NCT01061736)

In previous work, among the ITT population, patients who received placebo+MTX had significantly more radiographic progression than patients in the sarilumab 150 mg and 200 mg+MTX treatment groups, as assessed by mTSS at Week 52 (Genovese M C, et al. (2015) *Arthritis Rheumatol.* 67(6):1424-37).

Figures 14A, 14B, 14C:
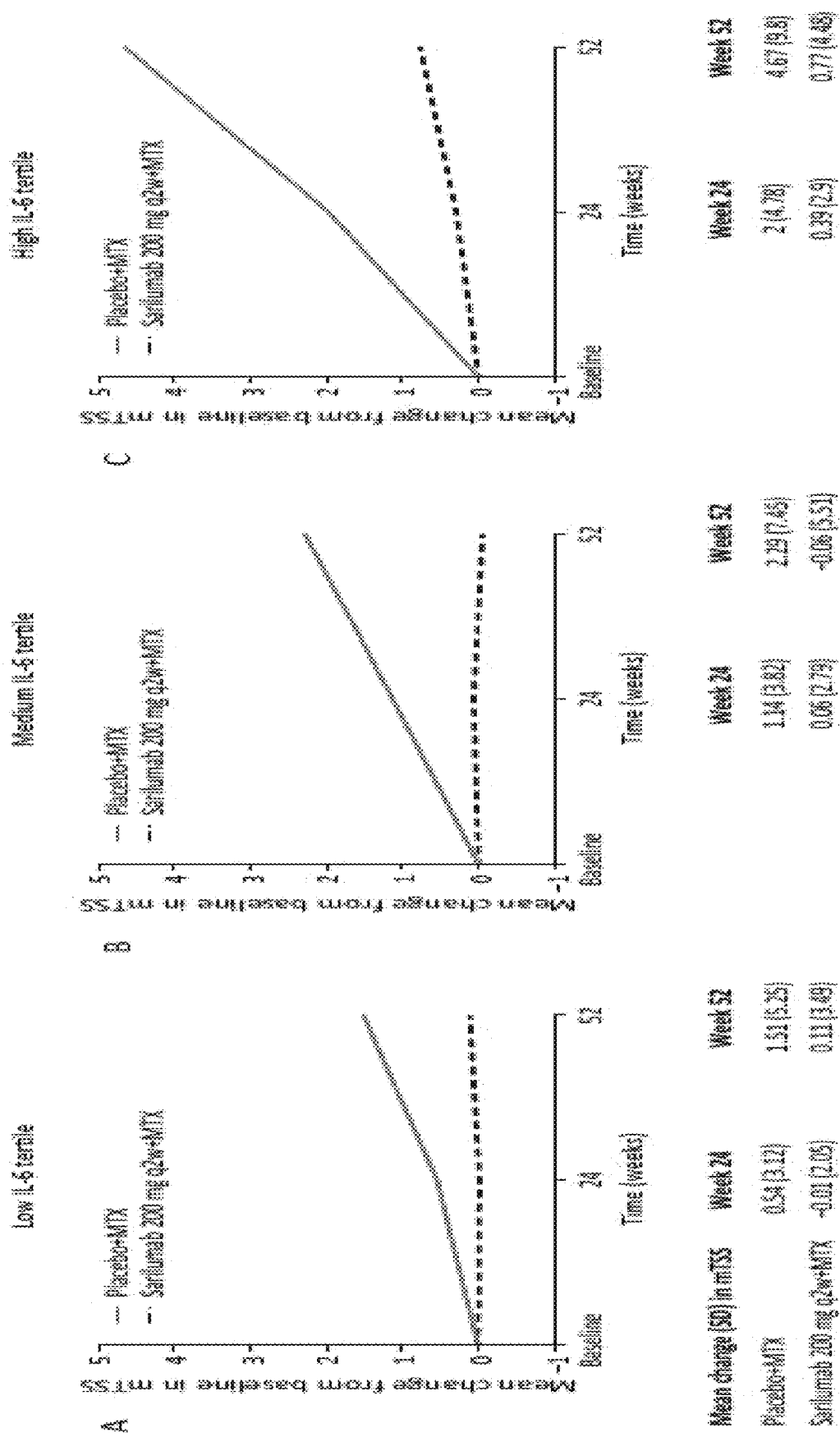
FIGS. 14A, 14B, and 14C are graphs depicting the mean change in mTSS according to baseline IL-6 tertile (14A) low, (14B) medium, and (14C) high in the MOBILITY study. All patients received weekly MTX and sarilumab was administered q2w. IL-6, interleukin-6; mTSS, modified total Sharp score; MTX, methotrexate; q2w, every 2 weeks; SD, standard deviation.

Placebo+MTX patients in the high IL-6 tertile developed substantially more joint damage at Week 24 and 52 than those in the low IL-6 tertile (mean (standard deviation (SD)) mTSS progression: 2.00 [4.78] vs 0.54 [3.12] at Week 24, 4.67 [9.80] vs 1.51 [5.25] at Week 52; OR for progression [95% CI] high vs low: 2.3 [1.4, 3.8] at Week 24, 3.3 [1.9, 5.6] at Week 52; nominal p<0.05) (FIGS. 14A-14C). Increases in erosion score and joint space narrowing (JSN) were observed. Patients treated with sarilumab 200 mg+MTX developed the least joint damage, with patients in the low and medium IL-6 tertiles experiencing minimal to no joint damage over 52 weeks. However, in the high IL-6 tertile, sarilumab 200 mg+MTX patients were approximately three times less likely than placebo+MTX patients to have joint damage progression (FIGS. 14A-14C and Table 7). The effect of sarilumab 150 mg+MTX versus placebo on joint damage progression at week 52 was not significantly different between IL-6 tertiles: low IL-6 OR [95% CI]: 0.8 [0.5, 1.4] and high IL-6 OR [95% CI]: 0.5 [0.3, 0.8].

Effect of Sarilumab on Disease Activity and PROs According to Baseline IL-6 Levels in NCT01061736

Treatment with sarilumab 200 mg+MTX resulted in numerically greater disease improvement in patients in the high versus low IL-6 tertile for HAQ-DI improvement, ≥70% improvement in American College of Rheumatology response criteria (ACR70) and Clinical Disease Activity Index (CDAI) remission. At week 52, the proportions of patients achieving ACR20, ACR50 and Disease Activity Score of 28 joints using CRP (DAS28-CRP) remission were also numerically higher in patients with high versus low IL-6 treated with sarilumab 200 mg+MTX. In contrast, there were fewer placebo+MTX responders in the high than the low IL-6 tertile, particularly for ACR70, CDAI remission and DAS28-CRP remission (FIGS. 15A and 15B).

An interaction test demonstrated that the differences in binary response to sarilumab+MTX versus placebo+MTX at week 52 were greater in the high versus low IL-6 tertiles (Table 7). The test was significant for all clinical and joint damage endpoints at week 52 (ACR20/50/70, DAS28-CRP remission, CDAI remission and HAQ-DI), but not JSN (data not shown). Higher ORs for response to sarilumab+MTX versus placebo+MTX were observed in the high versus low IL-6 tertile. Sarilumab 200 mg+MTX patients were approximately 40 times more likely than placebo+MTX patients to achieve remission considering endpoints with and without acute-phase reactants (DAS28-CRP and CDAI remission, respectively). Patients in the high IL-6 tertile treated with sarilumab 150 mg+MTX were also significantly more likely to achieve CDAI and DAS28-CRP remission compared with placebo+MTX patients (OR [95% CI] 40.3 [4.0, 405.7] and 42.6 [8.7, 208.7], respectively).

To explore the disease activity components contributing to differential IL-6 response, tender and swollen joint counts, DAS28-CRP and CDAI were evaluated by IL-6 tertile for continuous changes over the 52-week treatment period. While patients across all IL-6 tertiles had greater reductions in disease activity with sarilumab+MTX versus placebo+MTX, the greatest difference between treatment groups was observed in the high IL-6 tertile compared with the low for all measures at week 52 (Table 8A). Interaction test was significant for all endpoints. Analyses using IL-6 as a continuous measurement were also performed, and the results of the interactions tests were very similar (data not shown).

Figure 16A:
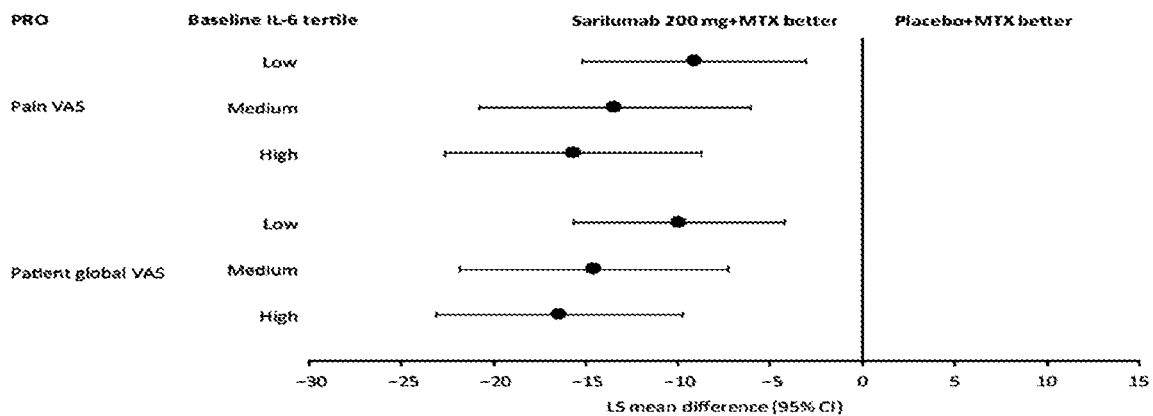
FIG. 16A is a graph depicting the change in pain VAS and patient global VAS at week 24 according to baseline IL-6 tertile sarilumab 200 mg versus placebo. The LS means are derived from a linear regression in each tertile with baseline PRO value, treatment, study randomization stratification factors (region for both studies and prior biologic use for NCT01061736) as fixed effects. *Nominal IL-6 tertile-by-treatment interaction p<0.05 (high versus low) using a linear regression with treatment, baseline PRO value, study randomization stratification factors (region for both studies and prior biologic use for NCT01061736), IL-6 tertile at baseline and IL-6 tertile at baseline-by-treatment interaction as fixed effects. CI, confidence interval; HAQ-DI, Health Assessment Questionnaire-Disability Index; IL-6, interleukin-6; LS, least squares; PRO, patient-reported outcome; VAS, visual analogue scale.
Figure 16B:
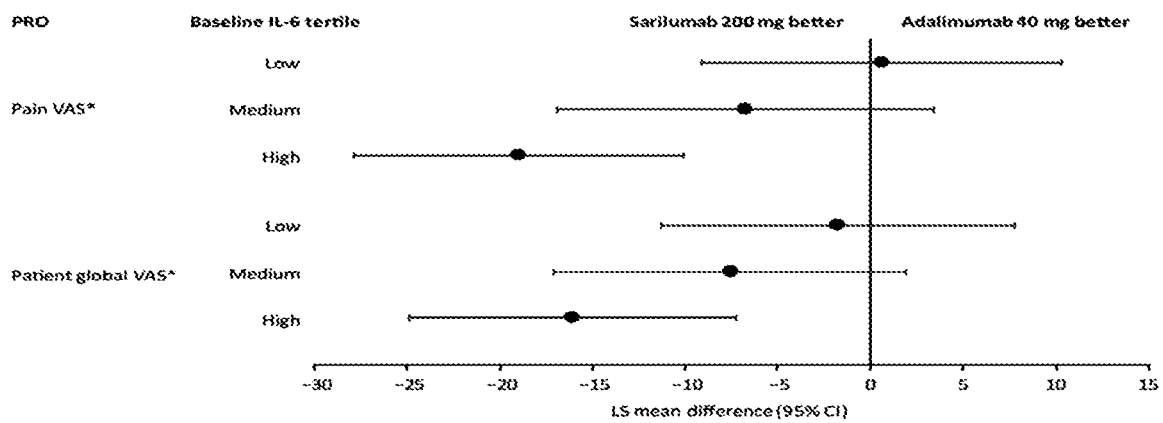
FIG. 16B is a graph depicting the change in pain VAS and patient global VAS at week 24 according to baseline IL-6 tertile sarilumab 200 mg versus adalimumab 40 mg. The LS means are derived from a linear regression in each tertile with baseline PRO value, treatment, study randomization stratification factors (region for both studies and prior biologic use for NCT01061736) as fixed effects. *Nominal IL-6 tertile-by-treatment interaction p<0.05 (high versus low) using a linear regression with treatment, baseline PRO value, study randomization stratification factors (region for both studies and prior biologic use for NCT01061736), IL-6 tertile at baseline and IL-6 tertile at baseline-by-treatment interaction as fixed effects. CI, confidence interval; HAQ-DI, Health Assessment Questionnaire-Disability Index; IL-6, interleukin-6; LS, least squares; PRO, patient-reported outcome; VAS, visual analogue scale.
Figure 16C:
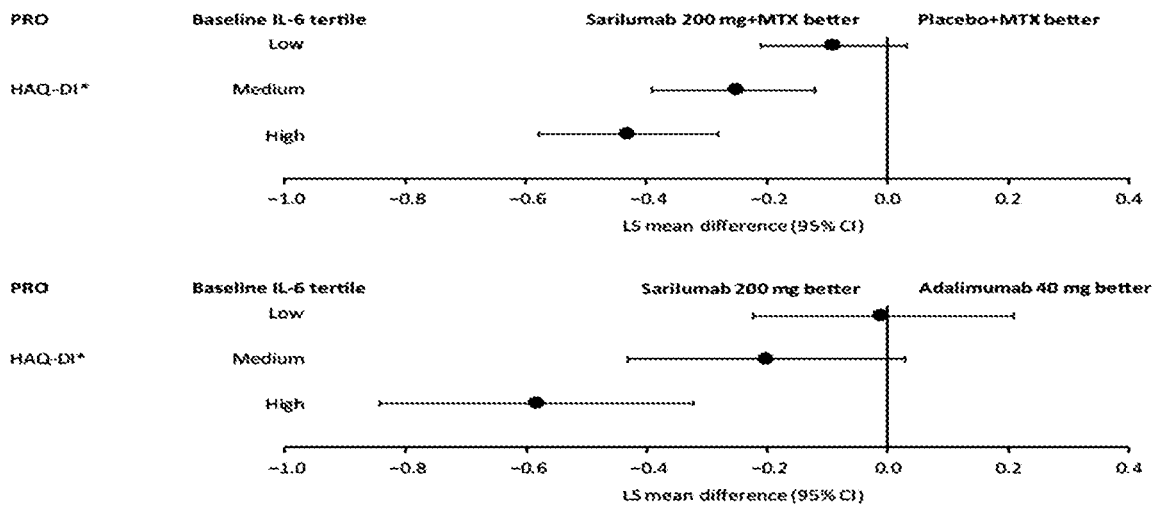
FIG. 16C is a graph depicting the change in HAQ-DI according to baseline IL-6 tertile. The LS means are derived from a linear regression in each tertile with baseline PRO value, treatment, study randomization stratification factors (region for both studies and prior biologic use for NCT01061736) as fixed effects. *Nominal IL-6 tertile-by-treatment interaction p<0.05 (high versus low) using a linear regression with treatment, baseline PRO value, study randomization stratification factors (region for both studies and prior biologic use for NCT01061736), IL-6 tertile at baseline and IL-6 tertile at baseline-by-treatment interaction as fixed effects. CI, confidence interval; HAQ-DI, Health Assessment Questionnaire-Disability Index; IL-6, interleukin-6; LS, least squares; PRO, patient-reported outcome; VAS, visual analogue scale.

Sarilumab treatment improved PROs compared with placebo+MTX in the overall ITT population (Strand V, et al. (2016) *Arthritis Res Ther* 18:198). In the analysis by IL-6 tertiles, greater improvements were observed in sarilumab+MTX-treated patients versus placebo+MTX in each tertile for HAQ-DI, and pain and patient global visual analogue scales (VAS). The magnitude of the difference between sarilumab+MTX-treated versus placebo+MTX-treated patients was larger in the high versus low tertile for HAQ-DI (with a significant treatment-by-IL-6 tertile interaction), but not for pain and patient global VAS (Table 9; FIGS. 16A-16C). Similar conclusions were drawn when IL-6 was considered as a continuous measurement (data not shown).

TABLE 7

Odds ratios for efficacy parameters according to baseline IL-6 tertile

| | Low IL-6 | Medium IL-6 | High IL-6 | All (biomarker population)* |
|---|---|---|---|---|
| NCT01061736 | | | | |
| Sarilumab 200 mg q2w/ placebo q2w (both + MTX) | (n = 128/n = 143) | (n = 147/n = 122) | (n = 121/n = 131) | (n = 396/n = 397) |
| mTSS progression (week 52), mean (SD) | | | | |
| Placebo + MTX | 1.5 (5.3) | 2.3 (7.5) | 4.7 (9.8) | 2.8 (7.7) |
| Sarilumab + MTX | 0.1 (3.5) | −0.1 (5.5) | 0.8 (4.5) | 0.3 (4.6) |
| Odds ratio (95% CI)† for sarilumab 200 mg q2w + MTX versus placebo q2w + MTX (week 52) | | | | |
| ACR20 | 2.0 (1.2 to 3.2) | 3.3 (1.9 to 5.7) | 4.9 (2.8 to 8.3)‡ | 3.0 (2.2 to 4.1) |
| ACR50 | 2.0 (1.2 to 3.4) | 3.4 (1.9 to 6.2) | 6.4 (3.5 to 11.8)‡ | 3.4 (2.4 to 4.6) |
| ACR70 | 1.9 (1.0 to 3.8) | 3.5 (1.7 to 7.4) | 7.3 (3.3 to 16.3)‡ | 3.7 (2.4 to 5.5) |
| DAS28-CRP remission | 2.5 (1.4 to 4.7) | 4.4 (2.2 to 8.9) | 39.3 (9.4 to 163.9)‡ | 5.5 (3.7 to 8.3) |
| CDAI remission | 1.8 (0.8 to 4.0) | 3.9 (1.6 to 9.5) | 42.4 (4.7 to 383.3)* | 4.4 (2.6 to 7.5) |
| HAQ-DI improvement ≥ 0.22 (week 16) | 1.1 (0.7 to 1.8) | 2.3 (1.4 to 3.9) | 2.5 (1.5 to 4.3)‡ | 1.8 (1.3 to 2.3) |
| NCT02332590 | | | | |
| Sarilumab/adalimumab | (n = 55/n = 45) | (n = 47/n = 53) | (n = 46/n = 54) | (n = 153/n = 154) |
| Odds ratio (95% CI)† for sarilumab versus adalimumab (week 24) | | | | |
| ACR20 | 1.4 (0.6 to 3.1) | 1.2 (0.5 to 3.0) | 6.6 (2.3 to 18.6)‡ | 2.0 (1.2 to 3.2) |
| ACR50 | 1.6 (0.7 to 3.7) | 1.5 (0.6 to 3.5) | 5.5 (2.3 to 13.2)‡ | 2.4 (1.5 to 3.8) |
| ACR70 | 1.1 (0.4 to 3.2) | 1.7 (0.6 to 4.6) | 10.5 (2.3 to 48.4)‡ | 2.4 (1.3 to 4.5) |
| DAS28-ESR remission | 1.5 (0.5 to 4.4) | 5.6 (1.6 to 19.4) | 33.9 (3.5 to 328.7)‡ | 4.1 (2.1 to 8.1) |
| DAS28-ESR LDA | 2.6 (1.0 to 6.7) | 5.1 (1.8 to 14.1) | 10.5 (3.5 to 31.4) | 4.2 (2.5 to 7.3) |
| DAS28-CRP remission | 2.0 (0.8 to 5.3) | 4.0 (1.5 to 10.9) | 18.4 (3.8 to 90.0)‡ | 3.5 (2.0 to 6.3) |
| DAS28-CRP LDA | 3.2 (1.3 to 7.6) | 2.2 (1.0 to 5.1) | 9.2 (3.4 to 24.8) | 3.4 (2.1 to 5.6) |
| CDAI LDA | 3.1 (1.2 to 7.7) | 1.6 (0.7 to 3.7) | 3.6 (1.4 to 9.0) | 2.3 (1.4 to 3.7) |
| HAQ-DI improvement ≥ 0.22 | 1.5 (0.7 to 3.2) | 1.2 (0.5 to 2.8) | 5.0 (1.9 to 13.2)‡ | 2.0 (1.2 to 3.2) |
| NCT02332590 | | | | |
| Sarilumab/adalimumab | (n = 55/n = 45) | (n = 47/n = 53) | (n = 46/n = 54) | (n = 153/n = 154) |
| Odds ratio (95% CI)† for sarilumab versus adalimumab (week 24) | | | | |
| ACR20 | 1.4 (0.6 to 3.1) | 1.2 (0.5 to 3.0) | 6.6 (2.3 to 18.6)‡ | 2.0 (1.2 to 3.2) |
| ACR50 | 1.6 (0.7 to 3.7) | 1.5 (0.6 to 3.5) | 5.5 (2.3 to 13.2)‡ | 2.4 (1.5 to 3.8) |
| ACR70 | 1.1 (0.4 to 3.2) | 1.7 (0.6 to 4.6) | 10.5 (2.3 to 48.4)‡ | 2.4 (1.3 to 4.5) |
| DAS28-ESR remission | 1.5 (0.5 to 4.4) | 5.6 (1.6 to 19.4) | 33.9 (3.5 to 328.7)‡ | 4.1 (2.1 to 8.1) |
| DAS28-ESR LDA | 2.6 (1.0 to 6.7) | 5.1 (1.8 to 14.1) | 10.5 (3.5 to 31.4) | 4.2 (2.5 to 7.3) |
| DAS28-CRP remission | 2.0 (0.8 to 5.3) | 4.0 (1.5 to 10.9) | 18.4 (3.8 to 90.0)‡ | 3.5 (2.0 to 6.3) |
| DAS28-CRP LDA | 3.2 (1.3 to 7.6) | 2.2 (1.0 to 5.1) | 9.2 (3.4 to 24.8) | 3.4 (2.1 to 5.6) |
| CDAI LDA | 3.1 (1.2 to 7.7) | 1.6 (0.7 to 3.7) | 3.6 (1.4 to 9.0) | 2.3 (1.4 to 3.7) |
| HAQ-DI improvement ≥ 0.22 | 1.5 (0.7 to 3.2) | 1.2 (0.5 to 2.8) | 5.0 (1.9 to 13.2)‡ | 2.0 (1.2 to 3.2) |

*Overall biomarker population, regardless of whether patient had IL-6 value at baseline.
†Mantel-Haenszel estimate stratified by study randomisation stratification factors.
‡Nominal p < 0.05 for (high or medium versus low) tertile IL-6-by-treatment interaction (logistic regression with treatment, study randomisation stratification factors [region for both studies and prior biologic use for NCT01061736], tertile IL-6 at baseline and tertile IL-6 at baseline-by-treatment interaction as fixed effects).
ACR20/50/70, ≥20/50/70% improvement according to American College of Rheumatology criteria;
CDAI, Clinical Disease Activity Index;
CI, confidence interval;
CRP, C-reactive protein;
DAS28, Disease Activity Score of 28 joints;
HAQ-DI, Health Assessment Questionnaire-Disability Index;
IL-6, interleukin-6;
LDA, low disease activity;
mTSS, modified total Sharp score;
MTX, methotrexate;
q2w, every 2 weeks.

Tables 8A and 8B. Least Squares (LS) Mean Change from Baseline for Efficacy Parameters According to Baseline IL-6 in (A) MOBILITY and (B) MONARCH

TABLE 8A

NCT01061736

| | | LS mean change from baseline (95% CI) | | | |
|---|---|---|---|---|---|
| Week 52 response | Treatment group | Low IL-6 (n = 397) | Medium IL-6 (n = 398) | High IL-6 (n = 398) | All (biomarker population) (n = 1194) |
| ΔTJC* | Sarilumab 150 mg q2w + MTX | −18.1 (−19.8 to −16.3) | −22.1 (−24.0 to −20.3)** | −22.1 (−23.5 to −20.7)** | −20.9 (−21.8 to −19.9)** |
| | Sarilumab 200 mg q2w + MTX | −19.7 (−21.4 to −17.9) | −19.8 (−21.6 to −18.0) | −22.4 (−23.9 to −20.8)** | −20.5 (−21.5 to −19.5)** |
| | Placebo + MTX | −17.9 (−19.7 to −16.1) | −17.0 (−19.3 to −14.7) | −16.1 (−18.0 to −14.2) | −17.2 (−18.4 to −16.1) |
| ΔSJC* | Sarilumab 150 mg q2w + MTX | −11.6 (−12.6 to −10.7) | −13.3 (−14.6 to −12.0)** | −14.2 (−15.1 to −13.3)** | −13.1 (−13.7 to −12.5)** |
| | Sarilumab 200 mg q2w + MTX | −12.9 (−13.9 to −12.0) | −12.9 (−14.1 to −11.6)** | −14.4 (−15.4 to −13.5)** | −13.4 (−14.0 to −12.8)** |
| | Placebo + MTX | −11.8 (−12.8 to −10.9) | −9.8 (−11.4 to −8.2) | −10.0 (−11.2 to −8.8) | −10.8 (−11.5 to −10.1) |
| ΔDAS28-CRP* | Sarilumab 150 mg q2w + MTX | −2.6 (−2.8 to −2.3)** | −3.2 (−3.5 to −2.9)** | −3.5 (−3.7 to −3.3)** | −3.1 (−3.2 to −2.9)** |
| | Sarilumab 200 mg q2w + MTX | −2.7 (−3.0 to −2.5)** | −3.2 (−3.5 to −3.0)** | −3.9 (−4.1 to −3.6)** | −3.3 (−3.4 to −3.1)** |
| | Placebo + MTX | −2.0 (−2.2 to −1.7) | −2.0 (−2.3 to −1.7) | −1.8 (−2.1 to −1.5) | −2.0 (−2.1 to −1.8) |
| ΔCDAI* | Sarilumab 150 mg q2w + MTX | −26.2 (−28.3 to −24.2) | −31.0 (−33.2 to −28.8)** | −32.7 (−34.5 to −30.9)** | −30.0 (−31.2 to −28.9)** |
| | Sarilumab 200 mg q2w + MTX | −27.8 (−29.8 to −25.7) | −29.3 (−31.4 to −27.3)** | −34.2 (−36.1 to −32.2)** | −30.3 (−31.4 to −29.1)** |
| | Placebo + MTX | −24.9 (−27.0 to −22.7) | −24.1 (−26.8 to −21.5) | −23.5 (−25.9 to −21.1) | −24.5 (−25.8 to −23.1) |

The LS means are derived from a linear regression performed on the change from baseline in efficacy measures, with baseline efficacy value, treatment, study randomisation stratification factors (prior biological use and region) as fixed effects, in each biomarker tertile.
*IL-6 tertile-by-treatment group interaction p < 0.05 for high or medium versus low tertile groups (linear regression with treatment, study randomisation stratification factors [region and prior biologic use], baseline efficacy value, IL-6 tertile at baseline, and IL-6 tertile at baseline-by-treatment interaction as fixed effects).
**p < 0.05 versus placebo.
CDAI Clinical Disease Activity Index;
CI, confidence interval;
CRP, C-reactive protein;
DAS28, Disease Activity Score of 28 joints;
LS, least squares;
SJC, swollen joint count;
TJC, tender joint count.

TABLE 8B

NCT02332590

| | | LS mean change from baseline (95% CI) | | | |
|---|---|---|---|---|---|
| Week 24 response | Treatment group | Low IL-6 (n = 100) | Medium IL-6 (n = 100) | High IL-6 (n = 100) | All (biomarker population) (n = 307) |
| ΔTJC | Sarilumab 200 mg q2w | −18.7 (−20.9 to −16.5) | −18.6 (−21.8 to −15.4) | −18.6 (−21.2 to −16.0) | −18.9 (−20.4 to −17.4) |
| | Adalimumab 40 mg q2w | −16.8 (−19.5 to −14.1) | −18.8 (−21.6 to −15.9) | −15.9 (−18.5 to −13.4) | −17.2 (−18.7 to −15.6) |
| ΔSJC | Sarilumab 200 mg q2w | −12.8 (−13.9 to −11.8) | −13.2 (−15.1 to −11.3) | −15.1 (−16.8 to −13.4)** | −13.8 (−14.7 to −12.9) |
| | Adalimumab 40 mg q2w | −12.7 (−14.0 to −11.5) | −14.0 (−15.7 to −12.3) | −11.5 (−13.2 to −9.9) | −12.9 (−13.8 to −11.9) |
| ΔDAS28-CRP* | Sarilumab 200 mg q2w | −2.5 (−2.8 to −2.2)** | −2.8 (−3.2 to −2.4)** | −3.5 (−3.8 to −3.2)** | −3.0 (−3.2 to −2.8)** |
| | Adalimumab 40 mg q2w | −1.8 (−2.2 to −1.5) | −2.2 (−2.6 to −1.8) | −2.1 (−2.4 to −1.8) | −2.1 (−2.3 to −1.9) |
| ΔCDAI | Sarilumab 200 mg q2w | −27.1 (−29.6 to −24.7) | −28.0 (−31.6 to −24.4) | −33.1 (−35.9 to −30.3)** | −29.7 (−31.3 to −28.1)** |
| | Adalimumab 40 mg q2w | −25.0 (−27.9 to −22.1) | −27.4 (−30.7 to −24.2) | −25.9 (−28.6 to −23.2) | −26.4 (−28.0 to −24.7) |

The LS means are derived from a linear regression performed on the change from baseline in efficacy measures, with baseline efficacy value, treatment, region as fixed effects, in each biomarker tertile.
*IL-6 tertile-by-treatment group interaction p < 0.05 for high or medium versus low tertile groups (linear regression with treatment, study randomisation stratification factor [region], baseline efficacy value, IL-6 tertile at baseline, and IL-6 tertile at baseline-by-treatment interaction as fixed effects).
**p < 0.05 versus adalimumab.
CDAI, Clinical Disease Activity Index;
CI, confidence interval;
CRP, C-reactive protein;
DAS28, Disease Activity Score of 28 joints;
LS, least squares;
SJC, swollen joint count;
TJC, tender joint count.

TABLE 9

Change in PROs According to Baseline IL-6 Tertile

|  | Low IL-6 | Medium IL-6 | High IL-6 | Interaction IL-6 tertile-by- treatment p-value (high versus low IL-6) |
|---|---|---|---|---|
| NCT01061736 | | | | |
| Sarilumab 150 mg q2w/ placebo q2w (both + MTX) | (n = 126/n = 143) | (n = 129/n = 122) | (n = 146/n = 131) | |
| Least squares mean change difference (95% CI) versus placebo q2w + MTX (week 24)[†] | | | | |
| ΔHAQ-DI[‡] | −0.14 (−0.26 to −0.02) | −0.20 (−0.34 to −0.06) | −0.37 (−0.51 to −0.23) | * |
| ΔPain VAS | −5.50 (−11.62 to 0.62) | −15.07 (−22.63 to −7.50) | −9.50 (−16.25 to −2.75) | |
| ΔPatient global VAS | −4.22 (−9.98 to 1.53) | −16.24 (−23.60 to −8.88) | −10.16 (−16.64 to −3.68) | |
| Sarilumab 200 mg q2w/ placebo q2w (both + MTX) | (n = 128/n = 143) | (n = 147/n = 122) | (n = 121/n = 131) | |
| Least squares mean change difference (95% CI) versus placebo q2w + MTX (week 24)[†] | | | | |
| ΔHAQ-DI[‡] | −0.09 (−0.21 to 0.03) | −0.25 (−0.39 to −0.12) | −0.43 (−0.58 to −0.28) | * |
| ΔPain VAS | −9.13 (−15.22 to −3.05) | −13.44 (−20.82 to −6.06) | −15.67 (−22.65 to −8.69) | |
| ΔPatient global VAS | −9.98 (−15.69 to −4.27) | −14.57 (−21.83 to −7.32) | −16.43 (−23.13 to −9.74) | |
| NCT02332590 | | | | |
| Sarilumab/adalimumab | (n = 55/n = 45) | (n = 47/n = 53) | (n = 46/n = 54) | |
| Least squares mean change difference (95% CI) versus adalimumab 40 mg q2w (week 24)[†] | | | | |
| ΔHAQ-DI | −0.01 (−0.22 to 0.21) | −0.20 (−0.43 to 0.03) | −0.58 (−0.84 to −0.32) | * |
| ΔPain VAS | 0.61 (−9.11 to 10.33) | −6.80 (−16.96 to 3.37) | −18.99 (−27.92 to −10.06) | * |
| ΔPatient global VAS | −1.77 (−11.36 to 7.81) | −7.56 (−17.11 to 1.98) | −16.10 (−24.89 to −7.32) | * |

*Nominal interaction p < 0.05 (high versus low) using a linear regression with treatment, study randomisation stratification factors (region for both studies and prior biologic use for NCT01061736), baseline PRO value, IL-6 tertile at baseline and IL-6 tertile at baseline-by-treatment interaction, as fixed effects.
[†]The LS means are derived from a linear regression in each tertile with baseline PRO value, treatment, study randomisation stratification factors (region for both studies and prior biologic use for NCT01061736) as fixed effects.
[‡]Week 16
CI, confidence interval;
HAQ-DI, Health Assessment Questionnaire-Disability Index;
IL-6, interleukin 6;
MTX, methotrexate;
PRO, patient-reported outcome;
q2w, every 2 weeks;
VAS, visual analogue scale.

Effect of Sarilumab on Disease Activity and PROs According to Baseline IL-6 Levels in NCT02332590

Figure 17A:
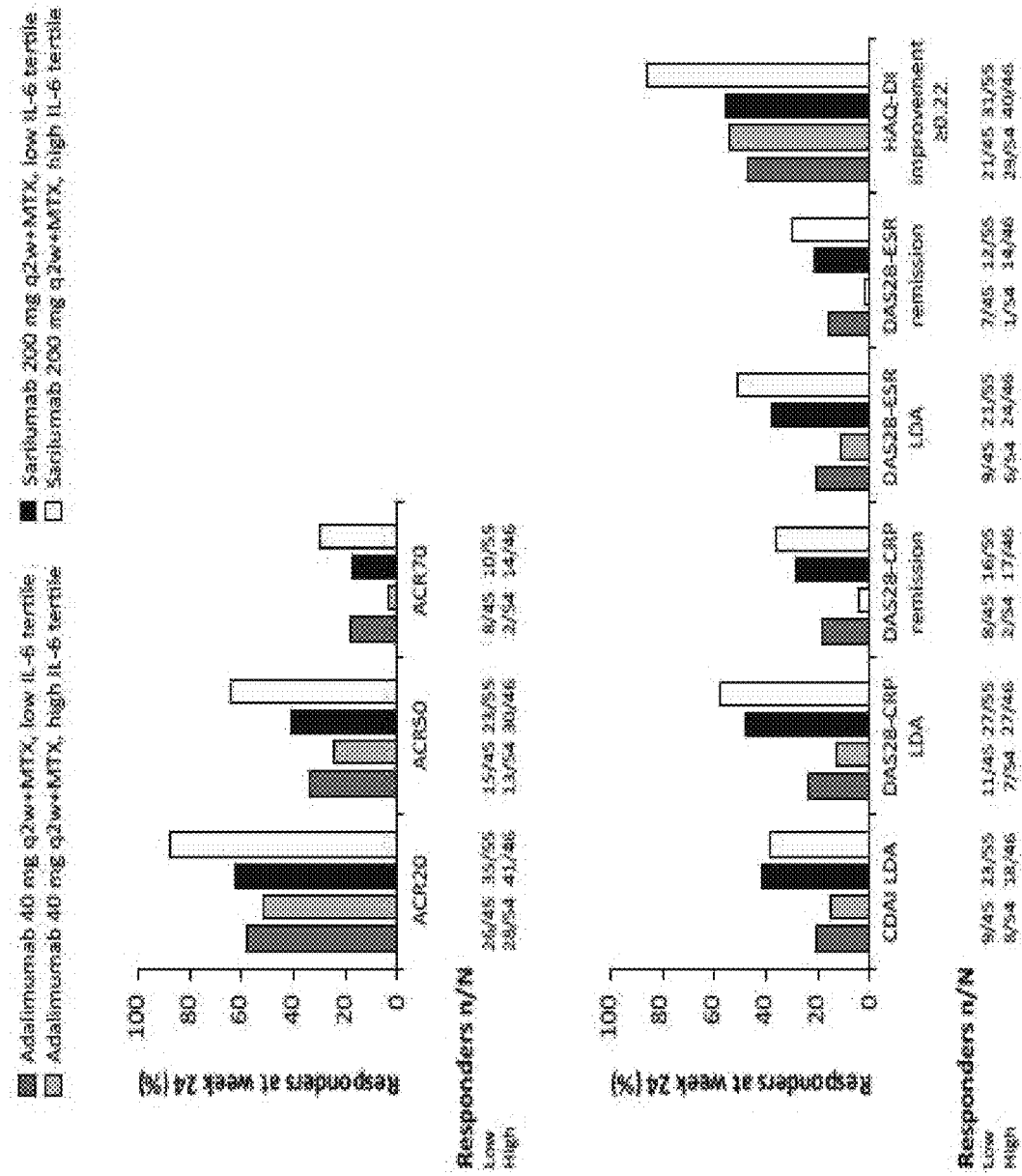
FIG. 17A provides bar graphs depicting the proportion of high vs low baseline IL-6 tertile for adalimumab and sarilumab responders at Week 24 in the MONARCH study. Due to the low number of patients in the ITT population achieving CDAI remission, this measure was not analysed by IL-6 tertile. ACR20/50/70, patients achieving ≥20/50/70% improvement according to American College of Rheumatology criteria; CDAI, Clinical Disease Activity Index; CRP, C-reactive protein; DAS28, Disease Activity Score of 28 joints; ESR, erythrocyte sedimentation rate; HAQ-DI, Health Assessment Questionnaire-Disability Index; IL-6, interleukin-6; ITT, intent-to-treat; LDA, low disease activity; MTX, methotrexate; q2w, every 2 weeks.
Figure 17B:
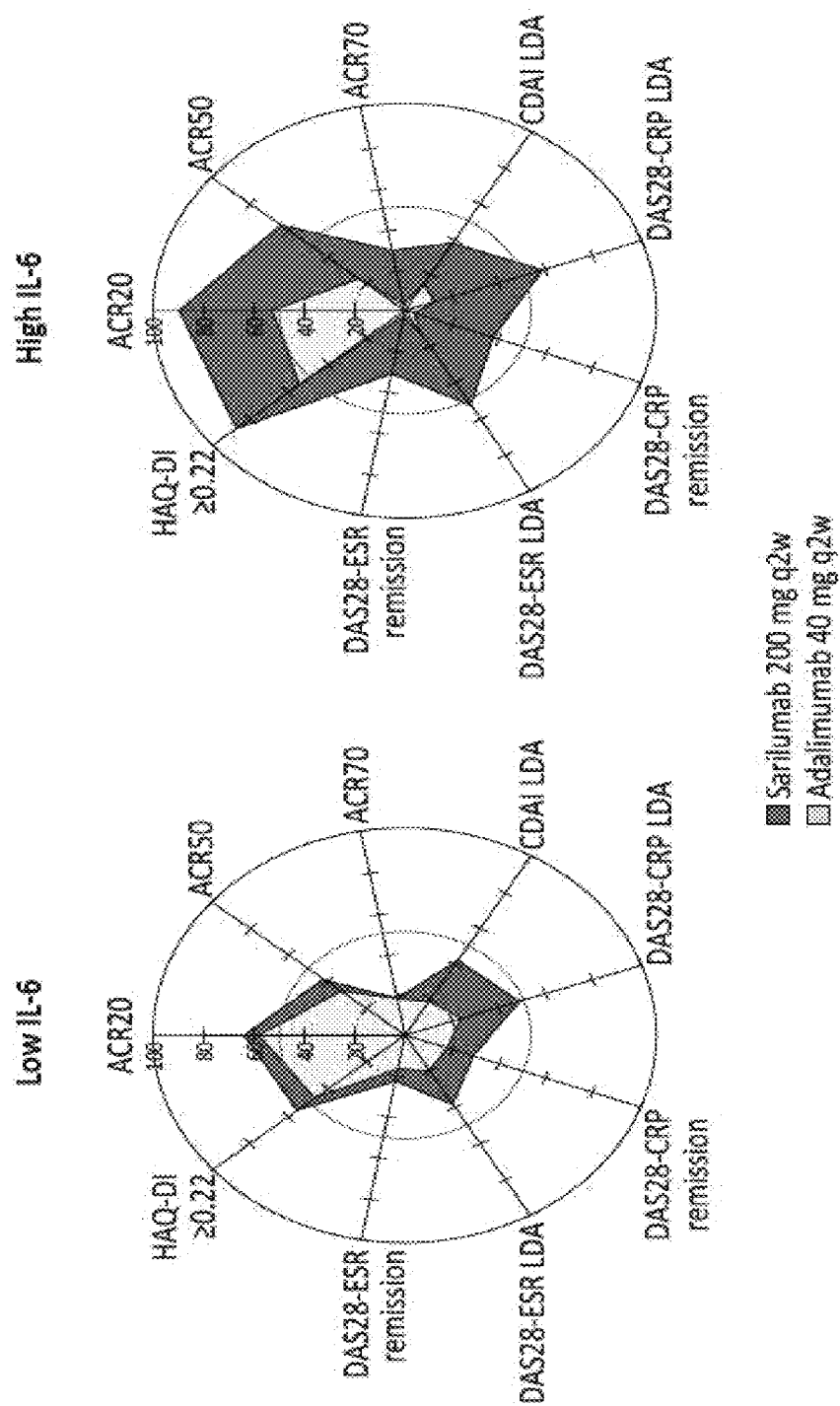
FIG. 17B depicts the proportion of adalimumab vs sarilumab for low baseline IL-6 tertile and high baseline IL-6 tertile responders at Week 24 in the MONARCH study. Due to the low number of patients in the ITT population achieving CDAI remission, this measure was not analysed by IL-6 tertile. ACR20/50/70, patients achieving ≥20/50/70% improvement according to American College of Rheumatology criteria; CDAI, Clinical Disease Activity Index; CRP, C-reactive protein; DAS28, Disease Activity Score of 28 joints; ESR, erythrocyte sedimentation rate; HAQ-DI, Health Assessment Questionnaire-Disability Index; IL-6, interleukin-6; ITT, intent-to-treat; LDA, low disease activity; MTX, methotrexate; q2w, every 2 weeks.

In the overall ITT population, sarilumab efficacy was significantly greater than adalimumab (Burmester G R, et al. (2017) *Ann Rheum Dis.* 76(5):840-7). Sarilumab-treated patients with high baseline IL-6 had numerically greater responses compared with patients with low baseline IL-6 across all endpoints except CDAI LDA (FIGS. 17A and 17B). Adalimumab-treated patients with high IL-6 levels had lower response rates at Week 24 compared to those with low IL-6 for most endpoints, except HAQ-DI.

An interaction test demonstrated the greatest difference in ACR20/50/70, DAS28 using erythrocyte sedimentation rate (DAS28-ESR) and DAS28-CRP remission, and HAQ-DI improvement in response to sarilumab versus adalimumab was in the high versus low IL-6 tertiles. These differences in the high IL-6 tertile resulted in high ORs for achieving a response across many clinical parameters (Table 7). In the high IL-6 tertile, sarilumab-treated patients were >10 times more likely to achieve ACR70 versus adalimumab-treated patients (Table 7). In addition, a larger reduction in disease activity (DAS28-ESR and DAS-CRP remission) was observed in sarilumab versus adalimumab-treated patients in the high IL-6 tertile (Table 7). Sarilumab treatment improved multiple PROs compared with adalimumab in the overall ITT population (Strand V, et al. (2018) *Arthritis Res Ther* 20:129). An interaction test for continuous changes over the 24-week treatment period demonstrated the treatment effect of sarilumab on DAS28-CRP and PROs was also greater in the high versus low IL-6 tertile (Tables 8B and 9). Similar conclusions were drawn when IL-6 was considered as a continuous measure, although the effect on disease activity and PROs appeared to be driven by high IL-6 values (data not shown).

Cross-Study Comparisons

Differences in efficacy between sarilumab and comparators (placebo+MTX or adalimumab) in patients with high baseline IL-6 were consistent between studies across multiple endpoints including ACR20, ACR70, and DAS28-CRP LDA (Table 10).

The predictivity of CRP was analysed similarly to IL-6. In both studies, baseline IL-6 was a better predictor of outcomes than baseline CRP (Table 11), with significant interaction p-values for more endpoints (Table 11), including those without acute-phase reactant measurements such as CDAI remission (NCT01061736) and HAQ-DI (both studies).

Safety

The safety profiles were similar among patients in the low, medium, and high IL-6 tertiles in each study (Table 12), and the incidence of individual AEs with sarilumab was consistent with the safety profile of IL-6 blockade. The incidences of infection and neutropenia were similar across IL-6 tertiles in each treatment group (Table 12). Patients in the high IL-6 tertile had a comparable rate of infections with sarilumab versus adalimumab (34.8% vs 31.5%).

TABLE 10

Comparison of observed response rates between studies in the high IL-6 tertile

| Endpoint at week 24 | Response rate difference versus comparator, % | |
|---|---|---|
| | NCT01061736* | NCT02332590 |
| ACR20 | 38.3 | 37.2 |
| ACR50 | 31.8 | 41.1 |
| ACR70 | 25.2 | 26.7 |
| CDAI LDA | 31.6 | 24.3 |
| DAS28-CRP LDA | 44.5 | 45.7 |
| DAS28-CRP remission | 28.6 | 33.3 |
| HAQ-DI improvement ≥ 0.22 | 21.7 | 33.3 |

*Sarilumab 200 mg q2w + MTX versus placebo + MTX
ACR20/50/70, patients achieving ≥ 20/50/70% improvement according to American College of Rheumatology criteria;
CDAI, Clinical Disease Activity Index;
CRP, C-reactive protein; DAS28, Disease Activity Score of 28 joints;
ESR, erythrocyte sedimentation rate;
HAQ-DI, Health Assessment Questionnaire-Disability Index;
IL-6, interleukin-6;
LDA, low disease activity.

TABLE 11

Comparison of odds ratios according to biomarker: high IL-6 level versus high CRP level

| NCT01061736: Endpoints at week 52 | All (biomarker population) | High IL-6 (median, 61 pg/mL) | High CRP (median, 36.9 mg/L) |
|---|---|---|---|
| mTSS progression, mean (SD) | | | |
| Placebo + MTX | 2.8 (7.7) | 4.7 (9.8) | 3.8 (9.3) |
| Sarilumab 200 mg + MTX | 0.3 (4.6) | 0.8 (4.5) | 1.3 (4.7) |

| | Odds ratio (95% CI)† | | |
|---|---|---|---|
| | Sarilumab 200 mg + MTX versus placebo + MTX | | |
| NCT01061736: Endpoints at week 52 | All (biomarker population) | High IL-6 (median, 61 pg/mL) | High CRP (median, 37 mg/L) |
| ACR20 | 3.1 (2.3 to 4.1) | 4.9 (2.8 to 8.3)* | 3.8 (2.3 to 6.5) |
| ACR50 | 3.4 (2.4 to 4.7) | 6.4 (3.5 to 11.8)* | 4.6 (2.5 to 8.3) |
| ACR70 | 3.7 (2.4 to 5.5) | 7.3 (3.3 to 16.3)* | 5.5 (2.6 to 11.5)* |
| DAS28-CRP remission | 5.5 (3.7 to 8.3) | 39.3 (9.4 to 163.9)* | 16.3 (6.0 to 44.2)* |
| CDAI remission | 4.4 (2.6 to 7.5) | 42.4 (4.7 to 383.3)* | 19.3 (4.3 to 86.2)* |

| | Odds ratio (95% CI)† sarilumab versus adalimumab | | |
|---|---|---|---|
| NCT02332590: Endpoints at week 24 | All (biomarker population) | High IL-6 (median, 65 pg/mL) | High CRP (median, 38 mg/L) |
| ACR20 | 2.0 (1.2 to 3.2) | 6.6 (2.3 to 18.6)* | 3.7 (1.5 to 8.9)* |
| ACR50 | 2.4 (1.5 to 3.8) | 5.5 (2.3 to 13.2)* | 3.5 (1.5 to 7.9) |
| ACR70 | 2.4 (1.3 to 4.5) | 10.5 (2.3 to 48.4)* | 4.4 (1.3 to 14.1) |

TABLE 11-continued

Comparison of odds ratios according to biomarker: high IL-6 level versus high CRP level

| NCT01061736: Endpoints at week 52 | All (biomarker population) | High IL-6 (median, 61 pg/mL) | High CRP (median, 36.9 mg/L) |
|---|---|---|---|
| DAS28-CRP remission | 3.5 (2.0 to 6.3) | 18.4 (3.8 to 90.0)* | 7.6 (2.0 to 28.5) |
| CDAI LDA | 2.3 (1.4 to 3.7) | 3.6 (1.4 to 9.0) | 2.8 (1.1 to 7.0) |
| HAQ-DI improvement ≥ 0.22 | 2.0 (1.2 to 3.2) | 5.0 (1.9 to 13.2)* | 2.8 (1.2 to 6.5) |

*Nominal p < 0.05 for (high versus low) tertile IL-6/CRP-by-treatment interaction (logistic regression with treatment, study randomisation stratification factors - region for NCT01061736 and NCT02332590, prior biologic use for NCT01061736 - baseline IL-6/CRP tertile, and IL-6/CRP tertile at baseline-by-treatment interaction as fixed effects).
†Mantel-Haenszel odds ratio stratified by study randomisation stratification factors.
ACR20/50/70, patients achieving ≥ 20/50/70% improvement according to American College of Rheumatology criteria;
CDAI, Clinical Disease Activity Index;
CI, confidence interval;
CRP, C-reactive protein;
DAS28, Disease Activity Score in 28 joints;
ESR, erythrocyte sedimentation rate;
HAQ-DI, Health Assessment Questionnaire-Disability Index;
IL-6, interleukin-6;
LDA, low disease activity;
MTX, methotrexate.

TABLE 12

Summary of treatment-emergent AEs according to baseline IL-6 tertile

NCT01061736 (all arms + MTX)

| | Low IL-6 | | | Medium IL-6 | | | High IL-6 | | |
|---|---|---|---|---|---|---|---|---|---|
| AE, n (%) | Placebo (n = 143) | Sarilumab 150 mg (n = 126) | Sarilumab 200 mg (n = 128) | Placebo (n = 122) | Sarilumab 150 mg (n = 129) | Sarilumab 200 mg (n = 147) | Placebo (n = 131) | Sarilumab 150 mg (n = 146) | Sarilumab 200 mg (n = 121) |
| Any TEAE | 87 (60.8) | 92 (73.0) | 101 (78.9) | 74 (60.7) | 98 (76.0) | 117 (79.6) | 84 (64.1) | 110 (75.3) | 94 (77.7) |
| Infections and infestations* | 44 (30.8) | 58 (46.0) | 46 (35.9) | 44 (36.1) | 48 (37.2) | 62 (42.2) | 39 (29.8) | 62 (42.5) | 51 (42.1) |
| Neutropenia† | 1 (0.7) | 10 (7.9) | 16 (12.5) | 0 | 10 (7.8) | 20 (13.6) | 0 | 17 (11.6) | 20 (16.5) |
| Any serious TEAE | 10 (7.0) | 9 (7.1) | 14 (10.9) | 5 (4.1) | 19 (14.7) | 19 (12.9) | 6 (4.6) | 9 (6.2) | 12 (9.9) |
| Any TEAE leading to death | 0 | 1 (0.8) | 1 (0.8) | 0 | 1 (0.8) | 0 | 2 (1.5) | 0 | 0 |
| Any TEAE leading to permanent treatment discontinuation | 5 (3.5) | 13 (10.3) | 17 (13.3) | 6 (4.9) | 22 (17.1) | 21 (14.3) | 9 (6.9) | 16 (11.0) | 16 (13.2) |

NCT02332590

| | Low IL-6 | | Medium IL-6 | | High IL-6 | |
|---|---|---|---|---|---|---|
| AE, n (%) | Adalimumab 40 mg (n = 45) | Sarilumab 200 mg (n = 55) | Adalimumab 40 mg (n = 53) | Sarilumab 200 mg (n = 47) | Adalimumab 40 mg (n = 54) | Sarilumab 200 mg (n = 46) |
| Any TEAE | 31 (68.9) | 33 (60.0) | 30 (56.6) | 30 (63.8) | 35 (64.8) | 33 (71.7) |
| Infections and infestations* | 15 (33.3) | 12 (21.8) | 10 (18.9) | 13 (27.7) | 17 (31.5) | 16 (34.8) |
| Neutropenia† | 1 (2.2) | 9 (16.4) | 0 | 3 (6.4) | 0 | 10 (21.7) |
| Any serious TEAE | 3 (6.7) | 2 (3.6) | 1 (1.9) | 3 (6.4) | 5 (9.3) | 1 (2.2) |
| Any TEAE leading to death | 0 | 0 | 0 | 1 (2.1) | 0 | 0 |
| Any TEAE leading to permanent treatment discontinuation | 6 (13.3) | 2 (3.6) | 2 (3.8) | 4 (8.5) | 4 (7.4) | 2 (4.3) |

In both trials, sarilumab doses were administered every 2 weeks. In NCT02332590, adalimumab was administered every 2 weeks. In NCT01061736, all patients were receiving background methotrexate.
*MedDRA system organ class.
†MedDRA preferred term.
AE, adverse event; IL-6, interleukin-6; MedDRA, Medical Dictionary for Regulatory Activities (version 16.0 for NCT01061736 and 18.1 for NCT02332590); MTX, methotrexate; SAE, serious adverse event; TEAE, treatment-emergent adverse event.

Summary

This post hoc analysis of 1493 MTX-intolerant/IR patients with RA demonstrated that patients with the highest baseline IL-6 levels had moderately increased disease activity at baseline, but significantly more baseline joint damage, compared with patients within the normal IL-6 range.

Patients with high IL-6 levels had a greater response to sarilumab compared with placebo+MTX or adalimumab. The differences in efficacy between sarilumab and comparators (placebo+MTX or adalimumab) in patients with RA who had high baseline IL-6 were consistent between studies across multiple endpoints. It should be noted that the large ORs were driven by low levels of response in patients with high IL-6 levels who received comparators. Patients with high IL-6 levels were more likely to achieve ACR responses, DAS28-CRP or CDAI remission, and HAQ-DI improvements with sarilumab than with placebo and were more likely to achieve DAS28-ESR or DAS28-CRP remission and ACR responses compared with adalimumab.

Studies of circulating IL-6 concentrations in patients with RA treated with tocilizumab have reported conflicting findings: some found that responses to treatment improved in patients with low IL-6 (Nishina N K Y, et al. (2017) *Arthritis Rheumatology.* 69 (S10); Shimamoto K, et al. (2013) *J Rheumatol.* 40(7):1074-81), while others identified high IL-6 patients as better responders. (Wang J, et al. (2013) *BMJ Open.* 3(8):e003199; Diaz-Torne C, et al. (2018) *Semin Arthritis Rheum.* 47(6):757-64; Uno K, et al. (2015) *PLoS One.* 10(7):e0132055). A comprehensive study conducted by Wang et al. (*BMJ Open.* (2013) 3(8):e003199) evaluated the impact on change in DAS28-ESR with tocilizumab for every threefold increase in baseline IL-6. This analysis did not directly compare patients with the highest IL-6 levels to the patients with lowest. It is unclear why baseline IL-6 did not predict a significant change in DAS28-ESR; one possibility is that the analysis combined two doses of tocilizumab (4 and 8 mg/kg) with different efficacy profiles. For the analysis presented herein, tertiles were used to compare efficacy in patients with normal levels of IL-6 (low tertile) and patients with baseline IL-6 levels ≥3×ULN (high tertile). There are currently no established IL-6 thresholds available from either clinical trial or real-world practice.

The data presented herein demonstrated that high rather than low baseline IL-6 levels had predictive value for differentiating response to sarilumab versus comparators. In both studies, baseline IL-6 was better at predicting outcomes than baseline CRP, including radiographic disease progression and endpoints without acute-phase reactant measurements such as CDAI remission and HAQ-DI. This is of note because, although increased CRP levels were an inclusion criterion in both studies, CRP alone did not differentiate between fast and slow rates of disease progression.

Example 7. High Baseline Serum IL-6 Predicts Increased Sarilumab Treatment Response for Patient Reported Outcomes Among Rheumatoid Arthritis Patients with Inadequate Response to Methotrexate Background IL-6 is a key cytokine in the pathogenesis of rheumatoid arthritis (RA) and is elevated in in serum and synovial fluid of RA patients. However, the impact of baseline IL-6 levels on patient reported outcomes (PROs) has not been explored in clinical trials evaluating IL-6 blockade. Sarilumab, a human monoclonal antibody targeting IL-6 receptor alpha, plus MTX significantly improved clinical and patient reported outcomes vs MTX alone among inadequate responders (IR) to MTX in the MOBILITY randomized controlled trial (NCT01061736). This post-hoc analysis evaluated whether baseline IL-6 levels can predict greater improvements in PROs with sarilumab+MTX vs MTX.

Methods 1193 patients of 1197 in the intent to treat population with moderate-to-severely active RA receiving MTX+placebo or sarilumab (150 mg or 200 mg subcutaneous every 2 weeks)+MTX, with baseline IL-6 values were included. Serum IL-6 was measured by immunoassay (Quantikine IL-6). Patients were grouped into tertiles according to baseline IL-6 levels (high, medium and low, see Table 13). PROs were measured at baseline and post-treatment (Weeks [W] 24 and 52): pain visual analog scale (VAS), SF-36 physical (PCS) and mental component scores (MCS), FACIT-Fatigue (FACIT-F) and sleep VAS. Linear regression on changes from baseline in PROs were performed with IL-6 tertile, treatment, prior biologic use, and region as stratification factors, and baseline IL-6 tertile-by-treatment interactions (with placebo and low IL-6 tertile as references) as fixed effects, to assess the predictivity of IL-6 levels. P-values of the interaction for each sarilumab group were provided using placebo and low tertile as references. Pairwise comparisons of PRO improvements between treatment groups were also performed in each tertile; differences in least square means vs placebo, and 95% confidence intervals were calculated.

Results

At baseline, patients in the high IL-6 tertile had greater disease activity, more radiographic structural damage, elevated levels of CRP levels, and poorer PROs (pain VAS, SF36-PCS, and sleep VAS; data not shown) vs those in lower IL-6 levels (P<0.05) and generally reported greater PRO improvements with sarilumab treatment vs placebo (Table). Significant differences (interaction P-value <0.005) between high and low tertiles were evident in pain VAS (W52) and SF-36 PCS (W24 and W52) with 200 mg; SF-36 MCS with both 150 mg and 200 mg (W52) and FACIT-F scores with both 150 mg and 200 mg (W24 and W52). The incidence of treatment emergent adverse events was similar across IL-6 groups.

Conclusions

Among MTX-IR RA patients, high baseline IL-6 levels predict better improvements in PROs with sarilumab treatment vs placebo than those with low levels. This findings support previous analyses, which showed that across clinical and radiographic endpoints, patients with elevated baseline IL-6 levels reported greater responses to sarilumab compared with MTX or adalimumab than those without IL-6 elevations.

TABLE 13

Impact of IL-6 at baseline on differences in mean PRO improvement for sarilumab versus placebo in MTX-IR patients with RA

| Estimated difference (95% CI) in least squares mean change from baseline vs placebo | Sarilumab 150 mg | | | Sarilumab 200 mg | | |
|---|---|---|---|---|---|---|
| | Low 5.0 (1.6-9.6) pg/mL (n = 126) | Medium 17.3 (9.8-30.7) pg/mL (n = 129) | High 61.0 (31.2-648.7) pg/mL (n = 146) | Low 5.0 (1.6-9.6) pg/mL (n = 128) | Medium 17.3 (9.8-30.7) pg/mL (n = 147) | High 61.0 (31.2-648.7) pg/mL (n = 121) |
| Pain VAS: | | | | | | |
| Week 24 | −5.5 (−11.6, 0.6) | −15.1 (−22.6, −7.5)* | −9.5 (−16.3, −2.8) | −9.1 (−15.2, −3.1) | −13.4 (−20.8, −6.1) | −15.7 (−22.7, −8.7) |
| Week 52 | −3.9 (−10.7, 2.8) | −12.5 (−20.5, −4.5) | −12.3 (−19.9, −4.7) | −4.4 (−11.1, 2.3) | −11.7 (−19.7, −3.8) | −15.7 (−23.6, −7.9)* |
| SF-36 PCS: | | | | | | |
| Week 24 | 1.8 (−0.1, 3.6) | 2.5 (0.2, 4.8) | 4.7 (2.4, 6.9) | 1.9 (0.1, 3.7) | 3.1 (0.8, 5.4) | 5.1 (2.7, 7.4)* |
| Week 52 | 2.3 (0.0, 4.6) | 1.8 (−0.8, 4.4) | 5.4 (2.9, 8.0) | 1.3 (−1.0, 3.5) | 2.3 (−0.3, 4.9) | 6.7 (4.2, 9.3)** |
| SF-36 MCS: | | | | | | |
| Week 24 | 2.1 (−0.6, 4.7) | 1.7 (−1.1, 4.5) | 1.2 (−1.4, 3.8) | 3.9 (1.4, 6.5) | 3.5 (0.8, 6.3) | 5.1 (2.4, 7.7) |
| Week 52 | −1.0 (−4.1, 2.0) | 0.5 (−2.4, 3.4) | 5.3 (2.1 8.5)** | 1.5 (−1.5, 4.4) | 1.2 (−1.7, 4.2) | 7.1 (3.9, 10.4)* |
| FACIT-Fatigue: | | | | | | |
| Week 24 | 0.6 (−1.4, 2.7) | 3.1 (0.7, 5.5) | 4.3 (2.0, 6.6)* | 1.7 (−0.4, 3.7) | 3.3 (0.9, 5.6) | 5.2 (2.8, 7.5)* |
| Week 52 | 0.2 (−2.4, 2.8) | 2.0 (−0.6, 4.6) | 5.2 (2.7, 7.8)** | −0.3 (−2.9, 2.3) | 2.2 (−0.4, 4.8) | 7.3 (4.8, 9.9)** |
| Sleep VAS: | | | | | | |
| Week 24 | −4.2 (−10.6, 2.2) | −6.1 (−13.7, 1.5) | −8.6 (−15.8, −1.4) | −3.3 (−9.6, 3.1) | −3.3 (−10.7, 4.1) | −12.0 (−19.4, −4.5) |
| Week 52 | 0.5 (−7.0, 7.9) | −5.9 (−14.0, 2.2) | −9.3 (−16.9, −1.6) | −2.1 (−9.5, 5.3) | −3.4 (−11.5, 4.7) | −9.7 (−17.7, −1.8) |

Note:
*and **denote significant difference (interaction P value < 0.05 and P < 0.01, using placebo & low IL6 as references) beween high or medium IL6 group and low IL6 group in PRO improvement difference between treatment arm and placebo arm. LS-means differences and 95% confidence intervals are calculated within each IL-6 group. Low, medium or high IL-6 levels are reported as median and range across groups.

Example 8. Effect of Sarilumab on Glycosylated Hemoglobin in Patients with Rheumatoid Arthritis and Diabetes Sarilumab, a human mAb blocking the IL-6Rα, is approved for adult patients with moderately to severely active RA. Type 2 diabetes is a common comorbidity in patients with RA, and elevated IL-6 may be a risk factor. This post hoc analysis investigated effects of sarilumab on glycosylated hemoglobin (HbA1c) and fasting glucose.

TARGET (NCT01709578) was a 24-week trial of sarilumab 150/200 mg q2w vs placebo (all +csDMARD) in TNFi-inadequate response/intolerant (IR/INT) patients; 78/546 (14.3%) patients had diabetes (baseline fasting glucose ≥7 mmol/L or baseline HbA1c ≥6.5%). MONARCH (NCT02332590) was a 24-week monotherapy trial of sarilumab 200 mg q2w vs adalimumab 40 mg q2w in MTX-IR/INT, bDMARD-naïve patients; 28/369 (7.6%) patients had diabetes.

At Week 24, among patients with RA and diabetes, least-squares mean (LSM) change from baseline in HbA1c was −0.33%/−0.6% with sarilumab 150/200 mg q2w vs+0.18% with placebo in the combination study and −0.43% vs −0.02 with sarilumab 200 mg q2w vs adalimumab 40 mg q2w monotherapy. There was no interaction between change in HbA1c and corticosteroid use, nor were changes in HbA1c correlated with changes in CRP, DAS28-CRP, or hemoglobin. Sarilumab-treated patients with baseline IL-6 >37.5 pg/mL (≥3×ULN) had greater reductions in HbA1c than those with baseline IL-6 ≤37.5 pg/mL (LSM change, −0.27 vs −0.11). Sarilumab safety profile was similar in diabetic vs non-diabetic RA patients.

Patients with RA and diabetes treated with sarilumab had greater improvements in HbA1c than with adalimumab or placebo. With monotherapy, differences between sarilumab and adalimumab were more pronounced among patients with higher baseline IL-6 levels.

Example 9. High Levels of Interleukin-6 (IL-6) in Patients with Rheumatoid Arthritis are Associated with Greater Improvements in Patient Reported Outcomes for Sarilumab Compared with Adalimumab Introduction Increased levels of cytokines, including interleukin-6 (IL-6), reflect inflammation (Burska A et al. *Mediators Inflamm*. 2014; 2014:545493) and are associated with disease activity and potentially therapeutic responses in patients with rheumatoid arthritis (RA) (Fabre S et al. *Clin Exp Immunol*. 2009; 155:395-402).

IL-6 has been implicated in fatigue, pain and depression in RA (Fabre S et al. *Clin Exp Immunol*. 2009; 155:395-402)

but a formal association with health-related quality of life (HRQoL) has not been investigated.

Sarilumab, a fully human monoclonal antibody directed against the IL-6 receptor antagonist, is approved for the treatment of moderately to severely active RA.

The Phase 3 MONARCH randomized controlled trial (NCT01061736) compared the efficacy and safety of subcutaneous (SC) sarilumab 200 mg monotherapy every 2 weeks (Q2W) versus adalimumab 40 mg SC monotherapy Q2W in patients with RA who should not continue methotrexate treatment due to intolerance or inadequate responses. Greater reductions in disease activity and improvements in the clinical signs of RA and physical function were demonstrated with sarilumab versus adalimumab (Burmester G R et al. *Ann Rheum Dis.* 2017; 76:840-847). In addition, sarilumab monotherapy versus adalimumab monotherapy resulted in greater improvements across multiple HRQoL endpoints (Strand V et al. *Arthritis Res Ther.* 2018; 20:129).

A better understanding of the association between IL-6 levels and HRQoL endpoints is warranted to evaluate IL-6 as a biomarker for guiding RA clinical decision-making given that there are multiple approved RA therapeutics that block IL-6 signaling.

Objective

To evaluate, by post-hoc analysis, the potential of baseline IL-6 levels to differentially predict the improvement in HRQoL endpoints with sarilumab versus adalimumab in MONARCH.

Methods

Serum IL-6 levels were measured using a validated ELISA at baseline in 300/369 patients in the intent-to-treat (ITT) population who consented to biomarker analyses.

Patients were categorized into tertiles (high, medium and low) based on IL-6 levels Baseline and change from baseline (CFB) at Week 24 were obtained for each IL-6 tertile for the following HRQoL endpoints:

Short Form-36 (SF-36) physical and mental component summary scores (PCS, MCS);

SF-36 domains: physical functioning (PF), role-physical (RP), bodily pain (BP), general health (GH), vitality (VT), social functioning (SF), role-emotional (RE), mental health (MH);

Functional Assessment of Chronic Illness Therapy (FACIT)-Fatigue; and

Morning stiffness duration visual analog scale (VAS).

The ability of IL-6 levels to predict improvements in HRQoL was tested using a linear fixed effect model on CFB in HRQoL endpoints; with treatment, study randomization stratification factor (region), baseline PRO, IL-6 tertile at baseline, and IL-6 tertile at baseline-by-treatment interaction terms were defined as fixed effects variables. The IL-6 tertile at baseline-by-treatment interaction term specifically evaluated the incremental treatment effect (i.e. a whether there was a significantly higher change in PRO (patient reported outcomes) scores) for patients treated with sarilumab versus adalimumab in the high or medium IL-6 tertile groups, respectively, compared with the low IL-6 tertile group. P-values for the interaction terms were calculated using the low tertile as reference.

To evaluate response rates on minimal clinically important differences (MCID), logistic regression was carried out on response (within-patient MCID), with treatment, study randomization stratification factors, IL-6 tertile at baseline, and IL-6 tertile at baseline-by-treatment interaction as fixed effects. Responders were defined as patients reporting improvements ≥MCID at Week 24: 2.5 for PCS and MCS, 4.0 for FACIT, 10.0 for morning stiffness duration. Pairwise comparisons were performed separately in each IL-6 tertile, and the Mantel-Haenszel estimate (stratified by randomization factors) of odds ratio (OR) and 95% CIs were derived.

Results

Patients with high baseline IL-6 levels had significantly worse scores on SF-36 MCS, SF, RE, RP and BP and morning stiffness duration than patients with medium or low IL-6 levels (Kruskal-Wallis test p<0.05) (data not shown).

Figures 18A, 18B, 18C:
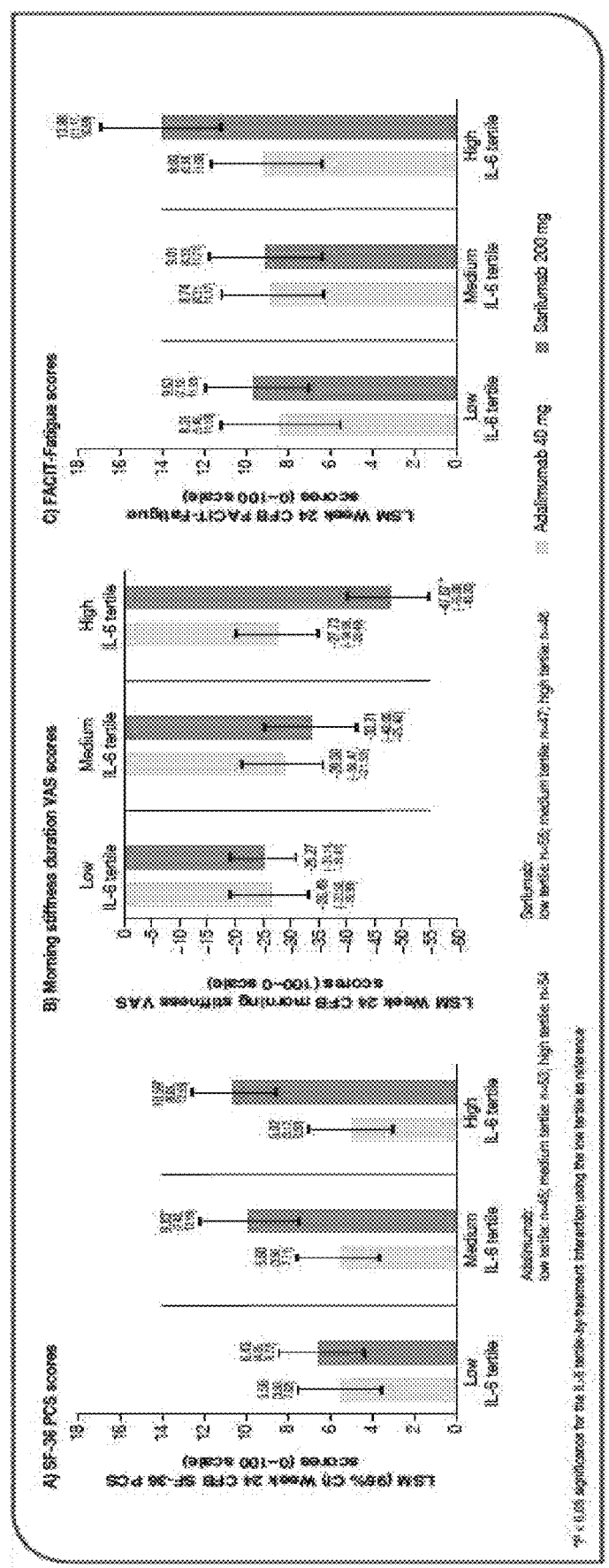
FIG. 18A is a graph depicting the least-squares mean Week 24 change from baseline on SF-36 PCS score endpoints by IL-6 tertile. *P<0.05 significance for the IL-6 tertile-by-treatment interaction using the low tertile as reference. Adalimumab: low tertile: n=45; medium tertile: n=53; high tertile: n=54; Sarilumab: low tertile: n=55; medium tertile: n=47; high tertile: n=46.
FIG. 18B is a graph depicting the least-squares mean Week 24 change from baseline on morning stiffness duration VAS score endpoints by IL-6 tertile. *P<0.05 significance for the IL-6 tertile-by-treatment interaction using the low tertile as reference. Adalimumab: low tertile: n=45; medium tertile: n=53; high tertile: n=54; Sarilumab: low tertile: n=55; medium tertile: n=47; high tertile: n=46.
FIG. 18C is a graph depicting the least-squares mean Week 24 change from baseline on FACIT-Fatigue score endpoints by IL-6 tertile. *P<0.05 significance for the IL-6 tertile-by-treatment interaction using the low tertile as reference. Adalimumab: low tertile: n=45; medium tertile: n=53; high tertile: n=54; Sarilumab: low tertile: n=55; medium tertile: n=47; high tertile: n=46.

The interaction p Value comparing the differences in PRO improvements in high versus low IL-6 tertile was significant for SF-36 PCS, PF domain, and morning stiffness duration, indicating that for patients with high IL-6 level, their improvements in HRQoL endpoints with sarilumab treatment versus adalimumab was significantly higher than those in low IL-6 levels in:

SF-36 PCS (LSM of the difference: 5.57, 95% CI [2.85, 8.28] versus 0.87 [−1.91, 3.66]), (FIG. 18A); and Morning stiffness duration, (−19.93 [−30.30, −9.56] versus 1.21 [−8.17, 10.60]) (FIG. 18B).

Figure 19:
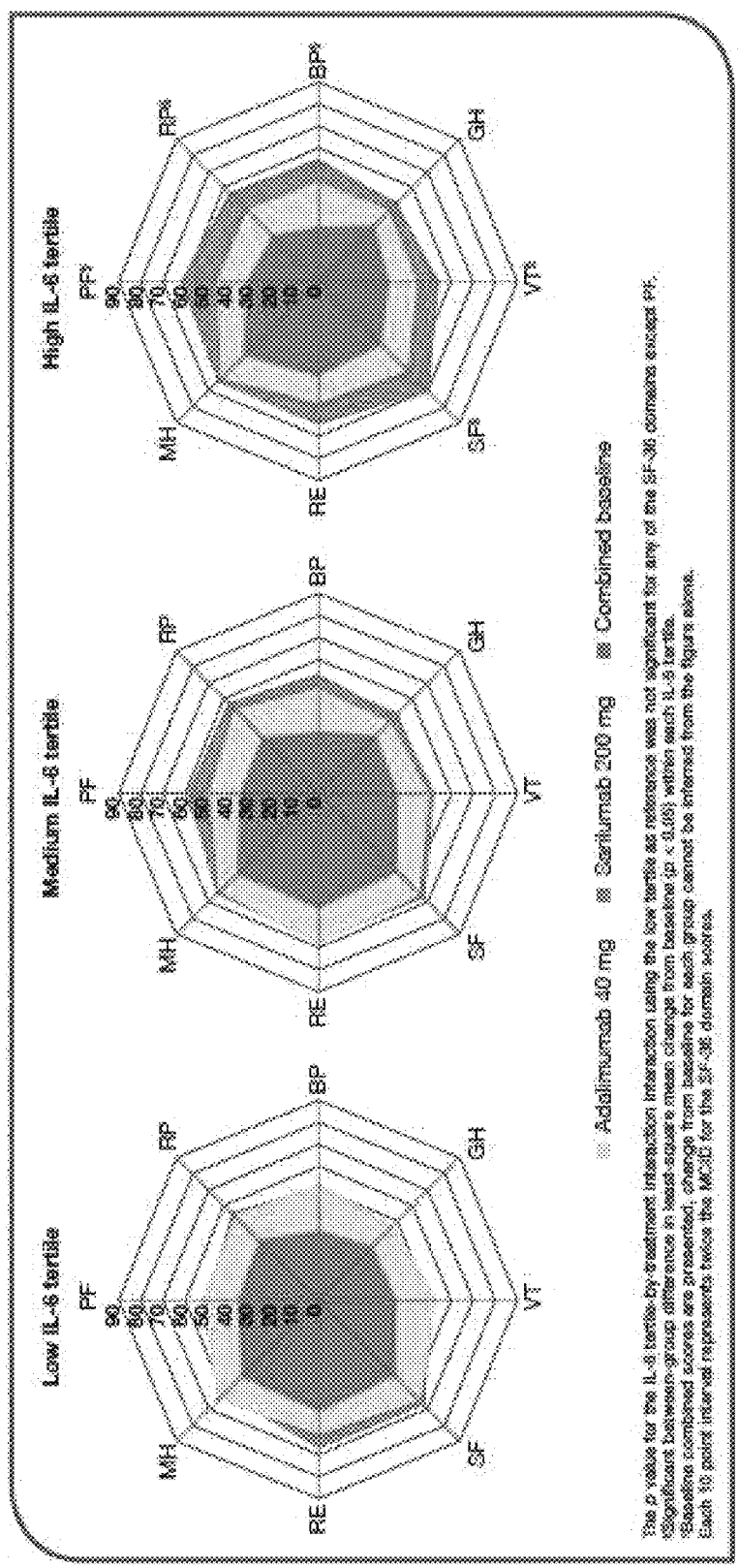
FIG. 19 depicts the mean SF-36 domain scores for adalimumab and sarilumab (combined baseline † and Week 24) by IL-6 tertile. The p value for the IL-6 tertile-by-treatment interaction interaction using the low tertile as reference was not significant for any of the SF-36 domains except PF. § Significant between-group difference in least-square mean change from baseline (p<0.05) within each IL-6 tertile. † Baseline combined scores are presented, change from baseline for each group cannot be inferred from the figure alone. Each 10 point interval represents twice the MCID for the SF-36 domain scores.

Although the interaction p-values were not significant, there were significant differences (p<0.05) for sarilumab versus adalimumab within the high IL-6 tertile for RP, BP, VT and SF, but not in the low or medium IL-6 tertiles (FIG. 19). There was also a significant difference (p<0.05) for sarilumab versus adalimumab within the high IL-6 tertile only for FACIT-Fatigue: (4.86 [1.06, 8.65] versus 1.21 [−2.59, 5.02]) (FIG. 18C).

A significant interaction was also observed for the PCS MCID response only, with an odds ratio (OR) in the high IL-6=(6.31 [2.37, 16.81]) versus low IL-6 (0.97 [0.43, 2.16]), indicating that for patients with high IL6 level, their odds of achieving MCID in PCS with sarilumab versus. adalimumab was significantly higher than those with low IL-6 levels (data not shown).

Conclusions

Evaluation of IL-6 biomarker associations with HRQoL endpoints indicate that RA patients with high IL-6 levels report worse HRQoL at baseline compared with patients with medium or low IL-6 levels.

The difference in treatment effect of sarilumab versus adalimumab was statistically higher for high IL-6 patients versus low IL-6 patients for PCS, the PF domain and morning stiffness duration.

For PCS, the results were confirmed by the analyses of response rates on MCID between tertiles.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for treating a subject having rheumatoid arthritis (RA), comprising
   determining the level of interleukin 6 (IL-6) in a serum sample(s) obtained from the subject having RA, and
   administering to the subject a therapeutically effective amount of a human anti-interleukin 6 receptor (IL-6R) antibody or antigen-binding portion thereof if the level of IL-6 in the subject sample(s) is determined to be a high IL-6 level,
   wherein the high IL-6 level is about ≥3 times the upper limit of normal (≥3×ULN),
   wherein the anti-IL-6R antibody, or antigen-binding portion thereof, comprises three heavy chain complementarity determining region (HCDR) sequences HCDR1, HCDR2, and HCDR3 comprising SEQ ID NOs:21, 23, 25, respectively, and three light chain complementarity determining (LCDR) sequences LCDR1, LCDR2, and LCDR3 comprising SEQ ID NOs: 29, 31, 33, respectively, and
   wherein the therapeutically effective amount of the human anti-IL-6R antibody or antigen-binding portion thereof is administered to the subject as a dose of about 200 mg about once every two weeks (q2w), thereby treating the subject.

2. The method of claim 1, wherein the subject was previously diagnosed as having RA.

3. The method of claim 1, wherein the subject is a treatment naïve RA subject or has previously been administered one or more therapeutic agents for treating RA.

4. A method for treating subjects having rheumatoid arthritis, the method comprising the steps of:
   determining the level of interleukin 6 (IL-6) in serum samples from the subjects so that each subject is determined to belong to either a first category of rheumatoid arthritis disease severity or a second category of rheumatoid arthritis disease severity;
   wherein the first category of rheumatoid arthritis disease severity corresponds to a high level of IL-6 and the second category of rheumatoid arthritis disease severity corresponds to a moderate level of IL-6 and/or a low level of IL-6,
   wherein a high level of IL-6 is about ≥3 times the upper limit of normal (≥3×ULN);
   assigning a therapy to the subjects in the first category of rheumatoid arthritis disease severity, wherein the therapy is administration of a therapeutically effective amount of a human anti-interleukin 6 receptor (IL-6R) antibody, or antigen-binding portion thereof; and
   administering the human IL-6R antibody, or antigen-binding portion thereof, to the subjects in the first category of rheumatoid arthritis disease severity,
   wherein the anti-IL-6R antibody, or antigen-binding portion thereof, comprises three heavy chain complementarity determining region (HCDR) sequences HCDR1, HCDR2, and HCDR3 comprising SEQ ID NOs:21, 23, 25, respectively, and three light chain complementarity determining (LCDR) sequences LCDR1, LCDR2, and LCDR3 comprising SEQ ID NOs: 29, 31, 33, respectively, and
   wherein the therapeutically effective amount of the human anti-IL-6R antibody or antigen-binding portion thereof is administered to the subject as a dose of about 200 mg about once every two weeks (q2w), thereby treating the subjects having rheumatoid arthritis.

5. A method for treating a subject having high interleukin 6 rheumatoid arthritis (high IL-6RA), comprising
   selecting a subject having high IL-6RA,
   wherein the subject having high IL-6RA has a serum level of IL-6 that is about ≥3 times the upper limit of normal (≥3×ULN), and
   administering to the subject a therapeutically effective amount of a human anti-interleukin 6 receptor (IL-6R) antibody, or antigen-binding portion thereof,
   wherein the anti-IL-6R antibody, or antigen-binding portion thereof, comprises three heavy chain complementarity determining region (HCDR) sequences HCDR1, HCDR2, and HCDR3 comprising SEQ ID NOs:21, 23, 25, respectively, and three light chain complementarity determining (LCDR) sequences LCDR1, LCDR2, and LCDR3 comprising SEQ ID NOs: 29, 31, 33, respectively, and
   wherein the therapeutically effective amount of the human anti-IL-6R antibody or antigen-binding portion thereof is administered to the subject as a dose of about 200 mg about once every two weeks (q2w), thereby treating the subject.

6. A method for inhibiting joint damage in a subject, comprising
   selecting a treatment naïve subject having high interleukin 6 rheumatoid arthritis (high IL-6RA),
   wherein the subject having high IL-6RA has a serum level of IL-6 that is about ≥3 times the upper limit of normal (≥3×ULN), and
   administering to the subject a therapeutically effective amount of a human anti-interleukin 6 receptor (IL-6R) antibody, or antigen-binding portion thereof, as a monotherapy,
   wherein the anti-IL-6R antibody, or antigen-binding portion thereof, comprises three heavy chain complementarity determining region (HCDR) sequences HCDR1, HCDR2, and HCDR3 comprising SEQ ID NOs:21, 23, 25, respectively, and three light chain complementarity determining (LCDR) sequences LCDR1, LCDR2, and LCDR3 comprising SEQ ID NOs: 29, 31, 33, respectively,
   wherein the therapeutically effective amount of the human anti-IL-6R antibody or antigen-binding portion thereof is administered to the subject as a dose of about 200 mg about once every two weeks (q2w), thereby inhibiting joint damage in the subject.

7. The method of any one of claims 1, 4, 5, and 6, wherein the anti-IL-6R antibody, or antigen-binding portion thereof, is a fully human anti-IL-6R antibody, or antigen-binding portion thereof.

8. The method of any one of claims 1, 4, 5, and 6, wherein the anti-IL-6R antibody, or antigen-binding portion thereof, is administered to the subject in a pharmaceutical composition.

9. The method of claim 8, wherein the pharmaceutical composition is present in a pre-filled syringe.

10. The method of any one of claims 1, 4, 5, and 6, wherein the anti-IL-6R antibody, or antigen-binding portion thereof, comprises an HCVR having the amino acid sequence of SEQ ID NO: 19 and an LCVR having the amino acid sequence of SEQ ID NO: 27.

11. The method of claim 10, wherein the anti-IL-6R antibody, or antigen-binding portion thereof, is sarilumab, or a biosimilar thereof.

12. A method for treating a subject having rheumatoid arthritis, the method comprising:
- selecting a subject previously treated with adalimumab or a biosimilar of adalimumab, who has or presented with high IL-6 serum levels, and had an inadequate response to adalimumab or a biosimilar of adalimumab,
- wherein the high IL-6 level is about ≥3 times the upper limit of normal (≥3×ULN),
- discontinuing adalimumab treatment for the subject, and
- initiating a therapeutic regimen comprising about 200 mg about once every two weeks (q2w) of sarilumab for the subject,
- thereby treating the subject.

13. The method of any one of claims 1, 4, and 5-12, wherein the high IL-6RA level that is ≥3×ULN is ≥30 pg/mL serum IL-6.

* * * * *

UNITED STATES PATENT AND TRADEMARK OFFICE
CERTIFICATE OF CORRECTION

| | | |
|---|---|---|
| PATENT NO. | : 11,319,375 B2 | |
| APPLICATION NO. | : 16/553338 | |
| DATED | : May 3, 2022 | |
| INVENTOR(S) | : Anita Boyapati et al. | |

It is certified that error appears in the above-identified patent and that said Letters Patent is hereby corrected as shown below:

On the Title Page

Item (71) Applicants:
Please delete the first Applicant, "Regeneran Pharmaceuticals, Inc.", and replace it with -- Regeneron Pharmaceuticals, Inc. --

Signed and Sealed this
Twelfth Day of July, 2022

Katherine Kelly Vidal
*Director of the United States Patent and Trademark Office*